(12) United States Patent
Piotrowski et al.

(10) Patent No.: US 6,919,359 B2
(45) Date of Patent: Jul. 19, 2005

(54) AZABICYCLIC-SUBSTITUTED-HETEROARYL COMPOUNDS FOR THE TREATMENT OF DISEASE

(75) Inventors: David W. Piotrowski, Portage, MI (US); Jason K. Myers, Kalamazoo, MI (US); Bruce N. Rogers, Portage, MI (US); Eric Jon Jacobsen, Richland, MI (US); Alice L. Bodnar, Kalamazoo, MI (US); Vincent E. Groppi, Jr., Kalamazoo, MI (US); Daniel Patrick Walker, Kalamazoo, MI (US); Brad A. Acker, Kalamazoo, MI (US)

(73) Assignee: Pfizer Inc, New York, NY (US)

( * ) Notice: Subject to any disclaimer, the term of this patent is extended or adjusted under 35 U.S.C. 154(b) by 148 days.

(21) Appl. No.: 10/288,863

(22) Filed: Nov. 6, 2002

(65) Prior Publication Data

US 2003/0207913 A1 Nov. 6, 2003

Related U.S. Application Data

(60) Provisional application No. 60/357,906, filed on Feb. 19, 2002, provisional application No. 60/358,142, filed on Feb. 19, 2002, provisional application No. 60/358,159, filed on Feb. 19, 2002, provisional application No. 60/350,108, filed on Nov. 13, 2001, and provisional application No. 60/336,977, filed on Nov. 8, 2001.

(51) Int. Cl.[7] ........................ A61K 31/44; C07D 409/04
(52) U.S. Cl. ................ 514/342; 546/268.1; 546/269.1; 546/269.7; 546/280.4; 546/271.4; 546/281.7; 548/236; 514/336; 514/374; 514/211.01; 514/211.15; 540/484
(58) Field of Search ........................ 540/484; 548/236; 514/374, 211.01, 211.15, 336, 340, 268.1, 269.1, 280.4; 546/268.1, 269.1, 280.4

(56) References Cited

U.S. PATENT DOCUMENTS

| | | | |
|---|---|---|---|
| 4,605,652 A | 8/1986 | Welstead, Jr. | 514/214 |
| 4,798,829 A | 1/1989 | King et al. | 514/214 |
| 4,835,162 A | 5/1989 | Abood | 514/305 |
| 4,863,919 A | 9/1989 | Smith | 514/214 |
| 4,988,691 A | 1/1991 | Benelli et al. | 514/214 |
| 5,017,580 A | 5/1991 | Naylor et al. | 514/299 |
| 5,025,022 A | 6/1991 | Naylor et al. | 514/305 |
| 5,039,680 A | 8/1991 | Impoerato et al. | 514/304 |
| 5,057,519 A | 10/1991 | Suberg | 514/282 |
| 5,106,843 A | 4/1992 | Ward et al. | 514/213 |
| 5,175,173 A | 12/1992 | Sun | 514/305 |
| 5,217,975 A | 6/1993 | Wadsworth et al. | 514/299 |
| 5,342,845 A | 8/1994 | Chokai et al. | 514/305 |
| 5,364,863 A | 11/1994 | Cohen et al. | 514/304 |
| 5,510,478 A | 4/1996 | Sabb | 540/585 |
| 5,561,149 A | 10/1996 | Azria et al. | 514/397 |
| 5,624,941 A | 4/1997 | Barth et al. | 514/326 |
| 5,712,270 A | 1/1998 | Sabb | 514/212 |
| 5,977,144 A | 11/1999 | Meyer et al. | 514/334 |

FOREIGN PATENT DOCUMENTS

| | | | |
|---|---|---|---|
| EP | 327335 A1 | 2/1988 | ......... A61K/31/435 |
| EP | 378111 A1 | 7/1990 | ......... C07D/413/12 |
| JP | 04-247081 | 9/1992 | ......... C07D/451/04 |
| WO | WO 92/15579 | 9/1992 | ......... C07D/451/00 |
| WO | WO97/30998 | 8/1997 | ......... C07D/453/02 |
| WO | WO98/54189 | 12/1998 | ......... C07D/491/20 |
| WO | WO 00/73431 A2 | 12/2000 | ........... C12N/15/00 |
| WO | WO 01/36417 A1 | 5/2001 | ......... C07D/451/04 |
| WO | WO01/60821 | 8/2001 | |

OTHER PUBLICATIONS

Bannon, A.W., *American Association for the Advancement of Science*. Broad–Spectrum, Non–Opiodid Analgesic Activity by Selective Modulation of Neuronal Nicotinic Acetylcholine Receptors. vol. 279, No 5347, pp. 77–81, 1998.

Holladay, Mark W., et al., *Journal of Medicinal Chemistry*. Neuronal Nicotinic Acetylcholine Receptors as Targets for Drug Discovery. Dec. 19, 1997.

Kem, William R. *Behavioral Brain Research*. "The brain α7 nicotinic receptor may be an important therapeutic target for treatment of Alzheimer's disease: studies with DMXBA (GTS–21)." 113(2000) 169–181.

Macor, JE. *Bioorganic & Medicinal Chemistry Letters*. "The 5–HT$_3$ Antagonist Tropisrtron (ICS 205–930) is a Potent and Selective α7 Nicotinic Receptor Partial Agonist." 11(2001) 319–321.

*Primary Examiner*—Golam M M Shameem
(74) *Attorney, Agent, or Firm*—Peter C. Richardson; Lorraine B. Ling; Eileen M. Ebel

(57) ABSTRACT

The invention provides compounds of Formula I:

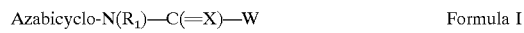

Azabicyclo-N(R$_1$)—C(=X)—W    Formula I

These compounds may be in the form of pharmaceutical salts or compositions, racemic mixtures, or pure enantiomers thereof. The compounds of Formula I are useful in pharmaceuticals in which α7 is known to be involved.

23 Claims, No Drawings

AZABICYCLIC-SUBSTITUTED-HETEROARYL COMPOUNDS FOR THE TREATMENT OF DISEASE

CROSS-REFERENCE TO RELATED APPLICATIONS

This application claims the benefit of U.S. provisional application Ser. No. 60/336,977, filed on 8 Nov. 2001, under 35 USC 119(e)(i), U.S. provisional application Ser. No. 60/350,108 filed on 13 Nov. 2001, under 35 USC 119(e)(i), U.S. provisional application Ser. No. 60/357,906, filed on 19 Feb. 2002, under 35 USC 119(e)(i), U.S. provisional application Ser. No. 60/358,142 filed on 19 Feb. 2002, under 35 USC 119(e)(i), and U.S. provisional application Ser. No. 60/358,159 filed on 19 Feb. 2002, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

U.S. Pat. No. 6,441,049 B2 disclsoes a method of treating nerodegenerative disorders via inhibition of amyloid beta peptide binding.

U.S. Pat. No. 6,255,490 B1 discloses 7-azabicyclo[2.2.1]-heptane and -heptene derivatives as cholinergic receptor ligands.

U.S. Pat. No. 6,060,473 discloses7-azabicyclo[2.2.1]-heptane and -heptene derivatives as cholinergic receptor ligands.

U.S. Pat. No. 6,054,464 discloses azabicyclic esters of carbamic acids useful in therapy, especially in the treatment or prophylaxis of psychotic disorders and intellectual impairment disorders, as well as intermediates and use of intermediates in synthesis.

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,712,270 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to $5HT_{1A}$ receptors and dopamine $D_2$ receptors, making them useful as antipsychotic agents.

U.S. Pat. No. 5,624,941 discloses pyrazole derivatives useful in pharmaceuticals in which cannabis is known to be involved.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,510,478 discloses a group of 2-aroylaminothiazole derivatives which bind to and stimulate central muscarinic acetylcholine receptors and are useful agents for treating symptoms of cognitive disorders, specifically the impaired memory associated with a decrease in the neurotransmitter, acetylcholine. Some of the compounds of this invention also bind to $5HT_{1A}$ receptors and dopamine $D_2$ receptors, making them useful as antipsychotic agents.

U.S. Pat. No. 5,364,863 discloses bicyclic carboxylic esters and amides, their pharmaceutical formulations, and a method for their use in treating migraine, emesis, gastrointestinal-disorders, schizophrenia, or anxiety in mammals.

U.S. Pat. No. 5,217,975 discloses azabicyclic compounds for treating dementia.

U.S. Pat. No. 5,106,843 discloses heterocyclic compounds useful as $5-HT_3$ antagonists.

U.S. Pat. No. 5,057,519 discloses $5-HT_3$ antagonists as being useful in reducing opiate tolerance.

U.S. Pat. No. 5,039,680 discloses $5-HT_3$ antagonists in preventing or reducing dependency on dependency-inducing agents.

U.S. Pat. No. 4,988,691 discloses isoxazole-containing compounds exhibiting anti-serotonin activity.

U.S. Pat. No. 4,921,982 discloses 5-halo-2,3-dihydro-2,2-dimethylbenzofuran-7-carboxylic acids which are useful as intermediates for $5-HT_3$ antagonists.

U.S. Pat. No. 4,863,919 discloses a method of enhancing memory or correcting memory deficiency with arylamido-(and arylthioamido-)azabicyclalkanes.

U.S. Pat. No. 4,835,162 discloses agonists and antagonists to nicotine as smoking deterrents.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

U.S. patent application Ser. No. 2002/0016334 discloses a pharmaceutical composition for the treatment of attention deficit hyperactivity disorder.

WO 01/60821 discloses novel biarylcarboxamides.

WO 01/36417 A1 discloses novel N-azabicyclo-amide derivatives and use in therapy, especially in the treatment of prophylaxis of psychotic disorders and intellectual impairment disorders.

WO 01/29304 discloses quinuclidine acrylamides.

WO 00/73431 A2 discloses two binding assays to directly measure the affinity and selectivity of compounds at the α7 nAChR and the $5-HT_3R$. The combined use of these functional and binding assays may be used to identify compounds that are selective agonists of the α7 nAChR.

WO 98/54189 discloses spiro-quinuclidine derivatives, their preparation and use.

WO 97/30998 discloses azabicyclic esters of carbamic acids useful in therapy.

WO 95/01793 discloses 5-HT$_3$ antagonists as topical medicaments for treatment of peripheral disorders associated with pain.

WO 92/15579 discloses multicyclic tertiary amine polyaromatic squalene synthase inhibitors and method of treatment for lowering serum cholesterol levels using the compounds.

WO 92/21339 discloses isoxazole and isothiazole compounds that enhance cognitive function.

JP 04-247081 discloses 5-membered heterocyclic acid amides.

In *Bioorg. & Med. Chem. Lett.* 11 (2001) 319–321, the 5-HT$_3$ antagonist tropisetron (ICS 205–930) is discussed as a potent and selective α7 Nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

In *J Med. Chem.*, 40 (1997), 4169–4194, neuronal nicotinic acetylcholine receptors are discussed as targets for drug discovery.

In *Science*, 279 (1998), 77–81, the broad-spectrum, non-opioid analgesic activity is discussed by selective modulation of neuronal nicotinic acetylcholine receptors.

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *J Neurochem.*, 1997, 68(5): 2140–51). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., *Nature*, 366(6454), p 479–83, 1993), and the pore forming C-terminal domain of the 5-HT$_3$ receptor expressed well in *Xenopus* oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

SUMMARY OF THE INVENTION

The present invention discloses compounds of the Formula I:

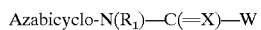

Azabicyclo-N(R$_1$)—C(=X)—W    Formula I wherein, X is O or S;

R$_1$ is H, alkyl, cycloalkyl, halogenated alkyl, or aryl;

W is a cyclic heteroaromatic moiety where the heteroatoms can be from 1–2 atoms selected from oxygen, sulfur, or nitrogen of the following structures:

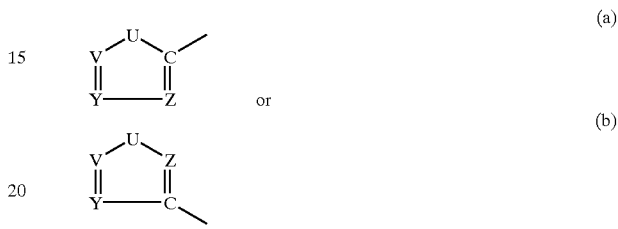

wherein U is —O—, —S—, or —N(R$_U$)—;

V and Y are independently =N—, or =C(R$_{VY}$)—;

Z is =N—, or =CH—, provided that when both V and Y are =C(R$_{VY}$)— and Z is =CH—, only one =C(R$_{VY}$)— can be =CH—, further provided that when U is —O—, Y is =C(R$_{VY}$)— and Z is =C(H)—, V cannot be =N—, and further provided that no more than one of V, Y, or Z is a heteroatom;

R$_U$ is H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —SO$_2$R$_8$, and provided that when W is (b) and Z is =N— and U is N(R$_U$), R$_U$ cannot be phenyl or substituted phenyl;

Each R$_{VY}$ is independently H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —OR$_8$, —OR$_{14}$, —SR$_8$, —SR$_{14}$, F, Cl, Br, I, —NR$_8$R$_8$, —NR$_{14}$R$_{14}$, —C(O)R$_8$, —C(O)R$_{14}$, —C(O)NR$_8$R$_8$, —C(O)NR$_{14}$R$_{14}$, —C(R$_6$)=N(R$_{16}$), —CN, —NR$_8$C(O)R$_{11}$, —S(O)$_2$NR$_8$R$_8$, —OS(O)$_2$R$_{11}$, —S(O)$_2$R$_8$, —S(O)$_2$R$_{14}$, —NR$_8$S(O)$_2$R$_8$,—N(H)C(O)N(H)R$_8$, —NO$_2$, R$_7$, R$_9$, and 0–3 substituents independently selected from F, Cl, Br, I, or R$_{15}$, and 0–3 substituents independently selected from F, Cl, Br, I, or R$_{15}$;

Azabicyclo is

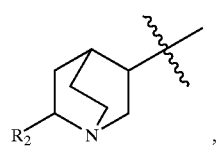

I

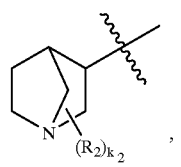

II

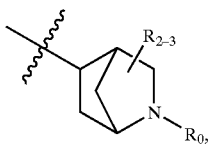

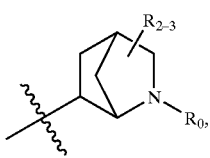

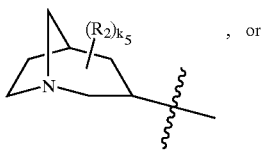

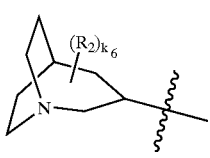

$R_0$ is H, lower alkyl, substituted lower alkyl, or halogenated lower alkyl;

$R_2$ is alkyl, halogenated alkyl, substituted alkyl, cycloalkyl, aryl or $R_2$ is absent provided that $k_2$, $k_5$, or $k_6$ is 0;

$k_2$ is 0 or 1;

$k_5$ and $k_6$ are independently 0, 1, or 2;

$R_{2-3}$ is H, alkyl, halogenated alkyl, substituted alkyl, F, Cl, Br, or I;

$R_6$ is H, F, Cl, CN, alkyl, substituted alkyl, cycloalkyl, halogenated alkyl, and aryl;

$R_7$ is 5-membered heteroaromatic mono-cyclic moieties containing within the ring 1–3 heteroatoms independently selected from the group consisting of —O—, =N—, —N($R_{19}$)—, and —S—, and having 0–1 substituent selected from $R_{20}$ and further having 0–3 substituents independently selected from F, Cl, Br, or I, or $R_7$ is a 9-membered fused-ring moiety having a 6-membered ring fused to a 5-membered ring and having the formula

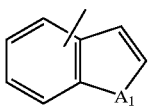

wherein $A_1$ is O, S, or $NR_{19}$,

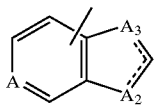

wherein A is $CR_{18}$ or N, $A_2$ and $A_3$ are independently selected from $CR_{18}$, $C(R_{18})_2$, O, S, N, or $NR_{19}$, provided that both $A_2$ and $A_3$ are not simultaneously O, simultaneously S, or simultaneously O and S, or

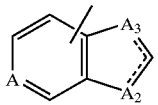

wherein A is $CR_{18}$ or N, $A_2$ and $A_3$ are independently selected from $CR_{18}$, $C(R_{18})_2$, O, S, N, or $NR_{19}$, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, $R_7$, $R_9$, or phenyl having 1 substituent selected from $R_{20}$ and further having 0–3 substituents independently selected from F, Cl, Br, or I;

Each $R_{11}$ is independently H, alkyl, cycloalkyl, heterocycloalkyl, halogenated alkyl, halogenated cycloalkyl, or halogenated heterocycloalkyl;

$R_{13}$ is —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$CF_3$, or —$NO_2$;

Each $R_{14}$ is independently H, alkyl, halogenated alkyl, limited substituted alkyl, cycloalkyl, halogenated cycloalkyl, substituted cycloalkyl, heterocycloalkyl, halogenated heterocycloalkyl, or substituted heterocycloalkyl;

$R_{15}$ is alkyl, substituted alkyl, halogenated alkyl, —$OR_{11}$, —CN, —$NO_2$, —$NR_{10}R_{10}$;

$R_{16}$ is —$OR_{17}$, —$NR_{17}R_{17}$, —$NR_{17}C(O)R_{17}$, —$NR_{17}S(O)_2R_{17}$, —$N(R_{17})C(O)NR_{17}R_{17}$, —$NR_{17}C(O)OR_{17}$;

$R_{17}$ is H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, phenyl, phenyl having 1–4 substituents independently selected from F, Cl, Br, I and $R_{15}$, naphthyl, or naphthyl having 1–4 substituents independently selected from F, Cl, Br, I and $R_{15}$;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, F, Cl, Br, or I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

or pharmaceutical composition, pharmaceutically acceptable salt, racemic mixture, or pure enantiomer thereof.

Embodiments of the invention may include one or more or combination of the following.

An embodiment of the present invention provides a use of a compound of Formula I for treating a disease or condition, wherein the diseases, disorders, and/or condition is any one or more or combination of the following: cognitive and attention deficit symptoms of Alzheimer's Disease, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

In another aspect, the invention includes treating a mammal suffering from schizophrenia or psychosis by administering compounds of Formula I in conjunction with antipsychotic drugs (also called anti-psychotic agents). The compounds of the present invention and the antipsychotic drugs can be administered simultaneously or at separate intervals. When administered simultaneously the compounds of the present invention and the antipsychotic drugs can be incorporated into a single pharmaceutical composition. Alternatively, two separate compositions, i.e., one containing compounds of the present invention and the other containing antipsychotic drugs, can be administered simultaneously.

The present invention also includes the compounds of the present invention, pharmaceutical compositions containing the active compounds as the free base or as a pharmaceutically acceptable salt and a pharmaceutically acceptable carrier, and methods to treat the identified diseases.

A further embodiment of the present invention provides a method comprising administering a therapeutically effective amount of a compound of the present invention or a pharmaceutical composition contains said compound to the mammal.

The present invention also includes a pharmaceutical composition comprising a compound of Formula I or a pharmaceutically acceptable salt thereof and a pharmaceutically acceptable excipient. The pharmaceutical composition is administered rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

A pharmaceutical composition comprising a compound of Formula I or a pharmaceutically acceptable salt thereof, an anti-psychotic agent, and a pharmaceutically acceptable excipient. The pharmaceutical composition is administered to independently administer said compound and said agent rectally, topically, orally, sublingually, or parenterally for a therapeutically effective interval. The pharmaceutical composition is administered to deliver a compound of the present invention in an amount of from about 0.001 to about 100 mg/kg of body weight of said mammal per day. The pharmaceutical composition is also administered to deliver a compound of the present invention in an amount of from about 0.1 to about 50 mg/kg of body weight of said mammal per day.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist.

The present invention also includes a use of a compound according to Formula I or pharmaceutically acceptable salt thereof for the preparation of a medicament for treating a disease or condition, wherein the mammal would receive symptomatic relief from the administration of a therapeutically effective amount of α7 nicotinic acetylcholine receptor agonist, wherein the disease, or condition is any one or more or combination of the following: cognitive and attention deficit symptoms of Alzheimer's Disease, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

The present invention also includes a method for treating a disease or condition in a mammal in need thereof, wherein the mammal would receive symptomatic relief from the administration of an α7 nicotinic acetylcholine receptor agonist comprising administering to the mammal a therapeutically effective amount of a compound according to Formula I or pharmaceutically acceptable salt thereof.

The present invention also includes a method for treating a disease or condition in a mammal in need thereof comprising administering to the mammal a therapeutically effective amount of a compound according to Formula I or pharmaceutically acceptable salt thereof, wherein the disease or condition is any one or more or combination of the following: cognitive and attention deficit symptoms of Alzheimer's Disease, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Another embodiment of the present invention includes compounds where X is O or S.

Another embodiment of the present invention includes compounds where $R_1$ is H, alkyl, or cycloalkyl.

Another embodiment of the present invention includes compounds where Azabicyclo is any one or more of I, II, III, IV, V, or VI.

Another embodiment of the present invention includes compounds where $R_2$ is lower alkyl or is absent provided that $k_2$, $k_5$ or $k_6$ is 0; and where $R_{2-3}$ is H or lower alkyl.

Another embodiment of the present invention includes compounds where W is (a) or (b).

Another embodiment of the present invention includes compounds where (a) is thiophen-2-yl, furan-2-yl, 1,3-thiazol-5-yl, or 1,3-oxazol-2-yl, 1,3-thiazol-2-yl, 1,3,4-oxadiazol-2-yl, 1,3-oxazol-5-yl, 1H-pyrrol-2-yl, or 1,2,4-oxadiazol-5-yl, any of which is optionally substituted on carbon independently with alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —$OR_8$, —$OR_{14}$, —$SR_8$, —$SR_{14}$, F, Cl, Br, I, —$NR_8R_8$, —$NR_{14}R_{14}$, —$C(O)R_8$, —$C(O)R_{14}$, —$C(O)NR_8R_8$, —$C(O)NR_{14}R_{14}$, —$C(R_6)$=$N(R_{16})$, —CN, —$NR_8C(O)R_{11}$, —$S(O)_2NR_8R_8$, —$OS(O)_2R_{11}$, —$S(O)_2R_8$, —$S(O)_2R_{14}$, —$NR_8S(O)_2R_8$, —$N(H)C(O)N(H)R_8$, —$NO_2$, $R_7$, $R_9$, and 0–3 substituents independently selected from F, Cl, Br, I, or $R_{15}$, and 0–3 substituents independently selected from F, Cl, Br, I, or $R_{15}$; and further optionally substituted on nitrogen with alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —$SO_2R_8$. One of ordinary skill in the art can identify where substituents are allowed according to Formula I.

Another embodiment of the present invention includes compounds where (b) is 1,3-thiazol-4-yl, 1,3-oxazol-4-yl, 1H-1,2,4-triazol-3-yl, or isoxazol-3-yl, any of which is optionally substituted on carbon independently with alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —$OR_8$, —$OR_{14}$, —$SR_8$, —$SR_{14}$, F, Cl, Br, I, —$NR_8R_8$, —$NR_{14}R_{14}$, —$C(O)R_8$, —$C(O)R_{14}$, —$C(O)NR_8R_8$, —$C(O)NR_{14}R_{14}$, —$C(R_6)$=$N(R_{16})$, —CN, —$NR_8C(O)R_{11}$, —$S(O)_2NR_8R_8$, —$OS(O)_2R_{11}$, —$S(O)_2R_8$, —$S(O)_2R_{14}$, —$NR_8S(O)_2R_8$, —$N(H)C(O)N(H)R_8$, —$NO_2$, $R_7$, $R_9$, and 0–3 substituents independently selected from F, Cl, Br, I, or $R_{15}$, and 0–3 substituents independently selected from F, Cl, Br, I, or $R_{15}$; and further optionally substituted on nitrogen with alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —$SO_2R_8$. One of ordinary skill in the art can identify where substituents are allowed according to Formula I.

Another embodiment of the present invention includes compounds where $R_U$ is any one or more of the following: H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —$SO_2R_8$, and provided that when W is (b) and Z is =N— and U is $N(R_U)$, $R_U$ cannot be phenyl or substituted phenyl.

Another embodiment of the present invention includes compounds where each $R_{YY}$ is independently any one or more of the following: H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —$OR_8$, —$OR_{14}$, —$SR_8$, —$SR_{14}$, F, Cl, Br, I, —$NR_8R_8$, —$NR_{14}R_{14}$, —$C(O)R_8$, —$C(O)R_{14}$, —$C(O)NR_8R_8$, —$C(O)NR_{14}R_{14}$, —$C(R_6)$=$N(R_{16})$, —CN, —$NR_8C(O)R_{11}$, —$S(O)_2NR_8R_8$, —$OS(O)_2R_{11}$, —$S(O)_2R_8$, —$S(O)_2R_{14}$, —$NR_8S(O)_2R_8$, —$N(H)C(O)N(H)R_8$, —$NO_2$, $R_7$, $R_9$, and 0–3 substituents independently selected from F, Cl, Br, I, or $R_{15}$, and 0–3 substituents independently selected from F, Cl, Br, I, or $R_{15}$.

Another embodiment of the present invention includes the compounds where $R_6$ is any one or more of the following: H, F, Cl, CN, alkyl, substituted alkyl, cycloalkyl, halogenated alkyl, and aryl.

Another embodiment of the present invention includes the compounds where each $R_8$ is independently any one or more of the following: H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl.

Another embodiment of the present invention includes the compounds where each $R_{11}$ is independently any one or more of the following: H, alkyl, cycloalkyl, heterocycloalkyl, halogenated alkyl, halogenated cycloalkyl, or halogenated heterocycloalkyl.

Another embodiment of the present invention includes the compounds where each $R_{14}$ is independently any one or more of the following: H, alkyl, halogenated alkyl, limited substituted alkyl, cycloalkyl, halogenated cycloalkyl, substituted cycloalkyl, heterocycloalkyl, halogenated heterocycloalkyl, or substituted heterocycloalkyl.

Another embodiment of the present invention includes the compounds where (a) is any one or more of the following: thiophen-2-yl, furan-2-yl, 1,3-thiazol-2-yl, 1,3-oxazol-2-yl, or 1H-pyrrol-2-yl, any of which is optionally substituted with up to 2 substituents wherein the substituents are bromo, chloro, methyl, phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-hydroxyphenyl, 3-hydroxyphenyl, 4-hydroxyphenyl, 2-aminophenyl, 3-aminophenyl, 4-aminophenyl, 2-acetylaminophenyl, 3-acetylaminophenyl, 4-acetylaminophenyl, 2-trifluoroacetamidophenyl, 3-trifluoroacetamidophenyl, 4-trifluoroacetamidophenyl, or pyridinyl. One of ordinary skill in the art can identify where substituents are allowed according to Formula I.

Another embodiment of the present invention includes any one or more of the following compounds as the free base or a pharmaceutically acceptable salt there of and as the pure enantiomer or as a racemic mixture thereof:

N-[(3R,5R)-1-azabicyclo[3.2.1]oct-3-yl]-5-bromothiophene-2-carboxamide;
N-[(exo-4(S))-1-azabicyclo[2.2.1]hept-3-yl]-5-bromothiophene-2-carboxamide;
N-[(exo-4(S))-1-azabicyclo[2.2.1]hept-3-yl]-5-(pyridin-2-yl)-thiophene-2-carboxamide;
N-[(exo-4(S))-1-azabicyclo[2.2.1]hept-3-yl]-5-phenylthiophene-2-carboxamide;
N-[(3R,5R)-1-azabicyclo[3.2.1]oct-3-yl]-5-phenyl-2-furamide;
N-[(3R,5R)-1-azabicyclo[3.2.1]oct-3-yl]-5-(2-fluorophenyl)-2-furamide;
N-[(exo-4(S))-1-azabicyclo[2.2.1]hept-3-yl]-5-phenyl-2-furamide;
N-[(exo-4(S))-1-azabicyclo[2.2.1]hept-3-yl]-5-(2-fluorophenyl)-2-furamide;
N-[(exo-4(S))-1-azabicyclo[2.2.1]hept-3-yl]-5-(3-fluorophenyl)-2-furamide;
N-[(exo-4(S))-1-azabicyclo[2.2.1]hept-3-yl]-5-(4-fluorophenyl)-2-furamide;
N-[(exo-4(S))-1-azabicyclo[2.2.1]hept-3-yl]-5-(4-methylphenyl)-2-furamide;
N-[(3R,5R)-1-azabicyclo[3.2.1]oct-3-yl]-5-phenyl-1,3-oxazole-2-carboxamide;
5-(4-aminophenyl)-N-[(3R,5R)-1-azabicyclo[3.2.1]oct-3-yl]-1,3-oxazole-2-carboxamide;
5-(4-acetylaminophenyl)-N-[(3R,5R)-1-azabicyclo[3.2.1]oct-3-yl]-1,3-oxazole-2-carboxamide; or
N-[(exo-4(S))-1-azabicyclo[2.2.1]hept-3-yl]-5-phenyl-1,3-oxazole-2-carboxamide.

Another embodiment of the present invention includes any one or more of the following compounds as the free base or a pharmaceutically acceptable salt there of and as the pure enantiomer or as a racemic mixture thereof:

N-[(3R,5R)-1-azabicyclo[3.2.1]oct-3-yl]-5-chlorothiophene-2-carboxamide;
N-[(3R,5R)-1-azabicyclo[3.2.1]oct-3-yl]-5-methylthiophene-2-carboxamide;
N-[(3R,5R)-1-azabicyclo[3.2.1]oct-3-yl]-5-phenylthiophene-2-carboxamide;
N-[(3R,5R)-1-azabicyclo[3.2.1]oct-3-yl]-5-(2-fluorophenyl)thiophene-2-carboxamide;
N-[(3R,5R)-1-azabicyclo[3.2.1]oct-3-yl]-5-(3-fluorophenyl)thiophene-2-carboxamide;
N-[(3R,5R)-1-azabicyclo[3.2.1]oct-3-yl]-5-(4-fluorophenyl)thiophene-2-carboxamide;
N-[(3R,5R)-1-azabicyclo[3.2.1]oct-3-yl]-5-(2-chlorophenyl)thiophene-2-carboxamide;
N-[(3R,5R)-1-azabicyclo[3.2.1]oct-3-yl]-5-(3-chlorophenyl)thiophene-2-carboxamide;
N-[(3R,5R)-1-azabicyclo[3.2.1]oct-3-yl]-5-(4-chlorophenyl)thiophene-2-carboxamide;
N-[(3R,5R)-1-azabicyclo[3.2.1]oct-3-yl]-5-(2-methoxyphenyl)thiophene-2-carboxamide;
N-[(3R,5R)-1-azabicyclo[3.2.1]oct-3-yl]-5-(3-methoxyphenyl)thiophene-2-carboxamide;
N-[(3R,5R)-1-azabicyclo[3.2.1]oct-3-yl]-5-(4-methoxyphenyl)thiophene-2-carboxamide;
N-[(3R,5R)-1-azabicyclo[3.2.1]oct-3-yl]-5-(2-methylphenyl)thiophene-2-carboxamide;
N-[(3R,5R)-1-azabicyclo[3.2.1]oct-3-yl]-5-(3-methylphenyl)thiophene-2-carboxamide;
N-[(3R,5R)-1-azabicyclo[3.2.1]oct-3-yl]-5-(4-methylphenyl)thiophene-2-carboxamide;
N-[(3R,5R)-1-azabicyclo[3.2.1]oct-3-yl]-5-(2-hydroxyphenyl)thiophene-2-carboxamide;
N-[(3R,5R)-1-azabicyclo[3.2.1]oct-3-yl]-5-(3-hydroxyphenyl)thiophene-2-carboxamide;
N-[(3R,5R)-1-azabicyclo[3.2.1]oct-3-yl]-5-(4-hydroxyphenyl)thiophene-2-carboxamide;
5-(2-aminophenyl)-N-[(3R,5R)-1-azabicyclo[3.2.1]oct-3-yl]thiophene-2-carboxamide;
5-(3-aminophenyl)-N-[(3R,5R)-1-azabicyclo[3.2.1]oct-3-yl]thiophene-2-carboxamide;
5-(4-aminophenyl)-N-[(3R,5R)-1-azabicyclo[3.2.1]oct-3-yl]thiophene-2-carboxamide;
5-(2-acetylaminophenyl)-N-[(3R,5R)-1-azabicyclo[3.2.1]oct-3-yl]thiophene-2-carboxamide;
5-(3-acetylaminophenyl)-N-[(3R,5R)-1-azabicyclo[3.2.1]oct-3-yl]thiophene-2-carboxamide;
5-(4-acetylaminophenyl)-N-[(3R,5R)-1-azabicyclo[3.2.1]oct-3-yl]thiophene-2-carboxamide;
N-[(3R,5R)-1-azabicyclo[3.2.1]oct-3-yl]-5-(2-trifluoroacetamidophenyl)thiophene-2-carboxamide;
N-[(3R,5R)-1-azabicyclo[3.2.1]oct-3-yl]-5-(3-trifluoroacetamidophenyl)thiophene-2-carboxamide;
N-[(3R,5R)-1-azabicyclo[3.2.1]oct-3-yl]-5-(4-trifluoroacetamidophenyl)thiophene-2-carboxamide;
N-[(3R,5R)-1-azabicyclo[3.2.1]oct-3-yl]-5-bromo-2-furamide;
N-[(3R,5R)-1-azabicyclo[3.2.1]oct-3-yl]-5-chloro-2-furamide;
N-[(3R,5R)-1-azabicyclo[3.2.1]oct-3-yl]-5-methyl-2-furamide;
N-[(3R,5R)-1-azabicyclo[3.2.1]oct-3-yl]-5-(3-fluorophenyl)-2-furamide;
N-[(3R,5R)-1-azabicyclo[3.2.1]oct-3-yl]-5-(4-fluorophenyl)-2-furamide;
N-[(3R,5R)-1-azabicyclo[3.2.1]oct-3-yl]-5-(2-chlorophenyl)-2-furamide;
N-[(3R,5R)-1-azabicyclo[3.2.1]oct-3-yl]-5-(3-chlorophenyl)-2-furamide;
N-[(3R,5R)-1-azabicyclo[3.2.1]oct-3-yl]-5-(4-chlorophenyl)-2-furamide;

N-[(3R,5R)-1-azabicyclo[3.2.1]oct-3-yl]-5-(2-methoxyphenyl)-2-furamide;
N-[(3R,5R)-1-azabicyclo[3.2.1]oct-3-yl]-5-(3-methoxyphenyl)-2-furamide;
N-[(3R,5R)-1-azabicyclo[3.2.1]oct-3-yl]-5-(4-methoxyphenyl)-2-furamide;
N-[(3R,5R)-1-azabicyclo[3.2.1]oct-3-yl]-5-(2-methylphenyl)-2-furamide;
N-[(3R,5R)-1-azabicyclo[3.2.1]oct-3-yl]-5-(3-methylphenyl)-2-furamide;
N-[(3R,5R)-1-azabicyclo[3.2.1]oct-3-yl]-5-(4-methylphenyl)-2-furamide;
N-[(3R,5R)-1-azabicyclo[3.2.1]oct-3-yl]-5-(2-hydroxyphenyl)-2-furamide;
N-[(3R,5R)-1-azabicyclo[3.2.1]oct-3-yl]-5-(3-hydroxyphenyl)-2-furamide;
N-[(3R,5R)-1-azabicyclo[3.2.1]oct-3-yl]-5-(4-hydroxyphenyl)-2-furamide;
5-(2-aminophenyl)-N-[(3R,5R)-1-azabicyclo[3.2.1]oct-3-yl]-2-furamide;
5-(3-aminophenyl)-N-[(3R,5R)-1-azabicyclo[3.2.1]oct-3-yl]-2-furamide;
5-(4-aminophenyl)-N-[(3R,5R)-1-azabicyclo[3.2.1]oct-3-yl]-2-furamide;
5-(2-acetylaminophenyl)-N-[(3R,5R)-1-azabicyclo[3.2.1]oct-3-yl]-2-furamide;
5-(3-acetylaminophenyl)-N-[(3R,5R)-1-azabicyclo[3.2.1]oct-3-yl]-2-furamide;
5-(4-acetylaminophenyl)-N-[(3R,5R)-1-azabicyclo[3.2.1]oct-3-yl]-2-furamide;
N-[(3R,5R)-1-azabicyclo[3.2.1]oct-3-yl]-5-(2-trifluoroacetamidophenyl)-2-furamide;
N-[(3R,5R)-1-azabicyclo[3.2.1]oct-3-yl]-5-(3-trifluoroacetamidophenyl)-2-furamide;
N-[(3R,5R)-1-azabicyclo[3.2.1]oct-3-yl]-5-(4-trifluoroacetamidophenyl)-2-furamide;
N-[(3R,5R)-1-azabicyclo[3.2.1]oct-3-yl]-5-bromo-1,3-thiazole-2-carboxamide;
N-[(3R,5R)-1-azabicyclo[3.2.1]oct-3-yl]-5-chloro-1,3-thiazole-2-carboxamide;
N-[(3R,5R)-1-azabicyclo[3.2.1]oct-3-yl]-5-methyl-1,3-thiazole-2-carboxamide;
N-[(3R,5R)-1-azabicyclo[3.2.1]oct-3-yl]-5-phenyl-1,3-thiazole-2-carboxamide;
N-[(3R,5R)-1-azabicyclo[3.2.1]oct-3-yl]-5-(2-fluorophenyl)-1,3-thiazole-2-carboxamide;
N-[(3R,5R)-1-azabicyclo[3.2.1]oct-3-yl]-5-(3-fluorophenyl)-1,3-thiazole-2-carboxamide;
N-[(3R,5R)-1-azabicyclo[3.2.1]oct-3-yl]-5-(4-fluorophenyl)-1,3-thiazole-2-carboxamide;
N-[(3R,5R)-1-azabicyclo[3.2.1]oct-3-yl]-5-(2-chlorophenyl)-1,3-thiazole-2-carboxamide;
N-[(3R,5R)-1-azabicyclo[3.2.1]oct-3-yl]-5-(3-chlorophenyl)-1,3-thiazole-2-carboxamide;
N-[(3R,5R)-1-azabicyclo[3.2.1]oct-3-yl]-5-(4-chlorophenyl)-1,3-thiazole-2-carboxamide;
N-[(3R,5R)-1-azabicyclo[3.2.1]oct-3-yl]-5-(2-methoxyphenyl)-1,3-thiazole-2-carboxamide;
N-[(3R,5R)-1-azabicyclo[3.2.1]oct-3-yl]-5-(3-methoxyphenyl)-1,3-thiazole-2-carboxamide;
N-[(3R,5R)-1-azabicyclo[3.2.1]oct-3-yl]-5-(4-methoxyphenyl)-1,3-thiazole-2-carboxamide;
N-[(3R,5R)-1-azabicyclo[3.2.1]oct-3-yl]-5-(2-methylphenyl)-1,3-thiazole-2-carboxamide;
N-[(3R,5R)-1-azabicyclo[3.2.1]oct-3-yl]-5-(3-methylphenyl)-1,3-thiazole-2-carboxamide;
N-[(3R,5R)-1-azabicyclo[3.2.1]oct-3-yl]-5-(4-methylphenyl)-1,3-thiazole-2-carboxamide;
N-[(3R,5R)-1-azabicyclo[3.2.1]oct-3-yl]-5-(2-hydroxyphenyl)-1,3-thiazole-2-carboxamide;
N-[(3R,5R)-1-azabicyclo[3.2.1]oct-3-yl]-5-(3-hydroxyphenyl)-1,3-thiazole-2-carboxamide;
N-[(3R,5R)-1-azabicyclo[3.2.1]oct-3-yl]-5-(4-hydroxyphenyl)-1,3-thiazole-2-carboxamide;
5-(2-aminophenyl)-N-[(3R,5R)-1-azabicyclo[3.2.1]oct-3-yl]-1,3-thiazole-2-carboxamide;
5-(3-aminophenyl)-N-[(3R,5R)-1-azabicyclo[3.2.1]oct-3-yl]-1,3-thiazole-2-carboxamide;
5-(4-aminophenyl)-N-[(3R,5R)-1-azabicyclo[3.2.1]oct-3-yl]-1,3-thiazole-2-carboxamide;
5-(2-acetylaminophenyl)-N-[(3R,5R)-1-azabicyclo[3.2.1]oct-3-yl]-1,3-thiazole-2-carboxamide;
5-(3-acetylaminophenyl)-N-[(3R,5R)-1-azabicyclo[3.2.1]oct-3-yl]-1,3-thiazole-2-carboxamide;
5-(4-acetylaminophenyl)-N-[(3R,5R)-1-azabicyclo[3.2.1]oct-3-yl]-1,3-thiazole-2-carboxamide;
N-[(3R,5R)-1-azabicyclo[3.2.1]oct-3-yl]-5-(2-trifluoroacetamidophenyl)-1,3-thiazole-2-carboxamide;
N-[(3R,5R)-1-azabicyclo[3.2.1]oct-3-yl]-5-(3-trifluoroacetamidophenyl)-1,3-thiazole-2-carboxamide;
N-[(3R,5R)-1-azabicyclo[3.2.1]oct-3-yl]-5-(4-trifluoroacetamidophenyl)-1,3-thiazole-2-carboxamide;
N-[(3R,5R)-1-azabicyclo[3.2.1]oct-3-yl]-5-bromo-1,3-oxazole-2-carboxamide;
N-[(3R,5R)-1-azabicyclo[3.2.1]oct-3-yl]-5-chloro-1,3-oxazole-2-carboxamide;
N-[(3R,5R)-1-azabicyclo[3.2.1]oct-3-yl]-5-methyl-1,3-oxazole-2-carboxamide;
N-[(3R,5R)-1-azabicyclo[3.2.1]oct-3-yl]-5-(2-fluorophenyl)-1,3-oxazole-2-carboxamide;
N-[(3R,5R)-1-azabicyclo[3.2.1]oct-3-yl]-5-(3-fluorophenyl)-1,3-oxazole-2-carboxamide;
N-[(3R,5R)-1-azabicyclo[3.2.1]oct-3-yl]-5-(4-fluorophenyl)-1,3-oxazole-2-carboxamide;
N-[(3R,5R)-1-azabicyclo[3.2.1]oct-3-yl]-5-(2-chlorophenyl)-1,3-oxazole-2-carboxamide;
N-[(3R,5R)-1-azabicyclo[3.2.1]oct-3-yl]-5-(3-chlorophenyl)-1,3-oxazole-2-carboxamide;
N-[(3R,5R)-1-azabicyclo[3.2.1]oct-3-yl]-5-(4-chlorophenyl)-1,3-oxazole-2-carboxamide;
N-[(3R,5R)-1-azabicyclo[3.2.1]oct-3-yl]-5-(2-methoxyphenyl)-1,3-oxazole-2-carboxamide;
N-[(3R,5R)-1-azabicyclo[3.2.1]oct-3-yl]-5-(3-methoxyphenyl)-1,3-oxazole-2-carboxamide;
N-[(3R,5R)-1-azabicyclo[3.2.1]oct-3-yl]-5-(4-methoxyphenyl)-1,3-oxazole-2-carboxamide;
N-[(3R,5R)-1-azabicyclo[3.2.1]oct-3-yl]-5-(2-methylphenyl)-1,3-oxazole-2-carboxamide;
N-[(3R,5R)-1-azabicyclo[3.2.1]oct-3-yl]-5-(3-methylphenyl)-1,3-oxazole-2-carboxamide;
N-[(3R,5R)-1-azabicyclo[3.2.1]oct-3-yl]-5-(4-methylphenyl)-1,3-oxazole-2-carboxamide;
N-[(3R,5R)-1-azabicyclo[3.2.1]oct-3-yl]-5-(2-hydroxyphenyl)-1,3-oxazole-2-carboxamide;
N-[(3R,5R)-1-azabicyclo[3.2.1]oct-3-yl]-5-(3-hydroxyphenyl)-1,3-oxazole-2-carboxamide;
N-[(3R,5R)-1-azabicyclo[3.2.1]oct-3-yl]-5-(4-hydroxyphenyl)-1,3-oxazole-2-carboxamide;
5-(2-aminophenyl)-N-[(3R,5R)-1-azabicyclo[3.2.1]oct-3-yl]-1,3-oxazole-2-carboxamide;
5-(3-aminophenyl)-N-[(3R,5R)-1-azabicyclo[3.2.1]oct-3-yl]-1,3-oxazole-2-carboxamide;
5-(2-acetylaminophenyl)-N-[(3R,5R)-1-azabicyclo[3.2.1]oct-3-yl]-1,3-oxazole-2-carboxamide;
5-(3-acetylaminophenyl)-N-[(3R,5R)-1-azabicyclo[3.2.1]oct-3-yl]-1,3-oxazole-2-carboxamide;

N-[(3R,5R)-1-azabicyclo[3.2.1]oct-3-yl]-5-(2-trifluoroacetamidophenyl)-1,3-oxazole-2-carboxamide;
N-[(3R,5R)-1-azabicyclo[3.2.1]oct-3-yl]-5-(3-trifluoroacetamidophenyl)-1,3-oxazole-2-carboxamide;
N-[(3R,5R)-1-azabicyclo[3.2.1]oct-3-yl]-5-(4-trifluoroacetamidophenyl)-1,3-oxazole-2-carboxamide;
N-[(3R,5R)-1-azabicyclo[3.2.1]oct-3-yl]-5-phenyl-1H-pyrrole-2-carboxamide; or
N-[(3R,5R)-1-azabicyclo[3.2.1]oct-3-yl]-5-phenyl-1-methyl-1H-pyrrole-2-carboxamide.

Another embodiment of the present invention includes any one or more of the following compounds as the free base or a pharmaceutically acceptable salt there of and as the pure enantiomer or as a racemic mixture thereof:

N-[(exo-4(S))-1-azabicyclo[2.2.1]hept-3-yl]-5-chlorothiophene-2-carboxamide;
N-[(exo-4(S))-1-azabicyclo[2.2.1]hept-3-yl]-5-methylthiophene-2-carboxamide;
N-[(exo-4(S))-1-azabicyclo[2.2.1]hept-3-yl]-5-(2-fluorophenyl)thiophene-2-carboxamide;
N-[(exo-4(S))-1-azabicyclo[2.2.1]hept-3-yl]-5-(3-fluorophenyl)thiophene-2-carboxamide;
N-[(exo-4(S))-1-azabicyclo[2.2.1]hept-3-yl]-5-(4-fluorophenyl)thiophene-2-carboxamide;
N-[(exo-4(S))-1-azabicyclo[2.2.1]hept-3-yl]-5-(2-chlorophenyl)thiophene-2-carboxamide;
N-[(exo-4(S))-1-azabicyclo[2.2.1]hept-3-yl]-5-(3-chlorophenyl)thiophene-2-carboxamide;
N-[(exo-4(S))-1-azabicyclo[2.2.1]hept-3-yl]-5-(4-chlorophenyl)thiophene-2-carboxamide;
N-[(exo-4(S))-1-azabicyclo[2.2.1]hept-3-yl]-5-(2-methoxyphenyl)thiophene-2-carboxamide;
N-[(exo-4(S))-1-azabicyclo[2.2.1]hept-3-yl]-5-(3-methoxyphenyl)thiophene-2-carboxamide;
N-[(exo-4(S))-1-azabicyclo[2.2.1]hept-3-yl]-5-(4-methoxyphenyl)thiophene-2-carboxamide;
N-[(exo-4(S))-1-azabicyclo[2.2.1]hept-3-yl]-5-(2-methylphenyl)thiophene-2-carboxamide;
N-[(exo-4(S))-1-azabicyclo[2.2.1]hept-3-yl]-5-(3-methylphenyl)thiophene-2-carboxamide;
N-[(exo-4(S))-1-azabicyclo[2.2.1]hept-3-yl]-5-(4-methylphenyl)thiophene-2-carboxamide;
N-[(exo-4(S))-1-azabicyclo[2.2.1]hept-3-yl]-5-(2-hydroxyphenyl)thiophene-2-carboxamide;
N-[(exo-4(S))-1-azabicyclo[2.2.1]hept-3-yl]-5-(3-hydroxyphenyl)thiophene-2-carboxamide;
N-[(exo-4(S))-1-azabicyclo[2.2.1]hept-3-yl]-5-(4-hydroxyphenyl)thiophene-2-carboxamide;
5-(2-aminophenyl)-N-[(exo-4(S))-1-azabicyclo[2.2.1]hept-3-yl]thiophene-2-carboxamide;
5-(3-aminophenyl)-N-[(exo-4(S))-1-azabicyclo[2.2.1]hept-3-yl]thiophene-2-carboxamide;
5-(4-aminophenyl)-N-[(exo-4(S))-1-azabicyclo[2.2.1]hept-3-yl]thiophene-2-carboxamide;
5-(2-acetylaminophenyl)-N-[(exo-4(S))-1-azabicyclo[2.2.1]hept-3-yl]thiophene-2-carboxamide;
5-(3-acetylaminophenyl)-N-[(exo-4(S))-1-azabicyclo[2.2.1]hept-3-yl]thiophene-2-carboxamide;
5-(4-acetylaminophenyl)-N-[(exo-4(S))-1-azabicyclo[2.2.1]hept-3-yl]thiophene-2-carboxamide;
N-[(exo-4(S))-1-azabicyclo[2.2.1]hept-3-yl]-5-(2-trifluoroacetamidophenyl)thiophene-2-carboxamide;
N-[(exo-4(S))-1-azabicyclo[2.2.1]hept-3-yl]-5-(3-trifluoroacetamidophenyl)thiophene-2-carboxamide;
N-[(exo-4(S))-1-azabicyclo[2.2.1]hept-3-yl]-5-(4-trifluoroacetamidophenyl)thiophene-2-carboxamide;
N-[(exo-4(S))-1-azabicyclo[2.2.1]hept-3-yl]-5-bromo-2-furamide;
N-[(exo-4(S))-1-azabicyclo[2.2.1]hept-3-yl]-5-chloro-2-furamide;
N-[(exo-4(S))-1-azabicyclo[2.2.1]hept-3-yl]-5-methyl-2-furamide;
N-[(exo-4(S))-1-azabicyclo[2.2.1]hept-3-yl]-5-(2-chlorophenyl)-2-furamide;
N-[(exo-4(S))-1-azabicyclo[2.2.1]hept-3-yl]-5-(3-chlorophenyl)-2-furamide;
N-[(exo-4(S))-1-azabicyclo[2.2.1]hept-3-yl]-5-(4-chlorophenyl)-2-furamide;
N-[(exo-4(S))-1-azabicyclo[2.2.1]hept-3-yl]-5-(2-methoxyphenyl)-2-furamide;
N-[(exo-4(S))-1-azabicyclo[2.2.1]hept-3-yl]-5-(3-methoxyphenyl)-2-furamide;
N-[(exo-4(S))-1-azabicyclo[2.2.1]hept-3-yl]-5-(4-methoxyphenyl)-2-furamide;
N-[(exo-4(S))-1-azabicyclo[2.2.1]hept-3-yl]-5-(2-methylphenyl)-2-furamide;
N-[(exo-4(S))-1-azabicyclo[2.2.1]hept-3-yl]-5-(3-methylphenyl)-2-furamide;
N-[(exo-4(S))-1-azabicyclo[2.2.1]hept-3-yl]-5-(2-hydroxyphenyl)-2-furamide;
N-[(exo-4(S))-1-azabicyclo[2.2.1]hept-3-yl]-5-(3-hydroxyphenyl)-2-furamide;
N-[(exo-4(S))-1-azabicyclo[2.2.1]hept-3-yl]-5-(4-hydroxyphenyl)-2-furamide;
5-(2-aminophenyl)-N-[(exo-4(S))-1-azabicyclo[2.2.1]hept-3-yl]-2-furamide;
5-(3-aminophenyl)-N-[(exo-4(S))-1-azabicyclo[2.2.1]hept-3-yl]-2-furamide;
5-(4-aminophenyl)-N-[(exo-4(S))-1-azabicyclo[2.2.1]hept-3-yl]-2-furamide;
5-(2-acetylaminophenyl)-N-[(exo-4(S))-1-azabicyclo[2.2.1]hept-3-yl]-2-furamide;
5-(3-acetylaminophenyl)-N-[(exo-4(S))-1-azabicyclo[2.2.1]hept-3-yl]-2-furamide;
5-(4-acetylaminophenyl)-N-[(exo-4(S))-1-azabicyclo[2.2.1]hept-3-yl]-2-furamide;
N-[(exo-4(S))-1-azabicyclo[2.2.1]hept-3-yl]-5-(2-trifluoroacetamidophenyl)-2-furamide;
N-[(exo-4(S))-1-azabicyclo[2.2.1]hept-3-yl]-5-(3-trifluoroacetamidophenyl)-2-furamide;
N-[(exo-4(S))-1-azabicyclo[2.2.1]hept-3-yl]-5-(4-trifluoroacetamidophenyl)-2-furamide;
N-[(exo-4(S))-1-azabicyclo[2.2.1]hept-3-yl]-5-bromo-1,3-thiazole-2-carboxamide;
N-[(exo-4(S))-1-azabicyclo[2.2.1]hept-3-yl]-5-chloro-1,3-thiazole-2-carboxamide;
N-[(exo-4(S))-1-azabicyclo[2.2.1]hept-3-yl]-5-methyl-1,3-thiazole-2-carboxamide;
N-[(exo-4(S))-1-azabicyclo[2.2.1]hept-3-yl]-5-phenyl-1,3-thiazole-2-carboxamide;
N-[(exo-4(S))-1-azabicyclo[2.2.1]hept-3-yl]-5-(2-fluorophenyl)-1,3-thiazole-2-carboxamide;
N-[(exo-4(S))-1-azabicyclo[2.2.1]hept-3-yl]-5-(3-fluorophenyl)-1,3-thiazole-2-carboxamide;
N-[(exo-4(S))-1-azabicyclo[2.2.1]hept-3-yl]-5-(4-fluorophenyl)-1,3-thiazole-2-carboxamide;
N-[(exo-4(S))-1-azabicyclo[2.2.1]hept-3-yl]-5-(2-chlorophenyl)-1,3-thiazole-2-carboxamide;
N-[(exo-4(S))-1-azabicyclo[2.2.1]hept-3-yl]-5-(3-chlorophenyl)-1,3-thiazole-2-carboxamide;
N-[(exo-4(S))-1-azabicyclo[2.2.1]hept-3-yl]-5-(4-chlorophenyl)-1,3-thiazole-2-carboxamide;
N-[(exo-4(S))-1-azabicyclo[2.2.1]hept-3-yl]-5-(2-methoxyphenyl)-1,3-thiazole-2-carboxamide;
N-[(exo-4(S))-1-azabicyclo[2.2.1]hept-3-yl]-5-(3-methoxyphenyl)-1,3-thiazole-2-carboxamide;

N-[(exo-4(S))-1-azabicyclo[2.2.1]hept-3-yl]-5-(4-methoxyphenyl)-1,3-thiazole-2-carboxamide;
N-[(exo-4(S))-1-azabicyclo[2.2.1]hept-3-yl]-5-(2-methylphenyl)-1,3-thiazole-2-carboxamide;
N-[(exo-4(S))-1-azabicyclo[2.2.1]hept-3-yl]-5-(3-methylphenyl)-1,3-thiazole-2-carboxamide;
N-[(exo-4(S))-1-azabicyclo[2.2.1]hept-3-yl]-5-(4-methylphenyl)-1,3-thiazole-2-carboxamide;
N-[(exo-4(S))-1-azabicyclo[2.2.1]hept-3-yl]-5-(2-hydroxyphenyl)-1,3-thiazole-2-carboxamide;
N-[(exo-4(S))-1-azabicyclo[2.2.1]hept-3-yl]-5-(3-hydroxyphenyl)-1,3-thiazole-2-carboxamide;
N-[(exo-4(S))-1-azabicyclo[2.2.1]hept-3-yl]-5-(4-hydroxyphenyl)-1,3-thiazole-2-carboxamide;
5-(2-aminophenyl)-N-[(exo-4(S))-1-azabicyclo[2.2.1]hept-3-yl]-1,3-thiazole-2-carboxamide;
5-(3-aminophenyl)-N-[(exo-4(S))-1-azabicyclo[2.2.1]hept-3-yl]-1,3-thiazole-2-carboxamide;
5-(4-aminophenyl)-N-[(exo-4(S))-1-azabicyclo[2.2.1]hept-3-yl]-1,3-thiazole-2-carboxamide;
5-(2-acetylaminophenyl)-N-[(exo-4(S))-1-azabicyclo[2.2.1]hept-3-yl]-1,3-thiazole-2-carboxamide;
5-(3-acetylaminophenyl)-N-[(exo-4(S))-1-azabicyclo[2.2.1]hept-3-yl]-1,3-thiazole-2-carboxamide;
5-(4-acetylaminophenyl)-N-[(exo-4(S))-1-azabicyclo[2.2.1]hept-3-yl]-1,3-thiazole-2-carboxamide;
N-[(exo-4(S))-1-azabicyclo[2.2.1]hept-3-yl]-5-(2-trifluoroacetamidophenyl)-1,3-thiazole-2-carboxamide;
N-[(exo-4(S))-1-azabicyclo[2.2.1]hept-3-yl]-5-(3-trifluoroacetamidophenyl)-1,3-thiazole-2-carboxamide;
N-[(exo-4(S))-1-azabicyclo[2.2.1]hept-3-yl]-5-(4-trifluoroacetamidophenyl)-1,3-thiazole-2-carboxamide;
N-[(exo-4(S))-1-azabicyclo[2.2.1]hept-3-yl]-5-bromo-1,3-oxazole-2-carboxamide;
N-[(exo-4(S))-1-azabicyclo[2.2.1]hept-3-yl]-5-chloro-1,3-oxazole-2-carboxamide;
N-[(exo-4(S))-1-azabicyclo[2.2.1]hept-3-yl]-5-methyl-1,3-oxazole-2-carboxamide;
N-[(exo-4(S))-1-azabicyclo[2.2.1]hept-3-yl]-5-(2-fluorophenyl)-1,3-oxazole-2-carboxamide;
N-[(exo-4(S))-1-azabicyclo[2.2.1]hept-3-yl]-5-(3-fluorophenyl)-1,3-oxazole-2-carboxamide;
N-[(exo-4(S))-1-azabicyclo[2.2.1]hept-3-yl]-5-(4-fluorophenyl)-1,3-oxazole-2-carboxamide;
N-[(exo-4(S))-1-azabicyclo[2.2.1]hept-3-yl]-5-(2-chlorophenyl)-1,3-oxazole-2-carboxamide;
N-[(exo-4(S))-1-azabicyclo[2.2.1]hept-3-yl]-5-(3-chlorophenyl)-1,3-oxazole-2-carboxamide;
N-[(exo-4(S))-1-azabicyclo[2.2.1]hept-3-yl]-5-(4-chlorophenyl)-1,3-oxazole-2-carboxamide;
N-[(exo-4(S))-1-azabicyclo[2.2.1]hept-3-yl]-5-(2-methoxyphenyl)-1,3-oxazole-2-carboxamide;
N-[(exo-4(S))-1-azabicyclo[2.2.1]hept-3-yl]-5-(3-methoxyphenyl)-1,3-oxazole-2-carboxamide;
N-[(exo-4(S))-1-azabicyclo[2.2.1]hept-3-yl]-5-(4-methoxyphenyl)-1,3-oxazole-2-carboxamide;
N-[(exo-4(S))-1-azabicyclo[2.2.1]hept-3-yl]-5-(2-methylphenyl)-1,3-oxazole-2-carboxamide;
N-[(exo-4(S))-1-azabicyclo[2.2.1]hept-3-yl]-5-(3-methylphenyl)-1,3-oxazole-2-carboxamide;
N-[(exo-4(S))-1-azabicyclo[2.2.1]hept-3-yl]-5-(4-methylphenyl)-1,3-oxazole-2-carboxamide;
N-[(exo-4(S))-1-azabicyclo[2.2.1]hept-3-yl]-5-(2-hydroxyphenyl)-1,3-oxazole-2-carboxamide;
N-[(exo-4(S))-1-azabicyclo[2.2.1]hept-3-yl]-5-(3-hydroxyphenyl)-1,3-oxazole-2-carboxamide;
N-[(exo-4(S))-1-azabicyclo[2.2.1]hept-3-yl]-5-(4-hydroxyphenyl)-1,3-oxazole-2-carboxamide;
5-(2-aminophenyl)-N-[(exo-4(S))-1-azabicyclo[2.2.1]hept-3-yl]-1,3-oxazole-2-carboxamide;
5-(3-aminophenyl)-N-[(exo-4(S))-1-azabicyclo[2.2.1]hept-3-yl]-1,3-oxazole-2-carboxamide;
5-(4-aminophenyl)-N-[(exo-4(S))-1-azabicyclo[2.2.1]hept-3-yl]-1,3-oxazole-2-carboxamide;
5-(2-acetylaminophenyl)-N-[(exo-4(S))-1-azabicyclo[2.2.1]hept-3-yl]-1,3-oxazole-2-carboxamide;
5-(3-acetylaminophenyl)-N-[(exo-4(S))-1-azabicyclo[2.2.1]hept-3-yl]-1,3-oxazole-2-carboxamide;
5-(4-acetylaminophenyl)-N-[(exo-4(S))-1-azabicyclo[2.2.1]hept-3-yl]-1,3-oxazole-2-carboxamide;
N-[(exo-4(S))-1-azabicyclo[2.2.1]hept-3-yl]-5-(2-trifluoroacetamidophenyl)-1,3-oxazole-2-carboxamide;
N-[(exo-4(S))-1-azabicyclo[2.2.1]hept-3-yl]-5-(3-trifluoroacetamidophenyl)-1,3-oxazole-2-carboxamide;
N-[(exo-4(S))-1-azabicyclo[2.2.1]hept-3-yl]-5-(4-trifluoroacetamidophenyl)-1,3-oxazole-2-carboxamide;
N-[(exo-4(S))-1-azabicyclo[2.2.1]hept-3-yl]-5-phenyl-1H-pyrrole-2-carboxamide; or
N-[(exo-4(S))-1-azabicyclo[2.2.1]hept-3-yl]-5-phenyl-1-methyl-1H-pyrrole-2-carboxamide.

Another embodiment of the present invention includes any one or more of the following compounds as the free base or a pharmaceutically acceptable salt there of and as the pure enantiomer or as a racemic mixture thereof:
N-[(3R)-6-methyl-1-azabicyclo[2.2.2]oct-3-yl]-5-bromothiophene-2-carboxamide;
N-[(3R)-6-methyl-1-azabicyclo[2.2.2]oct-3-yl]-5-chlorothiophene-2-carboxamide;
N-[(3R)-6-methyl-1-azabicyclo[2.2.2]oct-3-yl]-5-methylthiophene-2-carboxamide;
N-[(3R)-6-methyl-1-azabicyclo[2.2.2]oct-3-yl]-5-phenylthiophene-2-carboxamide;
N-[(3R)-6-methyl-1-azabicyclo[2.2.2]oct-3-yl]-5-(2-fluorophenyl)thiophene-2-carboxamide;
N-[(3R)-6-methyl-1-azabicyclo[2.2.2]oct-3-yl]-5-(3-fluorophenyl)thiophene-2-carboxamide;
N-[(3R)-6-methyl-1-azabicyclo[2.2.2]oct-3-yl]-5-(4-fluorophenyl)thiophene-2-carboxamide;
N-[(3R)-6-methyl-1-azabicyclo[2.2.2]oct-3-yl]-5-(2-chlorophenyl)thiophene-2-carboxamide;
N-[(3R)-6-methyl-1-azabicyclo[2.2.2]oct-3-yl]-5-(3-chlorophenyl)thiophene-2-carboxamide;
N-[(3R)-6-methyl-1-azabicyclo[2.2.2]oct-3-yl]-5-(4-chlorophenyl)thiophene-2-carboxamide;
N-[(3R)-6-methyl-1-azabicyclo[2.2.2]oct-3-yl]-5-(2-methoxyphenyl)thiophene-2-carboxamide;
N-[(3R)-6-methyl-1-azabicyclo[2.2.2]oct-3-yl]-5-(3-methoxyphenyl)thiophene-2-carboxamide;
N-[(3R)-6-methyl-1-azabicyclo[2.2.2]oct-3-yl]-5-(4-methoxyphenyl)thiophene-2-carboxamide;
N-[(3R)-6-methyl-1-azabicyclo[2.2.2]oct-3-yl]-5-(2-methylphenyl)thiophene-2-carboxamide;
N-[(3R)-6-methyl-1-azabicyclo[2.2.2]oct-3-yl]-5-(3-methylphenyl)thiophene-2-carboxamide;
N-[(3R)-6-methyl-1-azabicyclo[2.2.2]oct-3-yl]-5-(4-methylphenyl)thiophene-2-carboxamide;
N-[(3R)-6-methyl-1-azabicyclo[2.2.2]oct-3-yl]-5-(2-hydroxyphenyl)thiophene-2-carboxamide;
N-[(3R)-6-methyl-1-azabicyclo[2.2.2]oct-3-yl]-5-(3-hydroxyphenyl)thiophene-2-carboxamide;
N-[(3R)-6-methyl-1-azabicyclo[2.2.2]oct-3-yl]-5-(4-hydroxyphenyl)thiophene-2-carboxamide;
5-(2-aminophenyl)-N-[(3R)-6-methyl-1-azabicyclo[2.2.2]oct-3-yl]thiophene-2-carboxamide;
5-(3-aminophenyl)-N-[(3R)-6-methyl-1-azabicyclo[2.2.2]oct-3-yl]thiophene-2-carboxamide;

5-(4-aminophenyl)-N-[(3R)-6-methyl-1-azabicyclo[2.2.2]oct-3-yl]thiophene-2-carboxamide;
5-(2-acetylaminophenyl)-N-[(3R)-6-methyl-1-azabicyclo[2.2.2]oct-3-yl]thiophene-2-carboxamide;
5-(3-acetylaminophenyl)-N-[(3R)-6-methyl-1-azabicyclo[2.2.2]oct-3-yl]thiophene-2-carboxamide;
5-(4-acetylaminophenyl)-N-[(3R)-6-methyl-1-azabicyclo[2.2.2]oct-3-yl]thiophene-2-carboxamide;
N-[(3R)-6-methyl-1-azabicyclo[2.2.2]oct-3-yl]-5-(2-trifluoroacetamidophenyl)thiophene-2-carboxamide;
N-[(3R)-6-methyl-1-azabicyclo[2.2.2]oct-3-yl]-5-(3-trifluoroacetamidophenyl)thiophene-2-carboxamide;
N-[(3R)-6-methyl-1-azabicyclo[2.2.2]oct-3-yl]-5-(4-trifluoroacetamidophenyl)thiophene-2-carboxamide;
N-[(3R)-6-methyl-1-azabicyclo[2.2.2]oct-3-yl]-5-bromo-2-furamide;
N-[(3R)-6-methyl-1-azabicyclo[2.2.2]oct-3-yl]-5-chloro-2-furamide;
N-[(3R)-6-methyl-1-azabicyclo[2.2.2]oct-3-yl]-5-methyl-2-furamide;
N-[(3R)-6-methyl-1-azabicyclo[2.2.2]oct-3-yl]-5-phenyl-2-furamide;
N-[(3R)-6-methyl-1-azabicyclo[2.2.2]oct-3-yl]-5-(2-fluorophenyl)-2-furamide;
N-[(3R)-6-methyl-1-azabicyclo[2.2.2]oct-3-yl]-5-(3-fluorophenyl)-2-furamide;
N-[(3R)-6-methyl-1-azabicyclo[2.2.2]oct-3-yl]-5-(4-fluorophenyl)-2-furamide;
N-[(3R)-6-methyl-1-azabicyclo[2.2.2]oct-3-yl]-5-(2-chlorophenyl)-2-furamide;
N-[(3R)-6-methyl-1-azabicyclo[2.2.2]oct-3-yl]-5-(3-chlorophenyl)-2-furamide;
N-[(3R)-6-methyl-1-azabicyclo[2.2.2]oct-3-yl]-5-(4-chlorophenyl)-2-furamide;
N-[(3R)-6-methyl-1-azabicyclo[2.2.2]oct-3-yl]-5-(2-methoxyphenyl)-2-furamide;
N-[(3R)-6-methyl-1-azabicyclo[2.2.2]oct-3-yl]-5-(3-methoxyphenyl)-2-furamide;
N-[(3R)-6-methyl-1-azabicyclo[2.2.2]oct-3-yl]-5-(4-methoxyphenyl)-2-furamide;
N-[(3R)-6-methyl-1-azabicyclo[2.2.2]oct-3-yl]-5-(2-methylphenyl)-2-furamide;
N-[(3R)-6-methyl-1-azabicyclo[2.2.2]oct-3-yl]-5-(3-methylphenyl)-2-furamide;
N-[(3R)-6-methyl-1-azabicyclo[2.2.2]oct-3-yl]-5-(4-methylphenyl)-2-furamide;
N-[(3R)-6-methyl-1-azabicyclo[2.2.2]oct-3-yl]-5-(2-hydroxyphenyl)-2-furamide;
N-[(3R)-6-methyl-1-azabicyclo[2.2.2]oct-3-yl]-5-(3-hydroxyphenyl)-2-furamide;
N-[(3R)-6-methyl-1-azabicyclo[2.2.2]oct-3-yl]-5-(4-hydroxyphenyl)-2-furamide;
5-(2-aminophenyl)-N-[(3R)-6-methyl-1-azabicyclo[2.2.2]oct-3-yl]-2-furamide;
5-(3-aminophenyl)-N-[(3R)-6-methyl-1-azabicyclo[2.2.2]oct-3-yl]-2-furamide;
5-(4-aminophenyl)-N-[(3R)-6-methyl-1-azabicyclo[2.2.2]oct-3-yl]-2-furamide;
5-(2-acetylaminophenyl)-N-[(3R)-6-methyl-1-azabicyclo[2.2.2]oct-3-yl]-2-furamide;
5-(3-acetylaminophenyl)-N-[(3R)-6-methyl-1-azabicyclo[2.2.2]oct-3-yl]-2-furamide;
5-(4-acetylaminophenyl)-N-[(3R)-6-methyl-1-azabicyclo[2.2.2]oct-3-yl]-2-furamide;
N-[(3R)-6-methyl-1-azabicyclo[2.2.2]oct-3-yl]-5-(2-trifluoroacetamidophenyl)-2-furamide;
N-[(3R)-6-methyl-1-azabicyclo[2.2.2]oct-3-yl]-5-(3-trifluoroacetamidophenyl)-2-furamide;
N-[(3R)-6-methyl-1-azabicyclo[2.2.2]oct-3-yl]-5-(4-trifluoroacetamidophenyl)-2-furamide;
N-[(3R)-6-methyl-1-azabicyclo[2.2.2]oct-3-yl]-5-bromo-1,3-thiazole-2-carboxamide;
N-[(3R)-6-methyl-1-azabicyclo[2.2.2]oct-3-yl]-5-chloro-1,3-thiazole-2-carboxamide;
N-[(3R)-6-methyl-1-azabicyclo[2.2.2]oct-3-yl]-5-methyl-1,3-thiazole-2-carboxamide;
N-[(3R)-6-methyl-1-azabicyclo[2.2.2]oct-3-yl]-5-phenyl-1,3-thiazole-2-carboxamide;
N-[(3R)-6-methyl-1-azabicyclo[2.2.2]oct-3-yl]-5-(2-fluorophenyl)-1,3-thiazole-2-carboxamide;
N-[(3R)-6-methyl-1-azabicyclo[2.2.2]oct-3-yl]-5-(3-fluorophenyl)-1,3-thiazole-2-carboxamide;
N-[(3R)-6-methyl-1-azabicyclo[2.2.2]oct-3-yl]-5-(4-fluorophenyl)-1,3-thiazole-2-carboxamide;
N-[(3R)-6-methyl-1-azabicyclo[2.2.2]oct-3-yl]-5-(2-chlorophenyl)-1,3-thiazole-2-carboxamide;
N-[(3R)-6-methyl-1-azabicyclo[2.2.2]oct-3-yl]-5-(3-chlorophenyl)-1,3-thiazole-2-carboxamide;
N-[(3R)-6-methyl-1-azabicyclo[2.2.2]oct-3-yl]-5-(4-chlorophenyl)-1,3-thiazole-2-carboxamide;
N-[(3R)-6-methyl-1-azabicyclo[2.2.2]oct-3-yl]-5-(2-methoxyphenyl)-1,3-thiazole-2-carboxamide;
N-[(3R)-6-methyl-1-azabicyclo[2.2.2]oct-3-yl]-5-(3-methoxyphenyl)-1,3-thiazole-2-carboxamide;
N-[(3R)-6-methyl-1-azabicyclo[2.2.2]oct-3-yl]-5-(4-methoxyphenyl)-1,3-thiazole-2-carboxamide;
N-[(3R)-6-methyl-1-azabicyclo[2.2.2]oct-3-yl]-5-(2-methylphenyl)-1,3-thiazole-2-carboxamide;
N-[(3R)-6-methyl-1-azabicyclo[2.2.2]oct-3-yl]-5-(3-methylphenyl)-1,3-thiazole-2-carboxamide;
N-[(3R)-6-methyl-1-azabicyclo[2.2.2]oct-3-yl]-5-(4-methylphenyl)-1,3-thiazole-2carboxamide;
N-[(3R)-6-methyl-1-azabicyclo[2.2.2]oct-3-yl]-5-(2-hydroxyphenyl)-1,3-thiazole-2-carboxamide;
N-[(3R)-6-methyl-1-azabicyclo[2.2.2]oct-3-yl]-5-(3-hydroxyphenyl)-1,3-thiazole-2-carboxamide;
N-[(3R)-6-methyl-1-azabicyclo[2.2.2]oct-3-yl]-5-(4-hydroxyphenyl)-1,3-thiazole-2-carboxamide;
5-(2-aminophenyl)-N-[(3R)-6-methyl-1-azabicyclo[2.2.2]oct-3-yl]-1,3-thiazole-2-carboxamide;
5-(3-aminophenyl)-N-[(3R)-6-methyl-1-azabicyclo[2.2.2]oct-3-yl]-1,3-thiazole-2-carboxamide;
5-(4-aminophenyl)-N-[(3R)-6-methyl-1-azabicyclo[2.2.2]oct-3-yl]-1,3-thiazole-2-carboxamide;
5-(2-acetylaminophenyl)-N-[(3R)-6-methyl-1-azabicyclo[2.2.2]oct-3-yl]-1,3-thiazole -2-carboxamide;
5-(3-acetylaminophenyl)-N-[(3R)-6-methyl-1-azabicyclo[2.2.2]oct-3-yl]-1,3-thiazole -2-carboxamide;
5-(4-acetylaminophenyl)-N-[(3R)-6-methyl-1-azabicyclo[2.2.2]oct-3-yl]-1,3-thiazole -2-carboxamide;
N-[(3R)-6-methyl-1-azabicyclo[2.2.2]oct-3-yl]-5-(2-trifluoroacetamidophenyl)-1,3-thiazole-2-carboxamide;
N-[(3R)-6-methyl-1-azabicyclo[2.2.2]oct-3-yl]-5-(3-trifluoroacetamidophenyl)-1,3-thiazole-2-carboxamide;
N-[(3R)-6-methyl-1-azabicyclo[2.2.2]oct-3-yl]-5-(4-trifluoroacetamidophenyl)-1,3-thiazole-2-carboxamide;
N-[(3R)-6-methyl-1-azabicyclo[2.2.2]oct-3-yl]-5-bromo-1,3-oxazole-2-carboxamide;
N-[(3R)-6-methyl-1-azabicyclo[2.2.2]oct-3-yl]-5-chloro-1,3-oxazole-2-carboxamide;
N-[(3R)-6-methyl-1-azabicyclo[2.2.2]oct-3-yl]-5-methyl-1,3-oxazole-2-carboxamide;
N-[(3R)-6-methyl-1-azabicyclo[2.2.2]oct-3-yl]-5-phenyl-1,3-oxazole-2-carboxamide;
N-[(3R)-6-methyl-1-azabicyclo[2.2.2]oct-3-yl]-5-(2-fluorophenyl)-1,3-oxazole-2-carboxamide;

N-[(3R)-6-methyl-1-azabicyclo[2.2.2]oct-3-yl]-5-(3-fluorophenyl)-1,3-oxazole-2-carboxamide;
N-[(3R)-6-methyl-1-azabicyclo[2.2.2]oct-3-yl]-5-(4-fluorophenyl)-1,3-oxazole-2-carboxamide;
N-[(3R)-6-methyl-1-azabicyclo[2.2.2]oct-3-yl]-5-(2-chlorophenyl)-1,3-oxazole-2-carboxamide;
N-[(3R)-6-methyl-1-azabicyclo[2.2.2]oct-3-yl]-5-(3-chlorophenyl)-1,3-oxazole-2-carboxamide;
N-[(3R)-6-methyl-1-azabicyclo[2.2.2]oct-3-yl]-5-(4-chlorophenyl)-1,3-oxazole-2-carboxamide;
N-[(3R)-6-methyl-1-azabicyclo[2.2.2]oct-3-yl]-5-(2-methoxyphenyl)-1,3-oxazole-2-carboxamide;
N-[(3R)-6-methyl-1-azabicyclo[2.2.2]oct-3-yl]-5-(3-methoxyphenyl)-1,3-oxazole-2-carboxamide;
N-[(3R)-6-methyl-1-azabicyclo[2.2.2]oct-3-yl]-5-(4-methoxyphenyl)-1,3-oxazole-2-carboxamide;
N-[(3R)-6-methyl-1-azabicyclo[2.2.2]oct-3-yl]-5-(2-methylphenyl)-1,3-oxazole-2-carboxamide;
N-[(3R)-6-methyl-1-azabicyclo[2.2.2]oct-3-yl]-5-(3-methylphenyl)-1,3-oxazole-2-carboxamide;
N-[(3R)-6-methyl-1-azabicyclo[2.2.2]oct-3-yl]-5-(4-methylphenyl)-1,3-oxazole-2-carboxamide;
N-[(3R)-6-methyl-1-azabicyclo[2.2.2]oct-3-yl]-5-(2-hydroxyphenyl)-1,3-oxazole-2-carboxamide;
N-[(3R)-6-methyl-1-azabicyclo[2.2.2]oct-3-yl]-5-(3-hydroxyphenyl)-1,3-oxazole-2-carboxamide;
N-[(3R)-6-methyl-1-azabicyclo[2.2.2]oct-3-yl]-5-(4-hydroxyphenyl)-1,3-oxazole-2-carboxamide;
5-(2-aminophenyl)-N-[(3R)-6-methyl-1-azabicyclo[2.2.2]oct-3-yl]-1,3-oxazole-2-carboxamide;
5-(3-aminophenyl)-N-[(3R)-6-methyl-1-azabicyclo[2.2.2]oct-3-yl]-1,3-oxazole-2-carboxamide;
5-(4-aminophenyl)-N-[(3R)-6-methyl-1-azabicyclo[2.2.2]oct-3-yl]-1,3-oxazole-2-carboxamide;
5-(2-acetylaminophenyl)-N-[(3R)-6-methyl-1-azabicyclo[2.2.2]oct-3-yl]-1,3-oxazole-2-carboxamide;
5-(3-acetylaminophenyl)-N-[(3R)-6-methyl-1-azabicyclo[2.2.2]oct-3-yl]-1,3-oxazole-2-carboxamide;
5-(4-acetylaminophenyl)-N-[(3R)-6-methyl-1-azabicyclo[2.2.2]oct-3-yl]-1,3-oxazole-2-carboxamide;
N-[(3R)-6-methyl-1-azabicyclo[2.2.2]oct-3-yl]-5-(2-trifluoroacetamidophenyl)-1,3-oxazole-2-carboxamide;
N-[(3R)-6-methyl-1-azabicyclo[2.2.2]oct-3-yl]-5-(3-trifluoroacetamidophenyl)-1,3-oxazole-2-carboxamide;
N-[(3R)-6-methyl-1-azabicyclo[2.2.2]oct-3-yl]-5-(4-trifluoroacetamidophenyl)-1,3-oxazole-2-carboxamide;
N-[(3R)-6-methyl-1-azabicyclo[2.2.2]oct-3-yl]-5-phenyl-1H-pyrrole-2-carboxamide;
N-[(3R)-6-methyl-1-azabicyclo[2.2.2]oct-3-yl]-5-phenyl-1-methyl-1H-pyrrole-2-carboxamide; or
N-[(3R)-1-azabicyclo[3.2.2]non-3-yl]-5-phenyl-1,3-oxazole-2-carboxamide.

Another embodiment of the present invention includes any one or more of the following compounds as the free base or a pharmaceutically acceptable salt there of and as the pure enantiomer or as a racemic mixture thereof:
N-[2-azabicyclo[2.2.1]hept-5-yl]-5-bromothiophene-2-carboxamide;
N-[2-azabicyclo[2.2.1]hept-5-yl]-5-chlorothiophene-2-carboxamide;
N-[2-azabicyclo[2.2.1]hept-5-yl]-5-methylthiophene-2-carboxamide;
N-[2-azabicyclo[2.2.1]hept-5-yl]-5-phenylthiophene-2-carboxamide;
N-[2-azabicyclo[2.2.1]hept-5-yl]-5-(2-fluorophenyl)thiophene-2-carboxamide;
N-[2-azabicyclo[2.2.1]hept-5-yl]-5-(3-fluorophenyl)thiophene-2-carboxamide;
N-[2-azabicyclo[2.2.1]hept-5-yl]-5-(4-fluorophenyl)thiophene-2-carboxamide;
N-[2-azabicyclo[2.2.1]hept-5-yl]-5-(2-chlorophenyl)thiophene-2-carboxamide;
N-[2-azabicyclo[2.2.1]hept-5-yl]-5-(3-chlorophenyl)thiophene-2-carboxamide;
N-[2-azabicyclo[2.2.1]hept-5-yl]-5-(4-chlorophenyl)thiophene-2-carboxamide;
N-[2-azabicyclo[2.2.1]hept-5-yl]-5-(2-methoxyphenyl)thiophene-2-carboxamide;
N-[2-azabicyclo[2.2.1]hept-5-yl]-5-(3-methoxyphenyl)thiophene-2-carboxamide;
N-[2-azabicyclo[2.2.1]hept-5-yl]-5-(4-methoxyphenyl)thiophene-2-carboxamide;
N-[2-azabicyclo[2.2.1]hept-5-yl]-5-(2-methylphenyl)thiophene-2-carboxamide;
N-[2-azabicyclo[2.2.1]hept-5-yl]-5-(3-methylphenyl)thiophene-2-carboxamide;
N-[2-azabicyclo[2.2.1]hept-5-yl]-5-(4-methylphenyl)thiophene-2-carboxamide;
N-[2-azabicyclo[2.2.1]hept-5-yl]-5-(2-hydroxyphenyl)thiophene-2-carboxamide;
N-[2-azabicyclo[2.2.1]hept-5-yl]-5-(3-hydroxyphenyl)thiophene-2-carboxamide;
N-[2-azabicyclo[2.2.1]hept-5-yl]-5-(4-hydroxyphenyl)thiophene-2-carboxamide;
5-(2-aminophenyl)-N-[2-azabicyclo[2.2.1]hept-5-yl]thiophene-2-carboxamide;
5-(3-aminophenyl)-N-[2-azabicyclo[2.2.1]hept-5-yl]thiophene-2-carboxamide;
5-(4-aminophenyl)-N-[2-azabicyclo[2.2.1]hept-5-yl]thiophene-2-carboxamide;
5-(2-acetylaminophenyl)-N-[2-azabicyclo[2.2.1]hept-5-yl]thiophene-2-carboxamide;
5-(3-acetylaminophenyl)-N-[2-azabicyclo[2.2.1]hept-5-yl]thiophene-2-carboxamide;
5-(4-acetylaminophenyl)-N-[2-azabicyclo[2.2.1]hept-5-yl]thiophene-2-carboxamide;
N-[2-azabicyclo[2.2.1]hept-5-yl]-5-(2-trifluoroacetamidophenyl)thiophene-2-carboxamide;
N-[2-azabicyclo[2.2.1]hept-5-yl]-5-(3-trifluoroacetamidophenyl)thiophene-2-carboxamide;
N-[2-azabicyclo[2.2.1]hept-5-yl]-5-(4-trifluoroacetamidophenyl)thiophene-2-carboxamide;
N-[2-azabicyclo[2.2.1]hept-5-yl]-5-bromo-2-furamide;
N-[2-azabicyclo[2.2.1]hept-5-yl]-5-chloro-2-furamide;
N-[2-azabicyclo[2.2.1]hept-5-yl]-5-methyl-2-furamide;
N-[2-azabicyclo[2.2.1]hept-5-yl]-5-phenyl-2-furamide;
N-[2-azabicyclo[2.2.1]hept-5-yl]-5-(2-fluorophenyl)-2-furamide;
N-[2-azabicyclo[2.2.1]hept-5-yl]-5-(3-fluorophenyl)-2-furamide;
N-[2-azabicyclo[2.2.1]hept-5-yl]-5-(4-fluorophenyl)-2-furamide;
N-[2-azabicyclo[2.2.1]hept-5-yl]-5-(2-chlorophenyl)-2-furamide;
N-[2-azabicyclo[2.2.1]hept-5-yl]-5-(3-chlorophenyl)-2-furamide;
N-[2-azabicyclo[2.2.1]hept-5-yl]-5-(4-chlorophenyl)-2-furamide;
N-[2-azabicyclo[2.2.1]hept-5-yl]-5-(2-methoxyphenyl)-2-furamide;
N-[2-azabicyclo[2.2.1]hept-5-yl]-5-(3-methoxyphenyl)-2-furamide;
N-[2-azabicyclo[2.2.1]hept-5-yl]-5-(4-methoxyphenyl)-2-furamide;
N-[2-azabicyclo[2.2.1]hept-5-yl]-5-(2-methylphenyl)-2-furamide;

N-[2-azabicyclo[2.2.1]hept-5-yl]-5-(3-methylphenyl)-2-furamide;
N-[2-azabicyclo[2.2.1]hept-5-yl]-5-(4-methylphenyl)-2-furamide;
N-[2-azabicyclo[2.2.1]hept-5-yl]-5-(2-hydroxyphenyl)-2-furamide;
N-[2-azabicyclo[2.2.1]hept-5-yl]-5-(3-hydroxyphenyl)-2-furamide;
N-[2-azabicyclo[2.2.1]hept-5-yl]-5-(4-hydroxyphenyl)-2-furamide;
5-(2-aminophenyl)-N-[2-azabicyclo[2.2.1]hept-5-yl]-2-furamide;
5-(3-aminophenyl)-N-[2-azabicyclo[2.2.1]hept-5-yl]-2-furamide;
5-(4-aminophenyl)-N-[2-azabicyclo[2.2.1]hept-5-yl]-2-furamide;
5-(2-acetylaminophenyl)-N-[2-azabicyclo[2.2.1]hept-5-yl]-2-furamide;
5-(3-acetylaminophenyl)-N-[2-azabicyclo[2.2.1]hept-5-yl]-2-furamide;
5-(4-acetylaminophenyl)-N-[2-azabicyclo[2.2.1]hept-5-yl]-2-furamide;
N-[2-azabicyclo[2.2.1]hept-5-yl]-5-(2-trifluoroacetamidophenyl)-2-furamide;
N-[2-azabicyclo[2.2.1]hept-5-yl]-5-(3-trifluoroacetamidophenyl)-2-furamide;
N-[2-azabicyclo[2.2.1]hept-5-yl]-5-(4-trifluoroacetamidophenyl)-2-furamide;
N-[2-azabicyclo[2.2.1]hept-5-yl]-5-bromo-1,3-thiazole-2-carboxamide;
N-[2-azabicyclo[2.2.1]hept-5-yl]-5-chloro-1,3-thiazole-2-carboxamide;
N-[2-azabicyclo[2.2.1]hept-5-yl]-5-methyl-1,3-thiazole-2-carboxamide;
N-[2-azabicyclo[2.2.1]hept-5-yl]-5-phenyl-1,3-thiazole-2-carboxamide;
N-[2-azabicyclo[2.2.1]hept-5-yl]-5-(2-fluorophenyl)-1,3-thiazole-2-carboxamide;
N-[2-azabicyclo[2.2.1]hept-5-yl]-5-(3-fluorophenyl)-1,3-thiazole-2-carboxamide;
N-[2-azabicyclo[2.2.1]hept-5-yl]-5-(4-fluorophenyl)-1,3-thiazole-2-carboxamide;
N-[2-azabicyclo[2.2.1]hept-5-yl]-5-(2-chlorophenyl)-1,3-thiazole-2-carboxamide;
N-[2-azabicyclo[2.2.1]hept-5-yl]-5-(3-chlorophenyl)-1,3-thiazole-2-carboxamide;
N-[2-azabicyclo[2.2.1]hept-5-yl]-5-(4-chlorophenyl)-1,3-thiazole-2-carboxamide;
N-[2-azabicyclo[2.2.1]hept-5-yl]-5-(2-methoxyphenyl)-1,3-thiazole-2-carboxamide;
N-[2-azabicyclo[2.2.1]hept-5-yl]-5-(3-methoxyphenyl)-1,3-thiazole-2-carboxamide;
N-[2-azabicyclo[2.2.1]hept-5-yl]-5-(4-methoxyphenyl)-1,3-thiazole-2-carboxamide;
N-[2-azabicyclo[2.2.1]hept-5-yl]-5-(2-methylphenyl)-1,3-thiazole-2-carboxamide;
N-[2-azabicyclo[2.2.1]hept-5-yl]-5-(3-methylphenyl)-1,3-thiazole-2-carboxamide;
N-[2-azabicyclo[2.2.1]hept-5-yl]-5-(4-methylphenyl)-1,3-thiazole-2-carboxamide;
N-[2-azabicyclo[2.2.1]hept-5-yl]-5-(2-hydroxyphenyl)-1,3-thiazole-2-carboxamide;
N-[2-azabicyclo[2.2.1]hept-5-yl]-5-(3-hydroxyphenyl)-1,3-thiazole-2-carboxamide;
N-[2-azabicyclo[2.2.1]hept-5-yl]-5-(4-hydroxyphenyl)-1,3-thiazole-2-carboxamide;
5-(2-aminophenyl)-N-[2-azabicyclo[2.2.1]hept-5-yl]-1,3-thiazole-2-carboxamide;
5-(3-aminophenyl)-N-[2-azabicyclo[2.2.1]hept-5-yl]-1,3-thiazole-2-carboxamide;
5-(4-aminophenyl)-N-[2-azabicyclo[2.2.1]hept-5-yl]-1,3-thiazole-2-carboxamide;
5-(2-acetylaminophenyl)-N-[2-azabicyclo[2.2.1]hept-5-yl]-1,3-thiazole-2-carboxamide;
5-(3-acetylaminophenyl)-N-[2-azabicyclo[2.2.1]hept-5-yl]-1,3-thiazole-2-carboxamide;
5-(4-acetylaminophenyl)-N-[2-azabicyclo[2.2.1]hept-5-yl]-1,3-thiazole-2-carboxamide;
N-[2-azabicyclo[2.2.1]hept-5-yl]-5-(2-trifluoroacetamidophenyl)-1,3-thiazole-2-carboxamide;
N-[2-azabicyclo[2.2.1]hept-5-yl]-5-(3-trifluoroacetamidophenyl)-1,3-thiazole-2-carboxamide;
N-[2-azabicyclo[2.2.1]hept-5-yl]-5-(4-trifluoroacetamidophenyl)-1,3-thiazole-2-carboxamide;
N-[2-azabicyclo[2.2.1]hept-5-yl]-5-bromo-1,3-oxazole-2-carboxamide;
N-[2-azabicyclo[2.2.1]hept-5-yl]-5-chloro-1,3-oxazole-2-carboxamide;
N-[2-azabicyclo[2.2.1]hept-5-yl]-5-methyl-1,3-oxazole-2-carboxamide;
N-[2-azabicyclo[2.2.1]hept-5-yl]-5-phenyl-1,3-oxazole-2-carboxamide;
N-[2-azabicyclo[2.2 1]hept-5-yl]-5-(2-fluorophenyl)-1,3-oxazole-2-carboxamide;
N-[2-azabicyclo[2.2.1]hept-5-yl]-5-(3-fluorophenyl)-1,3-oxazole-2-carboxamide;
N-[2-azabicyclo[2.2.1]hept-5-yl]-5-(4-fluorophenyl)-1,3-oxazole-2-carboxamide;
N-[2-azabicyclo[2.2.1]hept-5-yl]-5-(2-chlorophenyl)-1,3-oxazole-2-carboxamide;
N-[2-azabicyclo[2.2.1]hept-5-yl]-5-(3-chlorophenyl)-1,3-oxazole-2-carboxamide;
N-[2-azabicyclo[2.2.1]hept-5-yl]-5-(4-chlorophenyl)-1,3-oxazole-2-carboxamide;
N-[2-azabicyclo[2.2.1]hept-5-yl]-5-(2-methoxyphenyl)-1,3-oxazole-2-carboxamide;
N-[2-azabicyclo[2.2.1]hept-5-yl]-5-(3-methoxyphenyl)-1,3-oxazole-2-carboxamide;
N-[2-azabicyclo[2.2.1]hept-5-yl]-5-(4-methoxyphenyl)-1,3-oxazole-2-carboxamide;
N-[2-azabicyclo[2.2.1]hept-5-yl]-5-(2-methylphenyl)-1,3-oxazole-2-carboxamide;
N-[2-azabicyclo[2.2.1]hept-5-yl]-5-(3-methylphenyl)-1,3-oxazole-2-carboxamide;
N-[2-azabicyclo[2.2.1]hept-5-yl]-5-(4-methylphenyl)-1,3-oxazole-2-carboxamide;
N-[2-azabicyclo[2.2.1]hept-5-yl]-5-(2-hydroxyphenyl)-1,3-oxazole-2-carboxamide;
N-[2-azabicyclo[2.2.1]hept-5-yl]-5-(3-hydroxyphenyl)-1,3-oxazole-2-carboxamide;
N-[2-azabicyclo[2.2.1]hept-5-yl]-5-(4-hydroxyphenyl)-1,3-oxazole-2-carboxamide;
5-(2-aminophenyl)-N-[2-azabicyclo[2.2.1]hept-5-yl]-1,3-oxazole-2-carboxamide;
5-(3-aminophenyl)-N-[2-azabicyclo[2.2.1]hept-5-yl]-1,3-oxazole-2-carboxamide;
5-(4-aminophenyl)-N-[2-azabicyclo[2.2.1]hept-5-yl]-1,3-oxazole-2-carboxamide;
5-(2-acetylaminophenyl)-N-[2-azabicyclo[2.2.1]hept-5-yl]-1,3-oxazole-2-carboxamide;
5-(3-acetylaminophenyl)-N-[2-azabicyclo[2.2.1]hept-5-yl]-1,3-oxazole-2-carboxamide;
5-(4-acetylaminophenyl)-N-[2-azabicyclo[2.2.1]hept-5-yl]-1,3-oxazole-2-carboxamide;
N-[2-azabicyclo[2.2.1]hept-5-yl]-5-(2-trifluoroacetamidophenyl)-1,3-oxazole-2-carboxamide;

N-[2-azabicyclo[2.2.1]hept-5-yl]-5-(3-trifluoroacetamidophenyl)-1,3-oxazole-2-carboxamide;
N-[2-azabicyclo[2.2.1]hept-5-yl]-5-(4-trifluoroacetamidophenyl)-1,3-oxazole-2-carboxamide;
N-[2-azabicyclo[2.2.1]hept-5-yl]-5-phenyl-1H-pyrrole-2-carboxamide; or
N-[2-azabicyclo[2.2.1]hept-5-yl]-5-phenyl-1-methyl-1H-pyrrole-2-carboxamide.

Another embodiment of the present invention includes any one or more of the following compounds as the free base or a pharmaceutically acceptable salt there of and as the pure enantiomer or as a racemic mixture thereof:

N-[2-azabicyclo[2.2.1]hept-6-yl]-5-bromothiophene-2-carboxamide;
N-[2-azabicyclo[2.2.1]hept-6-yl]-5-chlorothiophene-2-carboxamide;
N-[2-azabicyclo[2.2.1]hept-6-yl]-5-methylthiophene-2-carboxamide;
N-[2-azabicyclo[2.2.1]hept-6-yl]-5-phenylthiophene-2-carboxamide;
N-[2-azabicyclo[2.2.1]hept-6-yl]-5-(2-fluorophenyl)thiophene-2-carboxamide;
N-[2-azabicyclo[2.2.1]hept-6-yl]-5-(3-fluorophenyl)thiophene-2-carboxamide;
N-[2-azabicyclo[2.2.1]hept-6-yl]-5-(4-fluorophenyl)thiophene-2-carboxamide;
N-[2-azabicyclo[2.2.1]hept-6-yl]-5-(2-chlorophenyl)thiophene-2-carboxamide;
N-[2-azabicyclo[2.2.1]hept-6-yl]-5-(3-chlorophenyl)thiophene-2-carboxamide;
N-[2-azabicyclo[2.2.1]hept-6-yl]-5-(4-chlorophenyl)thiophene-2-carboxamide;
N-[2-azabicyclo[2.2.1]hept-6-yl]-5-(2-methoxyphenyl)thiophene-2-carboxamide;
N-[2-azabicyclo[2.2.1]hept-6-yl]-5-(3-methoxyphenyl)thiophene-2-carboxamide;
N-[2-azabicyclo[2.2.1]hept-6-yl]-5-(4-methoxyphenyl)thiophene-2-carboxamide;
N-[2-azabicyclo[2.2.1]hept-6-yl]-5-(2-methylphenyl)thiophene-2-carboxamide;
N-[2-azabicyclo[2.2.1]hept-6-yl]-5-(3-methylphenyl)thiophene-2-carboxamide;
N-[2-azabicyclo[2.2.1]hept-6-yl]-5-(4-methylphenyl)thiophene-2-carboxamide;
N-[2-azabicyclo[2.2.1]hept-6-yl]-5-(2-hydroxyphenyl)thiophene-2-carboxamide;
N-[2-azabicyclo[2.2.1]hept-6-yl]-5-(3-hydroxyphenyl)thiophene-2-carboxamide;
N-[2-azabicyclo[2.2.1]hept-6-yl]-5-(4-hydroxyphenyl)thiophene-2-carboxamide;
5-(2-aminophenyl)-N-[2-azabicyclo[2.2.1]hept-6-yl]thiophene-2-carboxamide;
5-(3-aminophenyl)-N-[2-azabicyclo[2.2.1]hept-6-yl]thiophene-2-carboxamide;
5-(4-aminophenyl)-N-[2-azabicyclo[2.2.1]hept-6-yl]thiophene-2-carboxamide;
5-(2-acetylaminophenyl)-N-[2-azabicyclo[2.2.1]hept-6-yl]thiophene-2-carboxamide;
5-(3-acetylaminophenyl)-N-[2-azabicyclo[2.2.1]hept-6-yl]thiophene-2-carboxamide;
5-(4-acetylaminophenyl)-N-[2-azabicyclo[2.2.1]hept-6-yl]thiophene-2-carboxamide;
N-[2-azabicyclo[2.2.1]hept-6-yl]-5-(2-trifluoroacetamidophenyl)thiophene-2-carboxamide;
N-[2-azabicyclo[2.2.1]hept-6-yl]-5-(3-trifluoroacetamidophenyl)thiophene-2-carboxamide;
N-[2-azabicyclo[2.2.1]hept-6-yl]-5-(4-trifluoroacetamidophenyl)thiophene-2-carboxamide;
N-[2-azabicyclo[2.2.1]hept-6-yl]-5-bromo-2-furamide;
N-[2-azabicyclo[2.2.1]hept-6-yl]-5-chloro-2-furamide;
N-[2-azabicyclo[2.2.1]hept-6-yl]-5-methyl-2-furamide;
N-[2-azabicyclo[2.2.1]hept-6-yl]-5-phenyl-2-furamide;
N-[2-azabicyclo[2.2.1]hept-6-yl]-5-(2-fluorophenyl)-2-furamide;
N-[2-azabicyclo[2.2.1]hept-6-yl]-5-(3-fluorophenyl)-2-furamide;
N-[2-azabicyclo[2.2.1]hept-6-yl]-5-(4-fluorophenyl)-2-furamide;
N-[2-azabicyclo[2.2.1]hept-6-yl]-5-(2-chlorophenyl)-2-furamide;
N-[2-azabicyclo[2.2.1]hept-6-yl]-5-(3-chlorophenyl)-2-furamide;
N-[2-azabicyclo[2.2.1]hept-6-yl]-5-(4-chlorophenyl)-2-furamide;
N-[2-azabicyclo[2.2.1]hept-6-yl]-5-(2-methoxyphenyl)-2-furamide;
N-[2-azabicyclo[2.2.1]hept-6-yl]-5-(3-methoxyphenyl)-2-furamide;
N-[2-azabicyclo[2.2.1]hept-6-yl]-5-(4-methoxyphenyl)-2-furamide;
N-[2-azabicyclo[2.2.1]hept-6-yl]-5-(2-methylphenyl)-2-furamide;
N-[2-azabicyclo[2.2.1]hept-6-yl]-5-(3-methylphenyl)-2-furamide;
N-[2-azabicyclo[2.2.1]hept-6-yl]-5-(4-methylphenyl)-2-furamide;
N-[2-azabicyclo[2.2.1]hept-6-yl]-5-(2-hydroxyphenyl)-2-furamide;
N-[2-azabicyclo[2.2.1]hept-6-yl]-5-(3-hydroxyphenyl)-2-furamide;
N-[2-azabicyclo[2.2.1]hept-6-yl]-5-(4-hydroxyphenyl)-2-furamide;
5-(2-aminophenyl)-N-[2-azabicyclo[2.2.1]hept-6-yl]-2-furamide;
5-(3-aminophenyl)-N-[2-azabicyclo[2.2.1]hept-6-yl]-2-furamide;
5-(4-aminophenyl)-N-[2-azabicyclo[2.2.1]hept-6-yl]-2-furamide;
5-(2-acetylaminophenyl)-N-[2-azabicyclo[2.2.1]hept-6-yl]-2-furamide;
5-(3-acetylaminophenyl)-N-[2-azabicyclo[2.2.1]hept-6-yl]-2-furamide;
5-(4-acetylaminophenyl)-N-[2-azabicyclo[2.2.1]hept-6-yl]-2-furamide;
N-[2-azabicyclo[2.2.1]hept-6-yl]-5-(2-trifluoroacetamidophenyl)-2-furamide;
N-[2-azabicyclo[2.2.1]hept-6-yl]-5-(3-trifluoroacetamidophenyl)-2-furamide;
N-[2-azabicyclo[2.2.1]hept-6-yl]-5-(4-trifluoroacetamidophenyl)-2-furamide;
N-[2-azabicyclo[2.2.1]hept-6-yl]-5-bromo-1,3-thiazole-2-carboxamide;
N-[2-azabicyclo[2.2.1]hept-6-yl]-5-chloro-1,3-thiazole-2-carboxamide;
N-[2-azabicyclo[2.2.1]hept-6-yl]-5-methyl-1,3-thiazole-2-carboxamide;
N-[2-azabicyclo[2.2.1]hept-6-yl]-5-phenyl-1,3-thiazole-2-carboxamide;
N-[2-azabicyclo[2.2.1]hept-6-yl]-5-(2-fluorophenyl)-1,3-thiazole-2-carboxamide;
N-[2-azabicyclo[2.2.1]hept-6-yl]-5-(3-fluorophenyl)-1,3-thiazole-2-carboxamide;
N-[2-azabicyclo[2.2.1]hept-6-yl]-5-(4-fluorophenyl)-1,3-thiazole-2-carboxamide;
N-[2-azabicyclo[2.2.1]hept-6-yl]-5-(2-chlorophenyl)-1,3-thiazole-2-carboxamide;

N-[2-azabicyclo[2.2.1]hept-6-yl]-5-(3-chlorophenyl)-1,3-thiazole-2-carboxamide;
N-[2-azabicyclo[2.2.1]hept-6-yl]-5-(4-chlorophenyl)-1,3-thiazole-2-carboxamide;
N-[2-azabicyclo[2.2.1]hept-6-yl]-5-(2-methoxyphenyl)-1,3-thiazole-2-carboxamide;
N-[2-azabicyclo[2.2.1]hept-6-yl]-5-(3-methoxyphenyl)-1,3-thiazole-2-carboxamide;
N-[2-azabicyclo[2.2.1]hept-6-yl]-5-(4-methoxyphenyl)-1,3-thiazole-2-carboxamide;
N-[2-azabicyclo[2.2.1]hept-6-yl]-5-(2-methylphenyl)-1,3-thiazole-2-carboxamide;
N-[2-azabicyclo[2.2.1]hept-6-yl]-5-(3-methylphenyl)-1,3-thiazole-2-carboxamide;
N-[2-azabicyclo[2.2.1]hept-6-yl]-5-(4-methylphenyl)-1,3-thiazole-2-carboxamide;
N-[2-azabicyclo[2.2.1]hept-6-yl]-5-(2-hydroxyphenyl)-1,3-thiazole-2-carboxamide;
N-[2-azabicyclo[2.2.1]hept-6-yl]-5-(3-hydroxyphenyl)-1,3-thiazole-2-carboxamide;
N-[2-azabicyclo[2.2.1]hept-6-yl]-5-(4-hydroxyphenyl)-1,3-thiazole-2-carboxamide;
5-(2-aminophenyl)-N-[2-azabicyclo[2.2.1]hept-6-yl]-1,3-thiazole-2-carboxamide;
5-(3-aminophenyl)-N-[2-azabicyclo[2.2.1]hept-6-yl]-1,3-thiazole-2-carboxamide;
5-(4-aminophenyl)-N-[2-azabicyclo[2.2.1]hept-6-yl]-1,3-thiazole-2-carboxamide;
5-(2-acetylaminophenyl)-N-[2-azabicyclo[2.2.1]hept-6-yl]-1,3-thiazole-2-carboxamide;
5-(3-acetylaminophenyl)-N-[2-azabicyclo[2.2.1]hept-6-yl]-1,3-thiazole-2-carboxamide;
5-(4-acetylaminophenyl)-N-[2-azabicyclo[2.2.1]hept-6-yl]-1,3-thiazole-2-carboxamide;
N-[2-azabicyclo[2.2.1]hept-6-yl]-5-(2-trifluoroacetamidophenyl)-1,3-thiazole-2-carboxamide;
N-[2-azabicyclo[2.2.1]hept-6-yl]-5-(3-trifluoroacetamidophenyl)-1,3-thiazole-2-carboxamide;
N-[2-azabicyclo[2.2.1]hept-6-yl]-5-(4-trifluoroacetamidophenyl)-1,3-thiazole-2-carboxamide;
N-[2-azabicyclo[2.2.1]hept-6-yl]-5-bromo-1,3-oxazole-2-carboxamide;
N-[2-azabicyclo[2.2.1]hept-6-yl]-5-chloro-1,3-oxazole-2-carboxamide;
N-[2-azabicyclo[2.2.1]hept-6-yl]-5-methyl-1,3-oxazole-2-carboxamide;
N-[2-azabicyclo[2.2.1]hept-6-yl]-5-phenyl-1,3-oxazole-2-carboxamide;
N-[2-azabicyclo[2.2.1]hept-6-yl]-5-(2-fluorophenyl)-1,3-oxazole-2-carboxamide;
N-[2-azabicyclo[2.2.1]hept-6-yl]-5-(3-fluorophenyl)-1,3-oxazole-2-carboxamide;
N-[2-azabicyclo[2.2.1]hept-6-yl]-5-(4-fluorophenyl)-1,3-oxazole-2-carboxamide;
N-[2-azabicyclo[2.2.1]hept-6-yl]-5-(2-chlorophenyl)-1,3-oxazole-2-carboxamide;
N-[2-azabicyclo[2.2.1]hept-6-yl]-5-(3-chlorophenyl)-1,3-oxazole-2-carboxamide;
N-[2-azabicyclo[2.2.1]hept-6-yl]-5-(4-chlorophenyl)-1,3-oxazole-2-carboxamide;
N-[2-azabicyclo[2.2.1]hept-6-yl]-5-(2-methoxyphenyl)-1,3-oxazole-2-carboxamide;
N-[2-azabicyclo[2.2.1]hept-6-yl]-5-(3-methoxyphenyl)-1,3-oxazole-2-carboxamide;
N-[2-azabicyclo[2.2.1]hept-6-yl]-5-(4-methoxyphenyl)-1,3-oxazole-2-carboxamide;
N-[2-azabicyclo[2.2.1]hept-6-yl]-5-(2-methylphenyl)-1,3-oxazole-2-carboxamide;
N-[2-azabicyclo[2.2.1]hept-6-yl]-5-(3-methylphenyl)-1,3-oxazole-2-carboxamide;
N-[2-azabicyclo[2.2.1]hept-6-yl]-5-(4-methylphenyl)-1,3-oxazole-2-carboxamide;
N-[2-azabicyclo[2.2.1]hept-6-yl]-5-(2-hydroxyphenyl)-1,3-oxazole-2-carboxamide;
N-[2-azabicyclo[2.2.1]hept-6-yl]-5-(3-hydroxyphenyl)-1,3-oxazole-2-carboxamide;
N-[2-azabicyclo[2.2.1]hept-6-yl]-5-(4-hydroxyphenyl)-1,3-oxazole-2-carboxamide;
5-(2-aminophenyl)-N-[2-azabicyclo[2.2.1]hept-6-yl]-1,3-oxazole-2-carboxamide;
5-(3-aminophenyl)-N-[2-azabicyclo[2.2.1]hept-6-yl]-1,3-oxazole-2-carboxamide;
5-(4-aminophenyl)-N-[2-azabicyclo[2.2.1]hept-6-yl]-1,3-oxazole-2-carboxamide;
5-(2-acetylaminophenyl)-N-[2-azabicyclo[2.2.1]hept-6-yl]-1,3-oxazole-2-carboxamide;
5-(3-acetylaminophenyl)-N-[2-azabicyclo[2.2.1]hept-6-yl]-1,3-oxazole-2-carboxamide;
5-(4-acetylaminophenyl)-N-[2-azabicyclo[2.2.1]hept-6-yl]-1,3-oxazole-2-carboxamide;
N-[2-azabicyclo[2.2.1]hept-6-yl]-5-(2-trifluoroacetamidophenyl)-1,3-oxazole-2-carboxamide;
N-[2-azabicyclo[2.2.1]hept-6-yl]-5-(3-trifluoroacetamidophenyl)-1,3-oxazole-2-carboxamide;
N-[2-azabicyclo[2.2.1]hept-6-yl]-5-(4-trifluoroacetamidophenyl)-1,3-oxazole-2-carboxamide;
N-[2-azabicyclo[2.2.1]hept-6-yl]-5-phenyl-1H-pyrrole-2-carboxamide; or
N-[2-azabicyclo[2.2.1]hept-6-yl]-5-phenyl-1-methyl-1H-pyrrole-2-carboxamide.

The compounds of Formula I (Azabicyclo is I) have asymmetric centers on the quinuclidine ring. The compounds of the present invention include quinuclidines with the 3R configuration and also includes racemic mixtures and compositions of varying degrees of streochemical purities. For example, and not by limitation, compounds of Formula I include compounds with stereospecificity including:

The compounds of Formula I (Azabicyclo is II) have asymmetric centers on the [2.2.1]azabicyclic ring at C3 and C4. The scope of this invention includes racemic mixtures and the separate stereoisomers of Formula I being endo-4S, endo-4R, exo-4S, exo-4R:

endo-4S

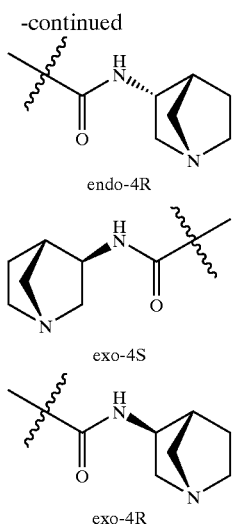

endo-4R exo-4S exo-4R

The endo isomer is the isomer where the non-hydrogen substituent at C3 of the [2.2.1] azabicyclic compound is projected toward the larger of the two remaining bridges. The exo isomer is the isomer where the non-hydrogen substituent at C3 of the [2.2.1] azabicyclic compound is projected toward the smaller of the two remaining bridges. Thus, there can be four separate isomers: exo-4(R), exo-4(S), endo-4(R), and endo-4(S).

The compounds of Formula I (Azabicyclo III) have asymmetric centers on the [2.2.1]azabicyclic ring at C1, C4 and C5. The scope of this invention includes racemic mixtures and the separate stereoisomers of Formula I being (1R,4R,5S), (1R,4R,5R), (1S,4S,5R), (1S,4S,5S):

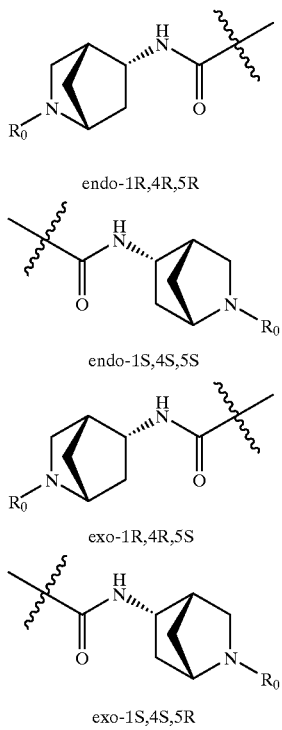

endo-1R,4R,5R endo-1S,4S,5S exo-1R,4R,5S exo-1S,4S,5R

The endo isomer is the isomer where the non-hydrogen substituent at C5 of the [2.2.1] azabicyclic compound is projected toward the larger of the two remaining bridges. The exo isomer is the isomer where the non-hydrogen substituent at C5 of the [2.2.1] azabicyclic compound is projected toward the smaller of the two remaining bridges. Thus, there can be four separate isomers: exo-(1R,4R,5S), exo-(1S,4S,5R), endo-(1S,4S,5S), endo-(1R,4R,5R).

The compounds of Formula I (Azabicyclo IV) have asymmetric center(s) on the [2.2.1] azabicyclic ring at C1, C4 and C6. The scope of this invention includes racemic mixtures and the separate stereoisomers of Formula I being exo-(1S,4R,6S), exo-(1R,4S,6R), endo-(1S,4R,6R), and endo-(1R,4S,6S):

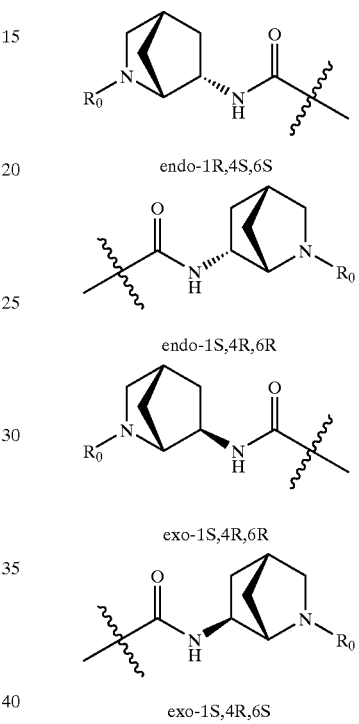

endo-1R,4S,6S endo-1S,4R,6R exo-1S,4R,6R exo-1S,4R,6S

The endo isomer is the isomer where the non-hydrogen substituent at C6 of the [2.2.1] azabicyclic compound is projected toward the larger of the two remaining bridges. The exo isomer is the isomer where the non-hydrogen substituent at C6 of the [2.2.1] azabicyclic compound is projected toward the smaller of the two remaining bridges. Thus, there can be four separate isomers: exo-(1S,4R,6S), exo-(1R,4S,6R), endo-(1S,4R,6R), and endo-(1R,4S,6S).

The compounds of Formula I (Azabicyclo is V) have asymmetric center(s) on the [3.2.1] azabicyclic ring at C3 and C5. The scope of this invention includes racemic mixtures and the separate stereoisomers of Formula I being endo-3S, 5R, endo-3R, 5S, exo-3R, 5R, exo-3S, 5S:

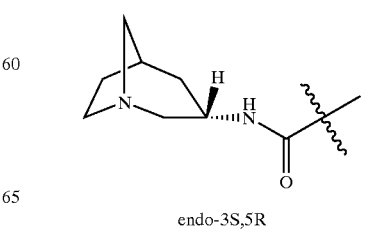

endo-3S,5R

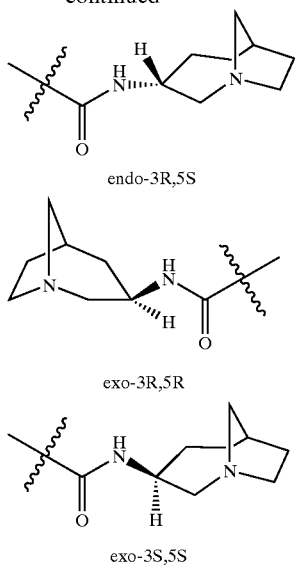

endo-3R,5S exo-3R,5R exo-3S,5S

The compounds of Formula I (Azabicyclo is VI) have asymmetric centers on the [3.2.2] azabicyclic ring with one center being at C3 when R₂ is absent. The scope of this invention includes racemic mixtures and the separate stereoisomers of Formula I being 3(S) and 3(R):

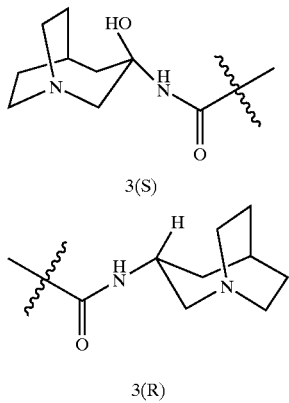

3(S)

3(R)

The compounds of the present invention having the specified stereochemistry have different levels of activity and that for a given set of values for the variable substituents one isomer may be preferred over the other isomers. Although it is desirable that the stereochemical purity be as high as possible, absolute purity is not required. This invention involves racemic mixtures and compositions of varying degrees of streochemical purities when the Azabicyclo is substituted with only the amide/thioamide or is substituted with substituents in addition to the amide/thioamide, e.g., k is 1 or 2. This invention involves racemic mixtures and compositions of varying degrees of stereochemical purities. When racemic mixtures and compositions are referenced, it means racemic mixtures and compositions of varying degree of stereochemical purities. It is preferred to carry out stereoselective syntheses and/or to subject the reaction product to appropriate purification steps so as to produce substantially enantiomerically pure materials. Suitable stereoselective synthetic procedures for producing enantiomerically pure materials are well known in the art, as are procedures for purifying racemic mixtures into enantiomerically pure fractions. Naming a specific isomer includes racemic mixtures thereof within the scope of this invention. Therefore, naming N-(exo-(4S)-1-azabicyclo[2.2.1]hept-3-yl)-5-bromo-thiophene-2-carboxamide includes N-(exo-4(rac)-1-azabicyclo[2.2.1]hept-3-yl)-5-bromo-thiophene-2-carboxamide, N-((3-rac)-4(S)-1-azabicyclo[2.2.1]hept-3-yl)-5-bromo-thiophene-2-carboxamide and N-((rac)1-azabicyclo[2.2.1]hept-3-yl)-5-bromo-thiophene-2-carboxamide.

Stereoselective syntheses and/or subjecting the reaction product to appropriate purification steps produces substantially enantiomerically pure materials. Suitable stereoselective synthetic procedures for producing enantiomerically pure materials are well known in the art, as are procedures for purifying racemic mixtures into enantiomerically pure fractions.

Another embodiment of the compounds of Formula I includes any one or more or combination of the following configurations for compounds:

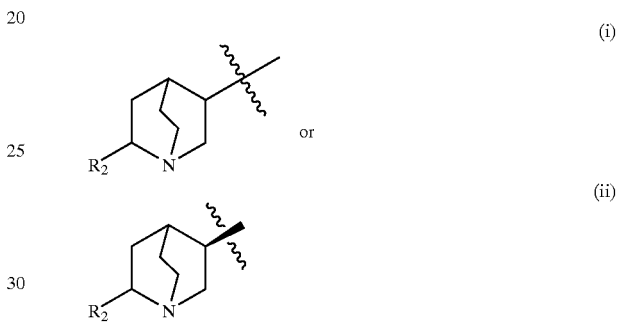

where (i) the compound is a racemic mixture, or (ii) the compound has the R stereochemistry at C-3 as discussed herein and stereochemistry is unspecified at C-6.

Another embodiment of compounds of Formula I includes any one or more or combination of the following configurations for compounds:

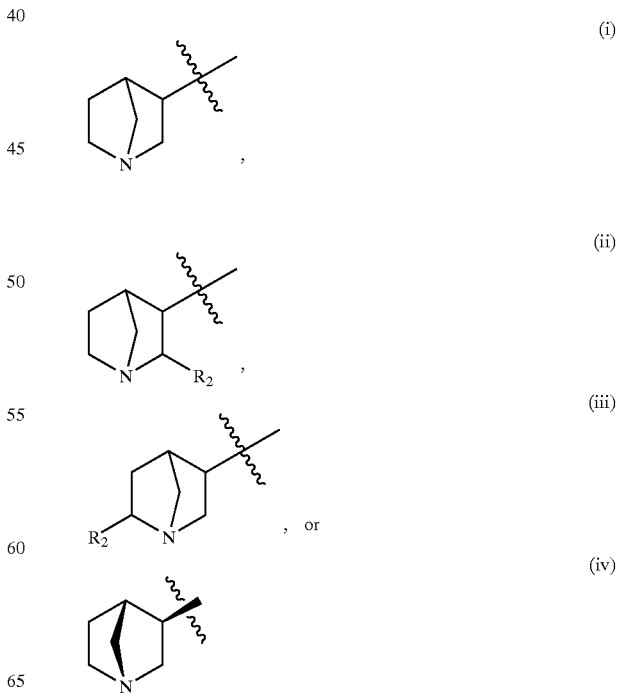

where (i) $k_2$ is 0 ($R_2$ is absent);

(ii) $R_2$ has any definition discussed herein;

(iii) $R_2$ has any definition discussed herein; or (iv) the 2.2.1 moiety has the exo-4(S) stereochemistry as discussed herein.

Another embodiment of compounds of Formula I includes any one or more or combination of the following configurations for compounds:

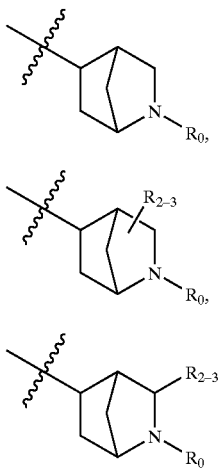

where (i) $R_{2-3}$ is H;

(ii) $R_{2-3}$ is F, Cl, Br, I, alkyl, halogenated alkyl, substituted alkyl, or substituted phenyl or substituted naphthyl; or (iii) $R_{2-3}$ is alkyl, halogenated alkyl, substituted alkyl, or substituted phenyl or substituted naphthyl.

Another embodiment of compounds of Formula I includes any one or more or combination of the following configurations for compounds:

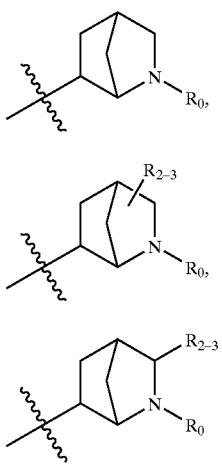

where (i) $R_{2-3}$ is H;

(ii) $R_{2-3}$ is F, Cl, Br, I, alkyl, halogenated alkyl, substituted alkyl, or substituted phenyl or substituted naphthyl; or (iii) $R_{2-3}$ is alkyl, halogenated alkyl, substituted alkyl, or substituted phenyl or substituted naphthyl.

Another embodiment of compounds of Formula I includes any one or more or combination of the following configurations for compounds:

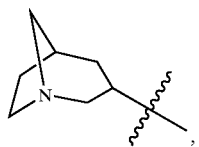

(i)

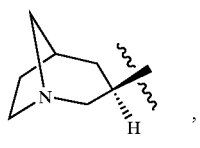

(ii)

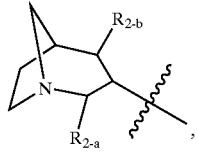

(iii)

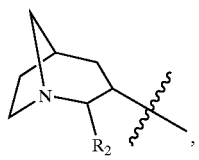

(iv)

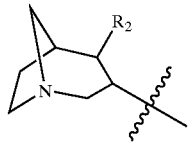

(v)

where (i) $k_5$ is 0 ($R_2$ is absent);

(ii) $R_2$ is absent and where the Azabicyclo has the stereochemistry of 3R, 5R;

(iii) $k_5$ is 2, where $R_2$ is $R_{2-a}$ and $R_{2-b}$, both of which have any definition discussed herein for $R_2$;

(iv) $k_5$ is 1, where $R_2$ has any definition discussed herein; or (v) $k_5$ is 1, where $R_2$ has any definition discussed herein.

Another embodiment of compounds of Formula I includes any one or more or combination of the following configurations for compounds:

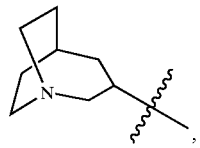

(i)

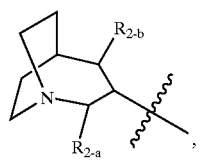

(ii)

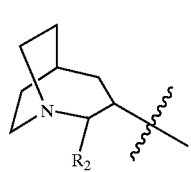

(iii)

-continued

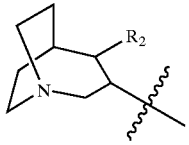
(iv)

where (i) $k_6$ is 0 ($R_2$ is absent);

(ii) $k_6$ is 2, where $R_2$ is $R_{2-a}$ and $R_{2-b}$, both of which have any definition discussed herein for $R_2$;

(iii) $k_6$ is 1, where $R_2$ has any definition discussed herein; or (iv) $k_6$ is 1, where $R_2$ has any definition discussed herein.

It has further surprisingly been found that the compounds of the present invention having the N-[1-azabicyclo[2.2.1] heptyl moiety generally have better metabolic stability than the corresponding compound with quinuclidinyl as the azabicyclic moiety.

Further aspects and embodiments of the invention may become apparent to those skilled in the art from a review of the following detailed description, taken in conjunction with the examples and the appended claims. While the invention is susceptible of embodiments in various forms, described hereafter are specific embodiments of the invention with the understanding that the present disclosure is intended as illustrative, and is not intended to limit the invention to the specific embodiments described herein.

DETAILED DESCRIPTION OF THE INVENTION

Surprisingly, we have found that compounds of Formula I:

Azabicyclo-N($R_1$)—C(=X)—W      Formula I wherein, X is O or S;

$R_1$ is H, alkyl, cycloalkyl, halogenated alkyl, or aryl;

W is a cyclic heteroaromatic moiety where the heteroatoms can be from 1–2 atoms selected from oxygen, sulfur, or nitrogen of the following structures:

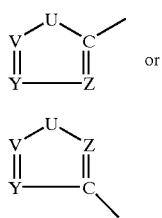

(a)

or (b)

wherein U is —O—, —S—, or —N($R_U$)—;

V and Y are independently =N—, or =C($R_{VY}$)—;

Z is =N—, or =CH—, provided that when both V and Y are =C($R_{VY}$)— and Z is =CH—, only one =C($R_{VY}$)— can be =CH—, further provided that when U is —O—, Y is =C($R_{VY}$)— and Z is =C(H)—, V cannot be =N—, and further provided that no more than one of V, Y, or Z is a heteroatom;

$R_U$ is H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —SO$_2$R$_8$, and provided that when W is (b) and Z is =N— and U is N($R_U$), $R_U$ cannot be phenyl or substituted phenyl;

Each $R_{VY}$ is independently H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —OR$_8$, —OR$_{14}$, —SR$_8$, —SR$_{14}$, F, Cl, Br, I, —NR$_8$R$_8$, —NR$_{14}$R$_{14}$, —C(O)R$_8$, —C(O)R$_{14}$, —C(O)NR$_8$R$_8$, —C(O)NR$_{14}$R$_{14}$, —C(R$_6$)=N(R$_{16}$), —CN, —NR$_8$C(O)R$_{11}$, —S(O)$_2$NR$_8$R$_8$, —OS(O)$_2$R$_{11}$, —S(O)$_2$R$_8$, —S(O)$_2$R$_{14}$, —NR$_8$S(O)$_2$R$_8$, —N(H)C(O)N(H)R$_8$, —NO$_2$, R$_7$, R$_9$, and 0–3 substituents independently selected from F, Cl, Br, I, or R$_{15}$, and 0–3 substituents independently selected from F, Cl, Br, I, or R$_{15}$;

Azabicyclo is

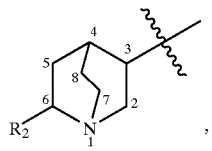

I

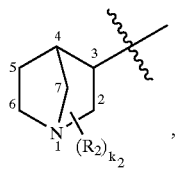

II

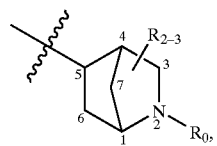

III

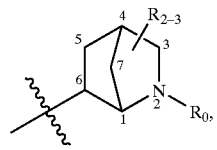

IV

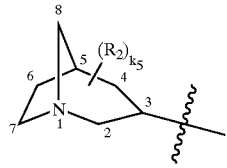

V

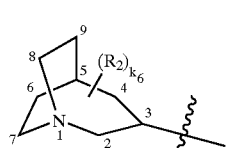

VI $R_0$ is H, lower alkyl, substituted lower alkyl, or halogenated lower alkyl;

$R_2$ is alkyl, halogenated alkyl, substituted alkyl, cycloalkyl, aryl or $R_2$ is absent provided that $k_2$, $k_5$, or $k_6$ is 0;

$k_2$ is 0 or 1;

$k_5$ and $k_6$ are independently 0, 1, or 2;

$R_{2-3}$ is H, alkyl, halogenated alkyl, substituted alkyl, F, Cl, Br, or I;

Alkyl is both straight and branched-chain moieties having from 1–6 carbon atoms;

Halogenated alkyl is an alkyl moiety having from 1–6 carbon atoms and having 1 to (2n+1) substituent(s) independently selected from F, Cl, Br, or I, where n is the maximum number of carbon atoms in the moiety;

Substituted alkyl is an alkyl moiety having from 1–6 carbon atoms and having 0–3 substituents independently selected from F, Cl, Br, or I, and further having 1 substituent selected from $R_7$, $R_9$, —$OR_{10}$, —$SR_{10}$, —$NR_{10}R_{10}$, —C(O)$R_{10}$, —$NO_2$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Limited substituted alkyl is a substituted alkyl having from 1–6 carbon atoms and having 0–3 substituents independently selected from F, Cl, Br, or I, and further having 1 substituent on either only the ω carbon and selected from —$OR_{11}$, —$SR_{11}$, —$NR_{11}R_{11}$, —C(O)$R_{11}$, —$NO_2$, —C(O)$NR_{11}R_{11}$, —CN, —$NR_{10}$C(O)$R_{11}$, —S(O)$_2NR_{10}R_{10}$, —$NR_{10}$S(O)$_2R_{10}$, or on any carbon with sufficient valency but not on the ω carbon and selected from $R_7$, $R_9$, —$OR_{10}$, —$SR_{10}$, —$NR_{10}R_{10}$, —C(O)$R_{10}$, —$NO_2$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Alkenyl is straight and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from F, Cl, Br, or I, where n is the maximum number of carbon atoms in the moiety;

Substituted alkenyl is an unsaturated alkenyl moiety having from 2–6 carbon atoms and having 0–3 substituents independently selected from F, or Cl, and further having 1 substituent selected from $R_7$, $R_9$, —$OR_{10}$, —$SR_{10}$, —$NR_{10}R_{10}$, —C(O)$R_{10}$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Limited substituted alkenyl is a substituted alkenyl having from 1–6 carbon atoms and having 0–3 substituents independently selected from F, Cl, Br, or I, and further having 1 substituent on either only the ω carbon and selected from —$OR_{11}$, —$SR_{11}$, —$NR_{11}R_{11}$, —C(O)$R_{11}$, —$NO_2$, —C(O)$NR_{11}R_{11}$, —CN, —$NR_{10}$C(O)$R_{11}$, —S(O)$_2NR_{10}R_{10}$, or —$NR_{10}$S(O)$_2R_{10}$, or on any carbon with sufficient valency but not on the ω carbon and selected from $R_7$, $R_9$, —$OR_{10}$, —$SR_{10}$, —$NR_{10}R_{10}$, —C(O)$R_{10}$, —$NO_2$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Alkynyl is straight and branched-chain moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from F, Cl, Br, or I, where n is the maximum number of carbon atoms in the moiety;

Substituted alkynyl is an unsaturated alkynyl moiety having from 3–6 carbon atoms and having 0–3 substituents independently selected from F, or Cl, and further having 1 substituent selected from $R_7$, $R_9$, —$OR_{10}$, —$SR_{10}$, —$NR_{10}R_{10}$, —C(O)$R_{10}$, —CN, —C(O)$NR_{10}R_{10}$, —$NR_{10}C$(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Limited substituted alkynyl is a substituted alkynyl having from 1–6 carbon atoms and having 0–3 substituents independently selected from F, Cl, Br, or I, and further having 1 substituent on either only the ω carbon and selected from —$OR_{11}$, —$SR_{11}$, —$NR_{11}R_{11}$, —C(O)$R_{11}$, —$NO_2$, —C(O)$NR_{11}R_{11}$, —CN, —$NR_{10}$C(O)$R_{11}$, —S(O)$_2NR_{10}R_{10}$, or —$NR_{10}$S(O)$_2R_{10}$, or on any carbon with sufficient valency but not on the ω carbon and selected from $R_7$, $R_9$, —$OR_{10}$, —$SR_{10}$, —$NR_{10}R_{10}$, —C(O)$R_{10}$, —$NO_2$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Cycloalkyl is a cyclic alkyl moiety having from 3–6 carbon atoms;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from $R_7$, $R_9$, —$OR_{10}$, —$SR_{10}$, —$NR_{10}R_{10}$, —C(O)$R_{10}$, —C(O)$NR_{10}R_{10}$, —CN, —$NR_{10}$C(O)$R_{10}$, —S(O)$_2NR_{10}R_{10}$, —$NR_{10}$S(O)$_2R_{10}$, —$NO_2$, phenyl, or phenyl having 1 substituent selected from $R_{20}$ and further having 0–3 substituents independently selected from F, Cl, Br, or I;

Heterocycloalkyl is a cyclic moiety having 4–7 atoms with 1–2 atoms within the ring being —S—, —N($R_{19}$)—, or —O—;

Halogenated heterocycloalkyl is a cyclic moiety having from 4–7 atoms with 1–2 atoms within the ring being —S—, —N($R_{19}$)—, or —O—, and having 1–4 substituents independently selected from F, or Cl;

Substituted heterocycloalkyl is a cyclic moiety having from 4–7 atoms with 1–2 atoms within the ring being —S—, —N($R_{19}$)—, or —O— and having 0–3 substituents independently selected from F, or Cl, and further having 1 substituent selected from $R_7$, $R_9$, —$OR_{10}$, —$SR_{10}$, —$NR_{10}R_{10}$, —C(O)$R_{10}$, —C(O)$NR_{10}R_{10}$, —CN, —$NR_{10}$C(O)$R_{10}$, —$NO_2$, —S(O)$_2NR_{10}R_{10}$, —$NR_{10}$S(O)$_2R_{10}$, phenyl, or phenyl having 1 substituent selected from $R_{20}$ and further having 0–3 substituents independently selected from F, Cl, Br, or I;

Lactam heterocycloalkyl is a cyclic moiety having from 4–7 atoms with one atom being only nitrogen with the bond to the lactam heterocycloalkyl thru said atom being only nitrogen and having a =O on a carbon adjacent to said nitrogen, and having up to 1 additional ring atom being oxygen, sulfur, or nitrogen and further having 0–2 substituents selected from F, Cl, Br, I, or $R_{15}$ where valency allows;

Aryl is phenyl, substituted phenyl, naphthyl, or substituted naphthyl;

Substituted phenyl is a phenyl either having 1–4 substituents independently selected from F, Cl, Br, or I, or having 1 substituent selected from $R_{12}$ and 0–3 substituents independently selected from F, Cl, Br, or I;

Substituted naphthyl is a naphthalene moiety either having 1–4 substituents independently selected from F, Cl, Br, or I, or having 1 substituent selected from $R_{12}$ and 0–3 substituents independently selected from F, Cl, Br, or I, where the substitution can be independently on either the same ring or different rings of said naphthalene moiety;

$R_6$ is H, F, Cl, CN, alkyl, substituted alkyl, cycloalkyl, halogenated alkyl, and aryl;

$R_7$ is 5-membered heteroaromatic mono-cyclic moieties containing within the ring 1–3 heteroatoms independently selected from the group consisting of —O—, =N—, —N($R_{19}$)—, and —S—, and having 0–1 substituent selected from $R_{20}$ and further having 0–3 substituents independently selected from F, Cl, Br, or I, or $R_7$ is a 9-membered fused-ring moiety having a 6-membered ring fused to a 5-membered ring and having the formula

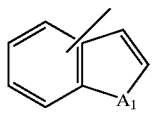

wherein $A_1$ is O, S, or $NR_{19}$,

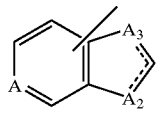

wherein A is $CR_{18}$ or N, $A_2$ and $A_3$ are independently selected from $CR_{18}$, $C(R_{18})_2$, O, S, N, or $NR_{19}$, provided that both $A_2$ and $A_3$ are not simultaneously O, simultaneously S, or simultaneously O and S, or

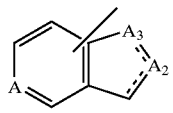

wherein A is $CR_{18}$ or N, $A_2$ and $A_3$ are independently selected from $CR_{18}$, $C(R_{18})_2$, O, S, N, or $NR_{19}$, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, $R_7$, $R_9$, or phenyl having 1 substituent selected from $R_{20}$ and further having 0–3 substituents independently selected from F, Cl, Br, or I;

Each $R_{11}$ is independently H, alkyl, cycloalkyl, heterocycloalkyl, halogenated alkyl, halogenated cycloalkyl, or halogenated heterocycloalkyl;

$R_{12}$ is —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, $R_7$, $R_9$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, or phenyl having 0–1 substituent selected from $R_{20}$ and further having 0–3 substituents independently selected from F, Cl, Br, or I;

$R_{13}$ is —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$CF_3$, or —$NO_2$;

Each $R_{14}$ is independently H, alkyl, halogenated alkyl, limited substituted alkyl, cycloalkyl, halogenated cycloalkyl, substituted cycloalkyl, heterocycloalkyl, halogenated heterocycloalkyl, or substituted heterocycloalkyl;

$R_{15}$ is alkyl, substituted alkyl, halogenated alkyl, —$OR_{11}$, —CN, —$NO_2$, —$NR_{10}R_{10}$;

$R_{16}$ is —$OR_{17}$, —$NR_{17}R_{17}$, —$NR_{17}C(O)R_{17}$, —$NR_{17}S(O)_2R_{17}$, —$N(R_{17})C(O)NR_{17}R_{17}$, —$NR_{17}C(O)OR_{17}$;

$R_{17}$ is H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, phenyl, phenyl having 1–4 substituents independently selected from F, Cl, Br, I and $R_{15}$, naphthyl, or naphthyl having 1–4 substituents independently selected from F, Cl, Br, I and $R_{15}$;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, F, Cl, Br, or I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F. Cl, Br, I, or $R_{13}$, or heterocycloalkyl substituted with 1–4 substituent(s) independently selected from F, Cl, Br, I, or $R_{13}$;

or pharmaceutical composition, pharmaceutically acceptable salt, racemic mixture, or pure enantiomer thereof useful to treat any one or more or combination of the following: cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems in general and associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulemia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs. The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the compounds of the present invention, pharmaceutical compositions containing the active compounds, and methods to treat the identified diseases.

Non-inclusive examples of heteroaryl compounds that fall within the definition of $R_7$ and $R_9$ include, but are not limited to, thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl.

Non-inclusive examples of heterocycloalkyl include, but are not limited to, tetrahydrofurano, tetrahydropyrano, morpholino, pyrrolidino, piperidino, piperazine, azetidino, azetidinono, oxindolo, dihydroimidazolo, and pyrrolidinono Some of the amines described herein require the use of an amine-protecting group to ensure functionalization of the desired nitrogen. One of ordinary skill in the art would appreciate where, within the synthetic scheme to use said protecting group. Amino protecting group includes, but is not limited to, carbobenzyloxy (CBz), tert butoxy carbonyl (BOC) and the like. Examples of other suitable amino protecting groups are known to person skilled in the art and can be found in "Protective Groups in Organic synthesis," 3rd Edition, authored by Theodora Greene and Peter Wuts.

Abbreviations which are well known to one of ordinary skill in the art may be used (e.g., "Ph" for phenyl, "Me" for methyl, "Et" for ethyl, "h" for hour or hours, "min" for minute or minutes, and "rt" or "RT" for room temperature).

All temperatures are in degrees Centigrade.
Room temperature is within the range of 15–25 degrees Celsius.
AChR refers to acetylcholine receptor.
Pre-senile dementia is also known as mild cognitive impairment.
nAChR refers to nicotinic acetylcholine receptor.
$5HT_3R$ refers to the serotonin-type 3 receptor.
α-btx refers to α-bungarotoxin.
FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).
TLC refers to thin-layer chromatography.
HPLC refers to high pressure liquid chromatography.
MeOH refers to methanol.
EtOH refers to ethanol.
IPA refers to isopropyl alcohol.
THF refers to tetrahydrofuran.
DMSO refers to dimethylsulfoxide.
DMF refers to dimethylformamide.
EtOAc refers to ethyl acetate.
$Na_2SO_4$ refers to anhydrous sodium sulfate.
$K_2CO_3$ refers to potassium carbonate.
$MgSO_4$ refers to anhydrous magnesium sulfate.
TMS refers to tetramethylsilane.
TEA refers to triethylamine.
DIEA refers to N,N-diisopropylethylamine.
MLA refers to methyllycaconitine.
Ether refers to diethyl ether.
HATU refers to O-(7-azabenzotriazol-1-yl)-N,N,N',N'-tetramethyluronium hexafluorophosphate.
DPPA refers to diphenylphosphoryl azide.
50% saturated 1:1 $NaCl/NaHCO_3$ means a solution made by making a solution of 1:1 saturated $NaCl/NaHCO_3$ and adding an equal volume of water.
$CH_3SO_2Cl$ refers to methanesulfonyl chloride.
Halogen is F, Cl, Br, or I.
The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

The ω carbon is determined by counting the longest carbon chain of the alkyl-type moiety with the C-1 carbon being the carbon attached to W of the core molecule and the ω carbon being the carbon furthest, e.g., separated by the greatest number of carbon atoms in the chain, from said C-1 carbon.

The core molecule is the azabicyclo-(carboxamide-type moiety)-W:

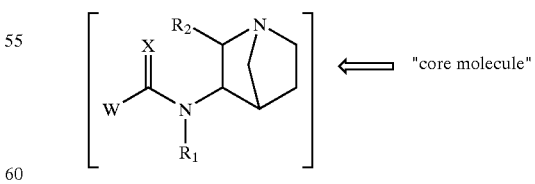

Therefore, when determining the ω carbon, the C-1 carbon will be the carbon attached to W of the core molecule and the ω carbon will be the carbon furthest from said C-1 carbon.

One of the most conventionally accepted ways of naming the compound pictured below is 5-(2-aminophenyl)-N-[-1- azabicyclo[2.2.1]hept-3-yl]thiophene-2-carboxamide, but for one ordinarily skilled in the art, the following name also describes the same compound, N-[1-azabicyclo[2.2.1]hept-3-yl]-5-(2-aminophenyl)-thiophene-2-carboxamide:

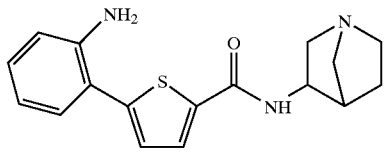

The two are used interchangeably in this patent.

Mammal denotes human and other mammals.

Brine refers to an aqueous saturated sodium chloride solution.

Equ means molar equivalents.

IR refers to infrared spectroscopy.

Lv refers to leaving groups within a molecule, including Cl, OMe, OEt, or mixed anhydride.

Parr refers to the name of the company who sells the jars used for conducting reactions under pressure.

PSI means pound per square inch.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. [M+H]$^+$ refers to an ion composed of the parent plus a proton. [M−H]$^−$ refers to an ion composed of the parent minus a proton. [M+Na]$^+$ refers to an ion composed of the parent plus a sodium ion. [M+K]$^+$ refers to an ion composed of the parent plus a potassium ion. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001–100 mg/kg/day for an adult, preferably in the range of about 0.1–50 mg/kg/day for an adult. A total daily dose of about 1–1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., *Psychopharmacology (Berl).*, 142(4):334–42, March 1999; Wilens, T. E. et. al., *Am. J. Psychiatry*, 156(12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "atypical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al., *Am. J. Psychiatry*, 157:55–9, 2000). Multiple studies show that nicotine normalizes the sensory deficit of schizophrenia (Adler, L. E. et. al., *Am. J. Psychiatry*, 150:1856–61, 1993). Pharmacological studies indicate that nicotine's effect on sensory gating is via the α7 nAChR (Adler, L. E. et. al., *Schizophr. Bull.*, 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., *Proc. Nat'l Acad. Sci. USA*, 94(2):587–92, 1997; Myles-Worsley, M. et. al., *Am. J. Med. Genet*, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and $5HT_3R$. To conduct such an assay, one uses cell lines that expressed functional forms of the α7 nAChR using the α7/$5-HT_3$ channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, atypical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the atypical antipsychotic drugs, and thus, these atypical antipsychotic drugs have a lower risk of producing tardive dyskinesia. Finally these atypical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the anti-psychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I, noted above, and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's Disease, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairment) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are α7 nAChR agonists. Therefore, yet other diseases to be treated with compounds of the present invention include treating the cognitive and attention deficits as well as the neurodegeneration associated with any one or more or combination of the following: attention deficit disorder, attention deficit hyperactivity disorder, depression, anxiety, general anxiety disorder, post traumatic stress disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, Parkinson's disease, tardive dyskinesia, Pick's disease, dysregulation of food intake including bulimia and anorexia nervosa, withdrawal symptoms associated with smoking cessation and dependant drug cessation, Gilles de la Tourette's Syndrome, age-related macular degeneration, glaucoma, neurodegeneration associated with glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Anxiety disorders (disorders with prominent anxiety or phobic avoidance), represent an area of umet medical needs in the treatment of psychiatric illness. See Diagnostic & Statistical Manual of Mental Disorders, IV (1994), pp 393–394, for various disease forms of anxiety.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Anxiety also includes post-traumatic stress disorder (PTSD), which is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat post traumatic stress disorder.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and atypical anti-psychotic drugs (also called an anti-psychotic agent). All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of Formula I can be prepared as shown in Scheme 1. The key step in the preparation of this class of compounds is the coupling of an azabicyclic moiety with the requisite acid chloride (Lv=Cl), mixed anhydride (e.g., Lv=diphenyl phosphoryl, bis(2-oxo-3-oxazolidinyl) phosphinyl, or acyloxy of the general formula of O—C(O)—$R_{Lv}$, where $R_{Lv}$ includes phenyl or t-butyl), or carboxylic acid (Lv=OH) in the presence of an activating reagent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as HATU).

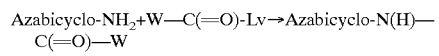

Azabicyclo-NH$_2$+W—C(=O)-Lv→Azabicyclo-N(H)—C(=O)—W    Scheme 1

Generally, to obtain compounds of Formula I, the carboxylic acid is activated with a uronium salt, preferably HATU (see *J. Am. Chem. Soc.*, 4397 (1993)), in the presence of the azabicyclic moiety and a base such as DIEA in DMF to afford the desired amides. Alternatively, the carboxylic acid is converted to the acyl azide by using DPPA; the appropriate amine precursor is added to a solution of the appropriate anhydride or azide to give the desired final compounds. In some cases, the ester (Lv being OMe or OEt)

may be reacted directly with the amine precursor in refluxing methanol or ethanol to give the compounds of Formula I.

Certain 6-substituted-[2.2.2]-3-amines (Azabicyclo I) are known in the art. The preparation of compounds where $R_2$ is present is described in *Acta Pol. Pharm.* 179–85 (1981). Alternatively, the 6-substituted-[2.2.2]-3-amine can be prepared by reduction of an oxime or an imine of the corresponding 6-substituted-3-quinuclidinone by methods known to one of ordinary skill in the art (see *J. Labelled Compds. Radiopharm.*, 53–60 (1995), *J. Med. Chem.* 988–995, (1998), *Synth. Commun.* 1895–1911 (1992), *Synth. Commun.* 2009–2015 (1996)). Alternatively, the 6-substituted-[2.2.2]-3-amine can be prepared from a 6-substituted-3-hydroxyquinuclidine by Mitsunobu reaction followed by deprotection as described in *Synth. Commun.* 1895–1911 (1995). Alternatively, the 6-substituted-[2.2.2]-3-amine can be prepared by conversion of a 6-substituted-3-hydroxyquinuclidine into the corresponding mesylate or tosylate, followed by displacement with sodium azide and reduction as described in *J. Med. Chem.* 587–593 (1975).

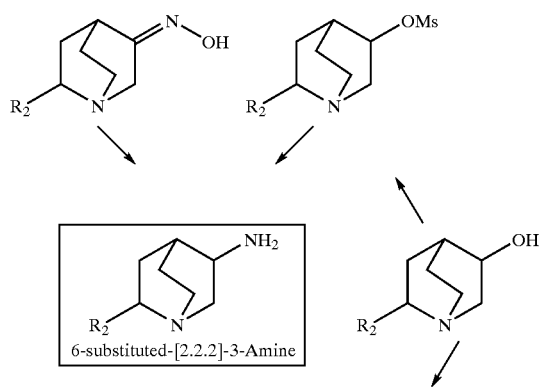

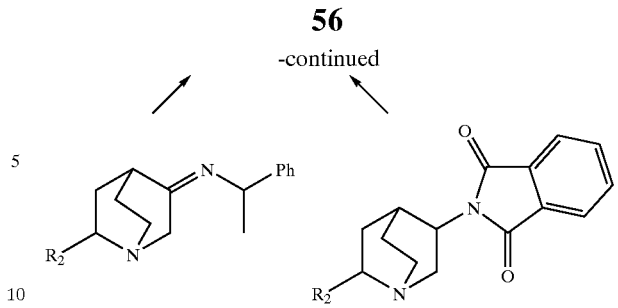

The oximes can be prepared by treatment of the 3-quinuclidinones with hydroxylamine hydrochloride in the presence of base. The imines can be prepared by treatment of the 3-quinuclidinones with a primary amine under dehydrating conditions. The 3-hydroxyquinuclidines can be prepared by reduction of the 3-quinuclidinones. The 6-substituted-3-quinuclidinones can be prepared by known procedures (see *J. Gen. Chem. Russia* 3791–3795, (1963), *J. Chem. Soc. Perkin Trans.* 1409–420 (1991), *J. Org. Chem.* 3982–3996 (2000)).

One of ordinary skill in the art will recognize that the methods described for the reaction of the unsubstituted 3-amino-1-azabicyclo[2.2.1]heptane ($R_2$=absent) are equally applicable to substituted compounds ($R_2 \neq H$). For where Azabicyclo is II, compounds where $R_2$ is present can be prepared from appropriately substituted nitro alcohols using procedures described in *Tetrahedron* (1997), 53, p. 11121 as shown below. Methods to synthesize nitro alcohols are well known in the art (see *J. Am. Chem. Soc.* (1947), 69, p 2608). The scheme below is a modification of the synthesis of exo-3-amino-1-azabicyclo[2.2.1]heptane as the bis(hydro para-toluenesulfonate) salt, described in detail herein, to show how to obtain these amine precursors. The desired salt can be made using standard procedures.

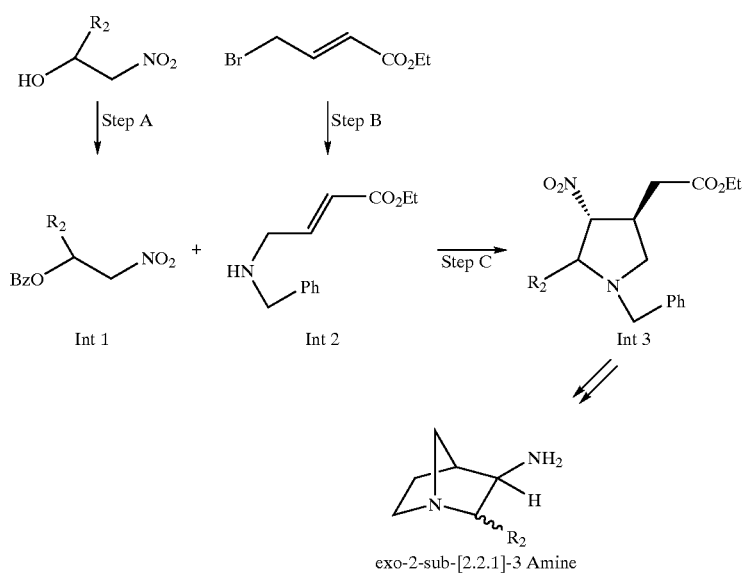

Compounds for Azabicyclo II where $R_2$ is present can also be prepared by modification of intermediates described in the synthesis of exo-3-amino-1-azabicyclo[2.2.1]heptane as the bis(hydro para-toluenesulfonate) salt, described in detail herein. For example, Int 6 can be oxidized to the aldehyde and treated with an organometallic reagent to provide Int 20 using procedures described in *Tetrahedron* (1999), 55, p 13899. Int 20 can be converted into the amine using methods described for the synthesis of exo-3-amino-1-azabicyclo[2.2.1]heptane as the bis(hydro para-toluenesulfonate) salt. Once the amine is obtained, the desired salt can be made using standard procedures.

The schemes used are for making exo-3-amino-1-azabicyclo[2.2.1]heptane. However, the modifications discussed are applicable to make the endo isomer also.

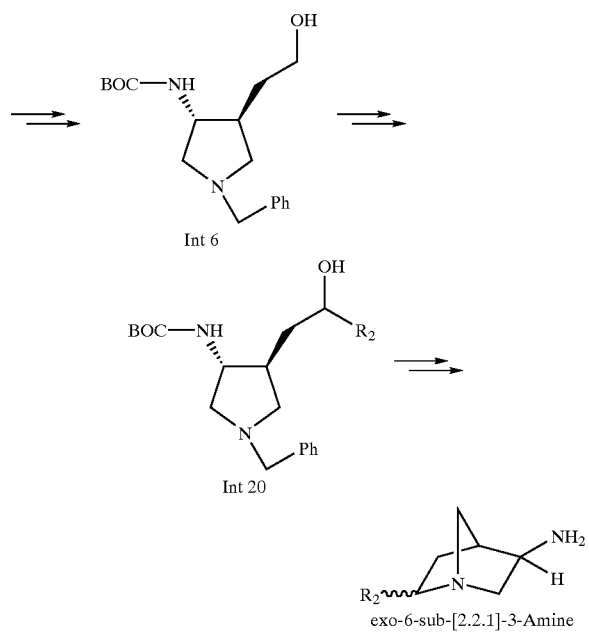

Int 6

Int 20 exo-6-sub-[2.2.1]-3-Amine

There are several methods by which the amine precursor for Azabicyclo III and Azabicyclo IV can be obtained:

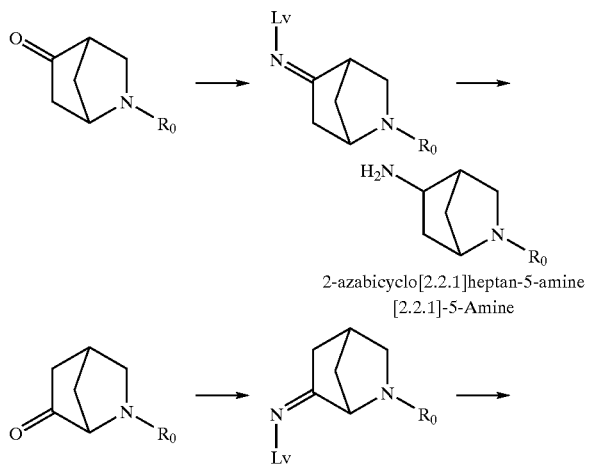

2-azabicyclo[2.2.1]heptan-5-amine
[2.2.1]-5-Amine

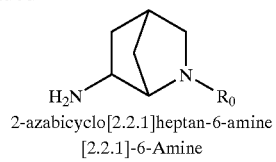

2-azabicyclo[2.2.1]heptan-6-amine
[2.2.1]-6-Amine where Lv can be —$CH_2Ph$, —$CH(Me)Ph$, —OH, —OMe, or —$OCH_2Ph$. The respective amine precursors for Azabicyclo III and Azabicyclo IV can be prepared by reduction of an oxime or an imine of the corresponding N-2-azabicyclo[2.2.1]-heptanone by methods known to one skilled in the art (see *J. Labelled Compds. Radiopharm.*, 53–60 (1995), *J. Med. Chem.* 988–995, (1998), *Synth. Commun.* 1895–1911 (1992), *Synth. Commun.* 2009–2015 (1996)). The oximes can be prepared by treatment of the N-2-azabicyclo[2.2.1] heptanones with hydroxylamine hydrochloride in the presence of a base. The imines can be prepared by treatment of the N-2-azabicyclo[2.2.1]-heptanones with a primary amine under dehydrating conditions. The N-2-azabicyclo[2.2.1] heptanones can be prepared by known procedures (see *Tet. Lett.* 1419–1422 (1999), *J. Med. Chem.* 2184–2191 (1992), *J. Med. Chem.* 706–720 (2000), *J. Org. Chem.*, 4602–4616 (1995)).

The exo- and endo-1-azabicyclo[3.2.1]octan-3-amines are prepared from 1-azabicyclic[3.2.1]octan-3-one (Thill, B. P., Aaron, H. S., *J. Org. Chem.*, 4376–4380 (1968)) according to the general procedure as discussed in Lewin, A. H., et al., *J. Med. Chem.*, 988–995 (1998).

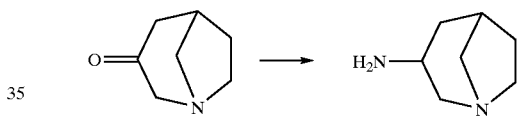

One of ordinary skill in the art will also recognize that the methods described for the reaction of the unsubstituted 1-azabicyclo[3.2.1]octan-3-amine or 1-azabicyclo[3.2.2] nonan-3-amine ($R_2$=absent) are equally applicable to substituted compounds ($R_2$ present). The $R_2$ substituent may be introduced as known to one skilled in the art through standard alkylation chemistry. Exposure of 1-azabicyclo [3.2.1]octan-3-one or 1-azabicyclo[3.2.2]nonan-3-one to a hindered base such as LDA (lithium diisopropylamide) in a solvent such as THF or ether between 0° C. to −78° C. followed by the addition of an alkylating agent ($R_2Lv$, where Lv=Cl, Br, I, OTs, etc.) will, after being allowed to warm to about 0° C. to rt followed by an aqueous workup, provide the desired compound as a mixture of isomers. Chromatographic resolution (flash, HPLC, or chiral HPLC) will provided the desired purified alkylated ketones. From there, formation of the oxime and subsequent reduction will provide the desired endo or exo isomers.

It will be apparent to those skilled in the art that the requisite carboxylic acids are either commercially available or can be obtained through synthesis via literature procedures or through the slight modification thereof.

When W is furan, oxazole, pyrrole, 5-thiazole, or thiophene, the carboxylic acid is activated with a uronium salt, preferably HATU, in the presence of the azabicyclic moiety and a base such as DIEA in DMF to afford the desired amides. In the case where W is a 2-thiazole, or 2-oxazole, the amide bond is formed by the reaction of the amine and ester (Lv=OEt) in an alcoholic solvent (see *Liebigs Ann. Chem.*, 1216–1231 (1980)).

The thiophene carboxylic acids required in Examples 3, 16–18 can be synthesized from the corresponding aldehydes by oxidation with NaClO$_2$ as described in *J. Org. Chem.*, (1980), 45, 1176. The requisite aldehydes can be made as described in *J. Med. Chem.*, 1585–1599 (1997). An aryl boronic acid is reacted with a bromothiophene in the presence of a palladium (0) source, such as tetrakis-(triphenylphosphine)palladium (0), and a base, preferably aqueous sodium carbonate. The reaction works best if heated at reflux in THF/water for 24 hr. The thiophene carboxylic acids of Examples 6–10 are prepared by similar methods as in Example 3 with modifications as described herein. The furan and thiophene carboxylic acids required for Examples 1, 2, and 11 are available commercially.

Scheme 2

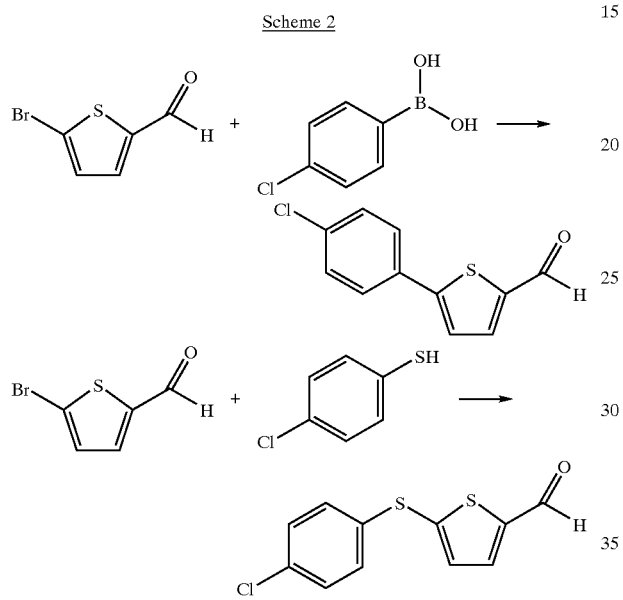

The thiophene carboxylic acids for Examples 12–13 are synthesized from the corresponding esters by base catalyzed hydrolysis. Typical hydrolysis procedures are well known in the art. Preferably, the thiophene ester is treated with aqueous lithium hydroxide in a solvent such as dioxane. The esters are commercially available. The thiophene carboxylic acid for Example 14 is synthesized by a two-step sequence beginning with reaction of a bromothiophene-carbaldehyde with the appropriate thiophenol or phenol as described in *Coll. Czech. Chem. Commun.*, 2360–2363 (1980). Namely, the sodium salt of the thiophenol or phenol is formed by treatment with a strong base like sodium hydride. The sodium salt is then reacted with a bromothiophene in a solvent such as acetone. The thiophene-carbaldehydes are oxidized to the corresponding carboxylic acids by treating with sodium chlorite as described in *J. Org. Chem.* (1980) 45, 1176. The carboxylic acid for Example 15 is made using the same general procedure, making non-critical changes.

When W is thiazole, the required acid for Example 19 is prepared by nucleophilic addition of the requisite phenol or thiophenol to the ethyl 2-bromo-1,3-thiazole-5-carboxylate according to the procedure described in *Helv. Chim. Acta.*, 2002–2022 (1997). Preferably, in EtOH utilizing K$_2$CO$_3$ as a base (Scheme 3). The esters are hydrolyzed to the corresponding carboxylic acids by procedures well known in the art. The 2-bromo-1,3-thiazole is prepared by the method described in *Roczniki Chemii Ann. Soc. Chim. Polonorum*, 1647–1658 (1972). The aryl 1,3-thiazole for Example 20 is prepared according to the procedure of Huntress and Pfister in *J. Am. Chem. Soc.*, 2167–2169 (1943). The 1,3-thiazole-5-carboxylic acid required in Example 21 can be synthesized from the corresponding esters by base hydrolysis via procedures well known in the art. The requisite esters can be prepared by a Suzuki reaction as described in *J. Med. Chem.*, 4985–92 (1995). An aryl boronic acid is reacted with a bromothiazole ester in the presence of a palladium (0) source, such as tetrakis-(triphenylphosphine)palladium (0), and a base, preferably aqueous sodium carbonate.

Scheme 3

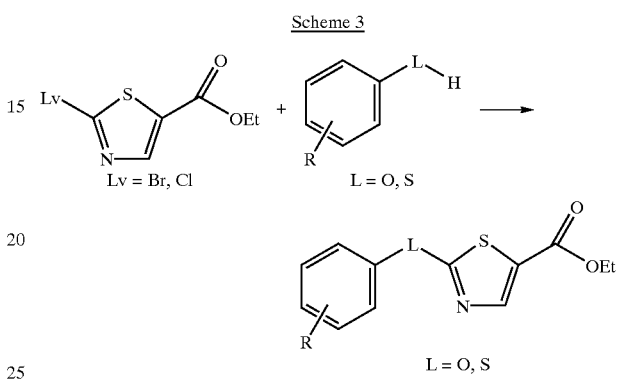

The 5-substituted-1,3-oxazole-2-ester for Example 23 is synthesized according to procedures described in *J. Pharm. Soc. Japan*, 305–7 (1956) as shown in Scheme 4. The 5-substituted-1,3-thiazole-2-ester for Example 24 is synthesized according to procedures described in *Chem. Pharm. Bull.*, 4195–4198 (1982).

Scheme 4

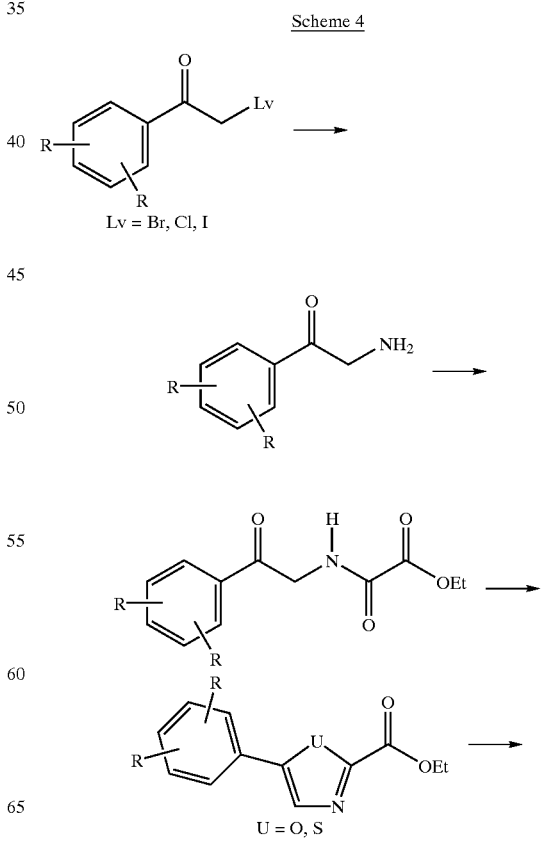

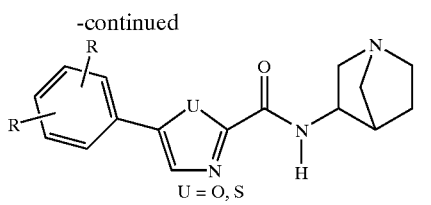

The furans for Examples 25–28 are commercially available or can be prepared from their corresponding aldehydes by oxidation or esters by reduction as described for Example 3. In the event that the furan is not commercially available, it can be prepared by the method of Bussolari and Rehborn described in *Org. Lett.* 965–7 (1999). Furan Examples 29–30 are prepared in a convergent means by a direct palladium catalyzed Suzuki coupling of, for example, N-[1-azabicyclo[2.2.1]hept-3-yl]-5-bromo-furan-2-carboxamide, with the requisite boronic acid by the method described in *Org. Lett.* 965–7 (1999), to yield directly the desired aryl amides (Scheme 5).

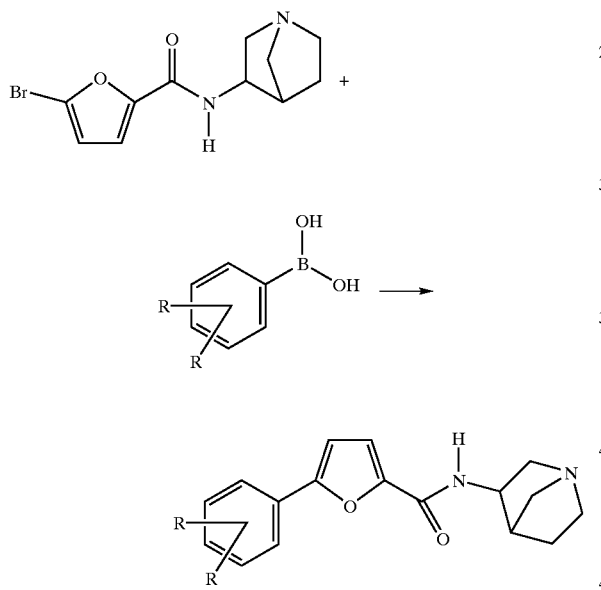

One of ordinary skill in the art would recognize that Examples 4, and 31 are prepared by reduction of the corresponding aryl nitro compounds by methods well known in the art, preferably by reduction with Pd/C in an alcoholic solvent such as EtOH under $H_2$. The carboxylic acid for Example 32 is prepared by a Pd(0) catalyzed Sonogashira coupling of 5-bromo-2-furaldehyde and phenyl acetylene as described in *Tetrahedron Lett.*, 4467–70 (1975). The resulting aldehyde is converted to the desired analog by methods as described for Example 25. Example 33 is prepared by addition of the sodium salt of phenol to N-[exo-4(S)-1-azabicyclo[2.2.1]hept-3-yl]-5-bromo-furan-2-carboxamide. The requisite acid for Example 34 is prepared by bromination of methyl-5-bromo-1-methyl-1H-pyrrole-2-carboxylate, followed by similar Pd-catalyzed coupling as described for Example 3.

The 1,3-oxazole-2-carboxylic acid required for Example 35 is prepared by the method described in *J. Pharm. Sci. Japan* 305–7, (1956). The 2-phenyl-1,3-oxazole-5-carboxylic acid required for Example 36 is prepared by the method described in *Chem. Heterocycl. Compd.* (Engl.Transl.), 654–663, (1986). 2-Phenyl-1,3-oxazole-4-carboxylic acid required for Example 37 is prepared as described by Korte and Stoeriko, in *Chem. Ber.*, 1033–1042, (1960). The 5-phenylisoxazole-3-carboxylic acid for Example 38 is prepared by the method of Vaughan and Spencer as described in *J. Org. Chem.* 1160–4, (1960).

Thioamides, such as Example 39, can be prepared from the requisite thioester by direct displacement of the thioester with an aminoazabicyclic compound. The thioester can be prepared as described in *J. Organometallic Chem.*, 95–98 (1987). One of ordinary skill in the art would quickly identify that compounds such as Example 39 could also be prepared directly from the amides exemplified throughout this patent by direct treatment with a reagent such and Lawesson's reagent (see Lawesson et. al. in *Bull. Soc. Chim. Belg.*, 229 (1978)) or $P_4S_{10}$ (see *Chem. Rev.*, 45 (1961)). Alternatively one can react a dithiocarboxylic ester with the corresponding amino-azabicyclo compound to form the same thioamide.

Preparation of the 2.2.1 Amines

Synthesis of exo-3-amino-1-azabicyclo[2.2.1]heptane as the bis(hydro para-toluenesulfonate) salt

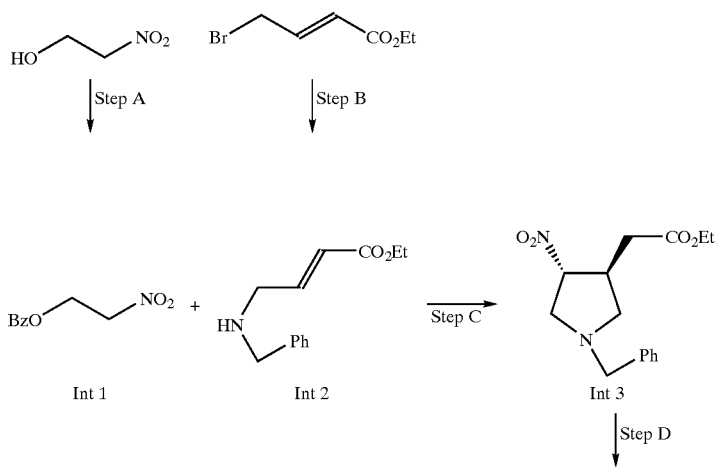

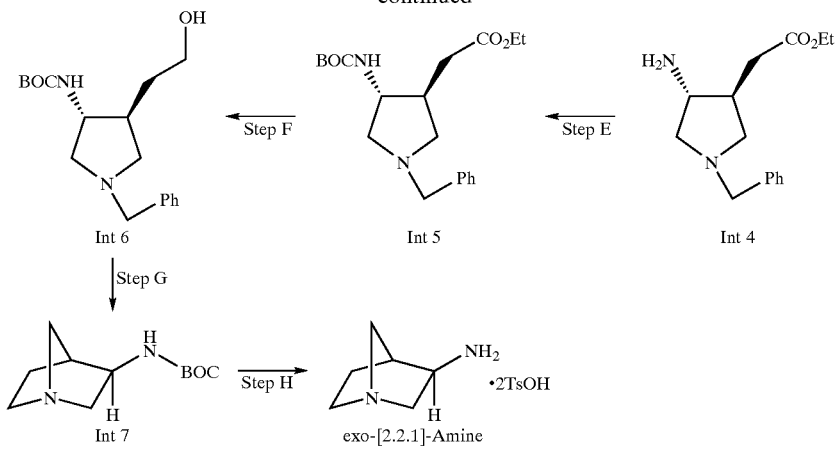

Step A. Preparation of 2-(benzoyloxy)-1-nitroethane (Int 1).

Benzoyl chloride (14.9 mL, 128 mmol) is added to a stirred solution of nitroethanol (9.2 mL, 128 mmol) in dry benzene (120 mL). The solution is refluxed for 24 hr and then concentrated in vacuo. The crude product is purified by flash chromatography on silica gel. Elution with hexanes-EtOAc (80:20) affords Int 1 as a white solid (68% yield): $^1$H NMR (CDCl$_3$) δ 8.0, 7.6, 7.4, 4.9, 4.8.

Step B. Preparation of ethyl E-4-(benzylamino)-2-butenoate (Int 2).

Ethyl E-4-bromo-2-butenoate (10 mL, 56 mmol, tech grade) is added to a stirred solution of benzylamine (16 mL, 146 mmol) in CH$_2$Cl$_2$ (200 mL) at rt. The reaction mixture stirs for 15 min, and is diluted with ether (1 L). The mixture is washed with saturated aqueous NaHCO$_3$ solution (3×) and water, dried over Na$_2$SO$_4$, filtered and concentrated in vacuo. The residue is purified by flash chromatography on silica gel. Elution with hexanes-EtOAc (70:30) affords Int 2 as a clear oil (62% yield): $^1$H NMR (CDCl$_3$) δ 7.4–7.2, 7.0, 6.0, 4.2, 3.8, 3.4, 2.1–1.8, 1.3.

Step C. Preparation of trans-4-nitro-1-(phenylmethyl)-3-pyrrolidineacetic acid ethyl ester (Int 3).

A solution of Int 1 (6.81 g, 34.9 mmol) and Int 2 (7.65 g, 34.9 mmol) in EtOH (70 mL) stirs at rt for 15 h and is then concentrated in vacuo. The residue is diluted with ether (100 mL) and saturated aqueous NaHCO$_3$ solution (100 mL). The organic layer is separated and dried over Na$_2$SO$_4$, filtered and concentrated in vacuo. The crude product is purified by flash chromatography on silica gel. Elution with hexanes-EtOAc (85:15) affords Int 3 as a clear oil (76% yield): $^1$H NMR (CDCl$_3$) δ 7.4–7.3, 4.8–4.7, 4.1, 3.8–3.6, 3.3–3.0, 2.7–2.6, 2.4–2.3, 1.2.

Step D. Preparation of trans-4-amino-1-(phenylmethyl)-3-pyrrolidineacetic acid ethyl ester (Int 4).

A mixture of Int 3 (3.28 g, 11.2 mmol) and RaNi (1.5 g) in EtOH (100 mL) is placed in a Parr bottle and hydrogenated for 4 h under an atmosphere of hydrogen (46 psi) at rt. The mixture is filtered through a pad of Celite, and the solvent is removed in vacuo to afford Int 4 as a clear oil (100% yield): $^1$H NMR (300 MHz, CDCl$_3$) δ 7.3–7.2, 4.1, 3.6, 3.2, 3.0–2.9, 2.8, 2.8–2.6, 2.6–2.4, 2.30–2.2, 1.2.

Step E. Preparation of trans-4-(1,1-dimethylethoxycarbonylamido)-1-(phenylmethyl)-3-pyrrolidineacetic acid ethyl ester (Int 5).

Di-tert-butyldicarbonate (3.67 g, 16.8 mmol) is added to a stirred solution of Int 4 (2.94 g, 11.2 mmol) in CH$_2$Cl$_2$ (30 mL) cooled in an ice bath. The reaction is allowed to warm to rt and stirred overnight. The mixture is concentrated in vacuo. The crude product is purified by flash chromatography on silica gel. Elution with hexanes-EtOAc (80:20) affords Int 5 as a white solid (77% yield): $^1$H NMR (300 MHz, CDCl$_3$) δ 7.4–7.2, 5.1–4.9, 4.1, 4.0–3.8, 3.6, 3.2–3.0, 2.8–2.6, 2.5–2.4, 2.3–2.1, 1.4, 1.3.

Step F. Preparation of trans (tert-butoxycarbonylamino)-4-(2-hydroxyethyl)-1-(N-phenylmethyl) pyrrolidine (Int 6).

LiAlH$_4$ powder (627 mg, 16.5 mmol) is added in small portions to a stirred solution of Int 5 (3.0 g, 8.3 mmol) in anhydrous THF (125 mL) in a −5° C. bath. The mixture is stirred for 20 min in a −5° C. bath, then quenched by the sequential addition of water (0.6 mL), 15% (w/v) aqueous NaOH (0.6 mL) and water (1.8 mL). Excess anhydrous K$_2$CO$_3$ is added, and the mixture is stirred for 1 h, then filtered. The filtrate is concentrated in vacuo. The residue is purified by flash chromatography on silica gel. Elution with EtOAc affords Int 6 as a white solid (94% yield): $^1$H NMR (CDCl$_3$) δ 7.4–7.3, 5.3–5.2, 4.1–4.0, 3.9–3.7, 3.3–3.2, 2.8–2.7, 2.3–2.1, 1.7, 1.5.

Int 6 is a racemic mixture that can be resolved via chromatography using a Diacel chiral pack AD column. From the two enantiomers thus obtained, the (+)-enantiomer, $[\alpha]^{25}_D$+35 (c 1.0, MeOH), gives rise to the corresponding enantiomerically pure exo-4-S final compounds, whereas the (−)-enantiomer, $[\alpha]^{25}_D$−34 (c 0.98, MeOH), gives rise to optically pure exo-4-R final compounds. The methods described herein use the (+)-enantiomer of Int 6 to obtain the optically pure exo-4-S final compounds. However, the methods used are equally applicable to the (−)-enantiomer of Int 6, making non-critical changes to the methods provided herein to obtain the optically pure exo-4-R final compounds.

Step G. Preparation of exo 3-(tert-butoxycarbonylamino)-1-azabicyclo[2.2.1]heptane (Int 7).

TEA (8.0 g, 78.9 mmol) is added to a stirred solution of Int 6 (2.5 g, 7.8 mmol) in CH$_2$Cl$_2$ (50 mL), and the reaction is cooled in an ice-water bath. CH$_3$SO$_2$Cl (5.5 g, 47.8 mmol) is then added dropwise, and the mixture is stirred for 10 min in an ice-water bath. The resulting yellow mixture is diluted with saturated aqueous NaHCO$_3$ solution, extracted with CH$_2$Cl$_2$ several times until no product remains in the aqueous layer by TLC. The organic layers are combined, washed with brine, dried over Na$_2$SO$_4$ and concentrated in vacuo. The residue is dissolved in EtOH (85 mL) and is heated to reflux for 16 h. The reaction mixture is allowed to cool to rt, transferred to a Parr bottle and treated with 10% Pd/C catalyst (1.25 g). The bottle is placed under an atmosphere of hydrogen (53 psi) for 16 h. The mixture is filtered through Celite, and fresh catalyst (10% Pd/C, 1.25 g) is added. Hydrogenolysis continues overnight. The process is repeated three more times until the hydrogenolysis is complete. The final mixture is filtered through Celite and concentrated in vacuo. The residue is purified by flash chromatography on silica gel. Elution with CHCl$_3$—MeOH—NH$_4$OH (90:9.5:0.5) affords Int 7 as a white solid (46% yield): $^1$H NMR (CDCl$_3$) δ 5.6–5.5, 3.8–3.7, 3.3–3.2, 2.8–2.7, 2.0–1.8, 1.7–1.5, 1.5.

Step H. Preparation of exo-3-amino-1-azabicyclo[2.2.1] heptane bis(hydro-para-toluenesulfonate).

Para-toluenesulfonic acid monohydrate (1.46 g, 7.68 mmol) is added to a stirred solution of Int 7 (770 mg, 3.63 mmol) in EtOH (50 mL). The reaction mixture is heated to reflux for 10 h, followed by cooling to rt. The precipitate is collected by vacuum filtration and washed with cold EtOH to give exo-[2.2.1]-Amine as a white solid (84% yield): $^1$NMR (CD$_3$OD) δ 7.7, 7.3, 3.9–3.7, 3.7–3.3, 3.2, 2.4, 2.3–2.2, 1.9–1.8. The corresponding amines can be obtained by using the resolved Int 6 to give exo-(4R)-[2.2.1]-3-Amine and exo-(4S)-[2.2.1]-3-Amine.

Synthesis of endo-3-amino-1-azabicyclo[2.2.1] heptane as the bis(hydro para-toluenesulfonate) salt is recrystallized from EtOAc to afford Int 10 as a yellow solid (38% yield): $^1$H NMR (CDCl$_3$) δ 11.4, 7.4, 4.3, 3.4, 2.6, 1.3.

Step J. Preparation of ethyl cis-3-hydroxy-2-oxopiperidine-4-carboxylate (Int 11).

A mixture of Int 10 (15 g, 81 mmol) and 5% rhodium on carbon (2.0 g) in glacial acetic acid is placed under an atmosphere of hydrogen (52 psi). The mixture is shaken for 72 h. The mixture is filtered through Celite, and the filtrate is concentrated in vacuo to afford Int 11 as a white solid (98% yield): $^1$H NMR (CDCl$_3$) δ 6.3, 4.2, 4.0–3.8, 3.4, 3.3–3.2, 2.2, 1.3.

Step K. Preparation of cis-4-(hydroxymethyl)piperidin-3-ol (Int 12).

Int 11 (3.7 g, 19.9 mmol) as a solid is added in small portions to a stirred solution of LiAlH$_4$ in THF (80 mL of a 1.0 M solution) in an ice-water bath. The mixture is warmed to rt, and then the reaction is heated to reflux for 48 h. The mixture is cooled in an ice-water bath before water (3.0 mL, 170 mmol) is added dropwise, followed by the sequential addition of NaOH (3.0 mL of a 15% (w/v) solution) and water (9.0 mL, 500 mmol). Excess K$_2$CO$_3$ is added, and the mixture is stirred vigorously for 15 min. The mixture is filtered, and the filtrate is concentrated in vacuo to afford Int 12 as a yellow powder (70% yield): $^1$H NMR (DMSO-d$_6$) δ 4.3, 4.1, 3.7, 3.5–3.2, 2.9–2.7, 2.5–2.3, 1.5, 1.3.

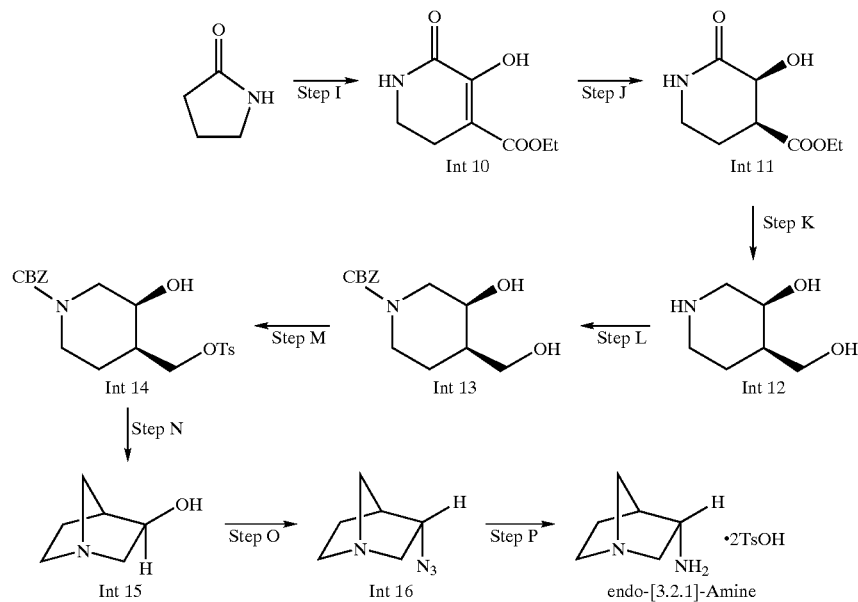

Step I. Preparation of ethyl 5-hydroxy-6-oxo-1,2,3,6-tetrahydropyridine-4-carboxylate (Int 10).

Absolute EtOH (92.0 mL, 1.58 mol) is added to a mechanically stirred suspension of potassium ethoxide (33.2 g, 395 mmol) in dry toluene (0.470 L). When the mixture is homogeneous, 2-pyrrolidinone (33.6 g, 395 mmol) is added, and then a solution of diethyl oxalate (53.1 mL, 390 mmol) in toluene (98 mL) is added via an addition funnel. After complete addition, toluene (118 mL) and EtOH (78 mL) is added sequentially. The mixture is heated to reflux for 18 h. The mixture is cooled to rt and aqueous HCl (150 mL of a 6.0 M solution) is added. The mixture is mechanically stirred for 15 min. The aqueous layer is extracted with CH$_2$Cl$_2$, and the combined organic layers are dried over MgSO$_4$, filtered and concentrated in vacuo to a yellow residue. The residue Step L. Preparation of benzyl cis-3-hydroxy-4-(hydroxymethyl)piperidine-1-carboxylate (Int 13).

N-(benzyloxy carbonyloxy)succinimide (3.04 g, 12.2 mmol) is added to a stirred solution of Int 12 (1.6 g, 12.2 mmol) in saturated aqueous NaHCO$_3$ (15 mL) at rt. The mixture is stirred at rt for 18 h. The organic and aqueous layers are separated. The aqueous layer is extracted with ether (3×). The combined organic layers are dried over anhydrous K$_2$CO$_3$, filtered and concentrated in vacuo to afford Int 13 as a yellow oil (99% yield): $^1$H NMR (CDCl$_3$) δ 7.4–7.3, 5.2, 4.3, 4.1, 3.8–3.7, 3.0–2.8, 2.1, 1.9–1.7, 1.4.

Step M. Preparation of benzyl cis-3-hydroxy-4-[(4-methylphenyl)sulfonyl oxymethyl]piperidine-1-carboxylate (Int 14).

Para-toluenesulfonyl chloride (1.0 g, 5.3 mmol) is added to a stirred solution of Int 13 (3.6 g, 5.3 mmol) in pyridine (10 mL) in a −15° C. bath. The mixture is stirred for 4 h, followed by addition of HCl (4.5 mL of a 6.0 M solution). CH$_2$Cl$_2$ (5 mL) is added. The organic and aqueous layers are separated. The aqueous layer is extracted with CH$_2$Cl$_2$. The combined organic layers are washed with brine, dried over MgSO$_4$, filtered and concentrated in vacuo to afford Int 14 as a colorless oil (78% yield): $^1$H NMR (CDCl$_3$) δ 7.8, 7.4–7.2, 5.1, 4.3–4.2, 4.1, 3.9–3.8, 2.9–2.7, 2.4, 1.9, 1.6–1.3.
Step N. Preparation of exo-1-azabicyclo[2.2.1]heptan-3-ol (Int 15).

A mixture of Int 14 (3.6 g, 8.6 mmol) and 10% Pd/C catalyst (500 mg) in EtOH (50 mL) is placed under an atmosphere of hydrogen. The mixture is shaken for 16 h. The mixture is filtered through Celite. Solid NaHCO$_3$ (1.1 g, 13 mmol) is added to the filtrate, and the mixture is heated in an oil bath at 50° C. for 5 h. The solvent is removed in vacuo. The residue is dissolved in saturated aqueous K$_2$CO$_3$ solution. Continuous extraction of the aqueous layer using a liquid-liquid extraction apparatus (18 h), followed by drying the organic layer over anhydrous K$_2$CO$_3$ and removal of the solvent in vacuo affords Int 15 as a white solid (91% yield): $^1$H NMR δ 3.8, 3.0–2.8, 2.6–2.5, 2.4–2.3, 1.7, 1.1.
Step O. Preparation of endo-3-azido-1-azabicyclo[2.2.1] heptane (Int 16).

To a mixture of Int 15 (1.0 g, 8.9 mmol) and triphenyl phosphine (3.0 g, 11.5 mmol) in toluene-THF (50 mL, 3:2) in an ice-water bath are added sequentially a solution of hydrazoic acid in toluene (15 mL of ca. 2 M solution) and a solution of diethyl azadicarboxylate (1.8 mL, 11.5 mmol) in toluene (20 mL). The mixture is allowed to warm to rt and stir for 18 h. The mixture is extracted with aqueous 1.0 M HCl solution. The aqueous layer is extracted with EtOAc, and the combined organic layers are discarded. The pH of the aqueous layer is adjusted to 9 with 50% aqueous NaOH solution. The aqueous layer is extracted with CH$_2$Cl$_2$ (3×), and the combined organic layers are washed with brine, dried over Na$_2$SO$_4$, filtered and concentrated in vacuo. The crude product is purified by flash chromatography on silica gel. Elution with CHCl$_3$—MeOH—NH$_4$OH (92:7:1) affords Int 16 as a colorless oil (41% yield): $^1$H NMR (CDCl$_3$) δ 4.1, 3.2, 2.8, 2.7–2.5, 2.2, 1.9, 1.5.
Step P. Preparation of endo-3-amino-1-azabicyclo[2.2.1] heptane bis(hydro-para-toluenesulfonate).

A mixture of Int 16 (250 mg, 1.8 mmol) and 10% Pd/C catalyst (12 mg) in EtOH (10 mL) is placed under an atmosphere of hydrogen (15 psi). The mixture is stirred for 1 h at rt. The mixture is filtered through Celite, and the filtrate is concentrated in vacuo. The residue is dissolved in EtOH (10 mL) and para-toluenesulfonic acid monohydrate (690 mg, 3.7 mmol) is added. The mixture is stirred for 30 min, and the precipitate is filtered. The precipitate is washed sequentially with cold EtOH and ether. The precipitate is dried in vacuo to afford endo-[2.2.1]-Amine as a white solid (85% yield): $^1$H NMR (CD$_3$OD) δ 7.7, 7.3, 4.2, 3.9, 3.6–3.4, 3.3–3.2, 2.4, 2.3, 2.1.

Preparation of the 3.2.1-Amine exo-1-Azabicyclo[3.2.1]octan-3-amine dihydrochloride (exo-[3.2.1]-Amine)

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with CH$_2$Cl$_2$, treated with charcoal, filtered and evaporated. The resulting material is taken up in 1-propanol (45 mL) and heated in a 100° C. oil bath. The solution is treated with sodium metal (6.4 g in portions). Heating is continued for 3 h and the mixture cooled to rt. Water is added carefully and the organic layer is extracted, dried (MgSO$_4$), filtered, acidified with MeOH/HCl(g), and evaporated. 2-Propanol is added and the resulting solid is filtered and dried in vacuo to give exo-[3.2.1]-Amine in 49% yield. MS for C$_7$H$_{14}$N$_2$.(HCl)$_2$ (ESI)(M+H)$^+$ m/z=127.

Endo-1-Azabicyclo [3.2.1]octan-3-amine dihydrochloride (Endo-[3.2.1]-Amine)

A mixture of 1-azabicyclo[3.2.1]octan-3-one hydrochloride (2.80 g, 17.3 mmol), ethanol (25 mL), and hydroxylamine hydrochloride (1.56 g, 22.4 mmol) is treated with sodium acetate trihydrate (7.07 g, 51.2 mmol). The mixture is stirred for 3 h and evaporated in vacuo. The residue is diluted with CH$_2$Cl$_2$, treated with charcoal, filtered and evaporated. The resulting oxime (3.1 mmol) is treated with acetic acid (30 mL) and hydrogenated at 50 psi over PtO$_2$ (50 mg) for 12 h. The mixture is then filtered and evaporated. The residue is taken up in a minimal amount of water (6 mL) and the pH is adjusted to >12 using solid NaOH. The mixture is then extracted with ethyl acetate (4×25 mL), dried over MgSO$_4$, filtered, treated with ethereal HCl, and evaporated to give endo-[3.2.1]-Amine.

1-Azabicyclo[3.2.1]octan-3-amine:

Preparation of the 3R,5R-[3.2.1]-Amine

This amine can also be prepared according to the following method:

(3S)-1-[(S)-1-Phenethyl]-5-oxo-3-pyrrolidine-carboxylic acid

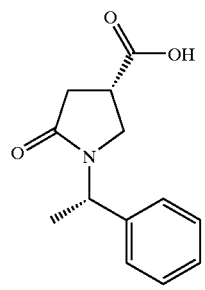

According to the literature procedure (Nielsen et al. J. Med. Chem 1990, 70–77), a mixture of itaconic acid (123.17 g, 946.7 mmol) and (S)-(−)-α-methyl benzylamine (122.0 mL, 946.4 mmol) are heated (neat) in a 160° C. oil bath for 4 h. Upon cooling, MeOH (~200 mL) is added and the resulting solid collected by filtration. The solid is treated with EtOH (~700 mL) and warmed using a steam bath until ~450 mL solvent remained. After cooling to rt, the solid is collected and dried to afford 83.2 g as a crystalline solid: [α]$^{25}_D$=−80 (c 0.97, DMSO). $^1$H NMR (400 MHz, DMSO-d$_6$) δ 12.66, 7.20–7.40, 5.23, 3.40–3.55, 3.10–3.25, 2.40–2.65, 1.45; MS (EI) m/z 233 (M$^+$).

(3S)-1-[(S)-1-Phenethyl]-3-(hydroxymethyl) pyrrolidine

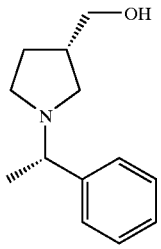

A suspension (3S)-1-[(S)-1-phenethyl]-5-oxo-3-pyrrolidine-carboxylic acid (82.30 g, 352.8 mmol) in Et₂O (200 mL) is added in small portions to a slurry of LiAlH₄ (17.41 g, 458.6 mmol) in Et₂O (700 mL). The mixture begins to reflux during the addition. The addition funnel containing the suspension is rinsed with Et₂O (2×50 mL), and the mixture is heated in a 50° C. oil bath for an additional 2 h and first allowed to cool to rt and then further cooled using an ice bath. The mixture is carefully treated with H₂O (62 mL). The resulting precipitate is filtered, rinsed with Et₂O, and discarded. The filtrate is concentrated to a yellow oil. When EtOAc is added to the oil, a solid began to form. Hexane is then added, and the mixture is filtered and the solid is dried to afford 43.3 g. [α]$^{25}_D$=−71 (c 0.94, CHCl₃); ¹H NMR (400 MHz, CDCl₃) δ 7.20–7.45, 3.60–3.70, 3.40–3.60, 3.19, 3.05–3.15, 2.35–2.55, 2.25–2.35, 1.95–2.10, 1.75–1.90, 1.42; HRMS (FAB) calcd for C₁₃H₁₉NO (MH⁺) 206.1545, found 206.1532.

(3R)-1-[(S)-1-Phenethyl]-3-(cyanomethyl) pyrrolidine

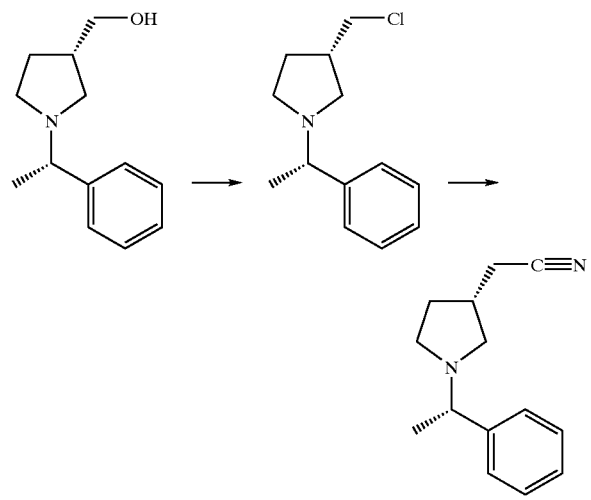

A solution of (3S)-1-[(S)-1-phenethyl]-3-(hydroxymethyl)pyrrolidine (42.75 g, 208.23 mmol) in chloroform (350 mL) is heated to reflux under N₂. The solution is treated with a solution of thionyl chloride (41.8 mL, 573 mmol) in chloroform (40 mL) dropwise over 45 min. The mixture is stirred for an additional 30 min, is cooled and concentrated. The residue is diluted with H₂O (~200 mL), 1 N NaOH is added until a pH~8 (pH paper). A small portion (~50 mL) of sat. NaHCO₃ is added and the basic mixture is extracted with EtOAc (3×400 mL), washed with brine, dried over MgSO₄, filtered and concentrated to give 46.51 g of (3S)-1-[(S)-1-phenethyl]-3-(chloromethyl)pyrrolidine: MS (ESI+) m/z 224.2 (MH⁺). The chloride (46.35 g, 208.0 mmol) is transferred to a flask, DMSO (200 mL) is added, and the solution is treated with NaCN (17.84 g, 363.9 mmol). The mixture is heated under N₂ in a 100° C. oil bath overnight and is cooled. The brown mixture is poured into H₂O (300 mL) and is extracted with EtOAc (1000 mL in portions). The combined organic layer is washed with H₂O (6×~50 mL), brine (~100 mL), dried (MgSO₄), filtered and concentrated to give 40.61 g of an oil: ¹H NMR (400 MHz, CDCl₃) δ 7.20–7.40, 3.26, 2.70–2.85, 2.40–2.60, 2.27, 2.10–2.20, 1.50–1.70, 1.41; MS (ESI+) for m/z 215.2 (M+H⁺).

(3R)-Methyl 1-[(S)-1-phenylethyl]pyrrolidine-3-acetate

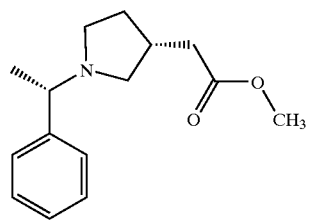

Acetyl chloride (270 mL, 3.8 mol) is carefully added to a flask containing chilled (0° C.) methanol (1100 mL). After the addition is complete, the acidic solution is stirred for 45 min (0° C.) and then (3R)-1-[(S)-1-phenethyl]-3-(cyanomethyl)pyrrolidine (40.50 g, 189.0 mmol) in methanol (200 mL) is added. The ice bath is removed and the mixture is stirred for 100 h at rt. The resulting suspension is concentrated. Water (~600 mL) is added, the mixture stirred for 45 min and then the pH is adjusted (made basic) through the addition of ~700 mL sat. aq. NaHCO₃. The mixture is extracted with EtOAc (3×300 mL). The combined organic layers are washed with brine, dried (MgSO₄), filtered through celite and concentrated to give 36.86 g as an oil: ¹H NMR (400 MHz, CDCl₃) δ 7.20–7.40, 3.69, 3.30–3.40, 2.85–2.95, 2.40–2.70, 2.00–2.20, 1.10–1.65; MS (ESI+) m/z 248.2 (M+H⁺).

(5R)-1-Azabicyclo[3.2.1]octan-3-one hydrochloride

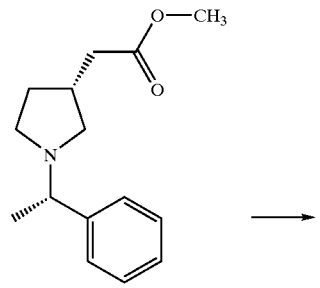

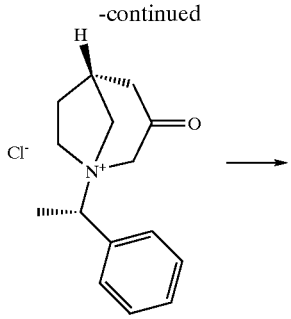

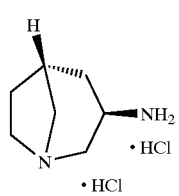

(3R, 5R)-[3.2.1]-Amine

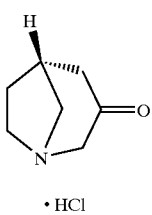
· HCl

A solution of (3R)-methyl 1-[(S)-1-phenylethyl] pyrrolidine-3-acetate (25.72 g, 104.0 mmol) in THF (265 mL) is cooled under $N_2$ in a $CO_2$/acetone bath. Next, $ICH_2Cl$ (22.7 mL, 312.0 mmol) is added, and the mixture stirred for 30 min. A solution of 2.0 M lithium diisopropylamide (heptane/THF/ethylbenzene, 156 mL, 312 mmol) is added slowly over 30 min. The internal temperature reached a maximum of −40° C. during this addition. After 1 h, sat. $NH_4Cl$ (100 mL) is added and the mixture is allowed to warm to rt. The organic layer is separated, dried ($MgSO_4$), filtered and concentrated. The resulting foam is chromatographed (300 g $SiO_2$, $CHCl_3$—MeOH—$NH_4OH$ (89:10:1) followed by $CHCl_3$—MeOH (3:1). The product fractions are pooled and concentrated to afford (5R)-3-oxo-1-[(1S)-1-phenylethyl]-1-azoniabicyclo[3.2.1]octane chloride (10.12 g) as a foam (MS (ESI+) m/z 230.1 (M+H$^+$). This foam (10.1 g, 38 mmol) is taken up in MeOH (500 mL), 10% Pd(C) (3.0 g) added and the mixture is hydrogenated (45 psi) overnight. The mixture is filtered and re-subjected to the reduction conditions (9.1 g, 10% Pd/C, 50 psi). After 5 h, TLC indicates the consumption of the (5R)-3-oxo-1-[(1S)-1-phenylethyl]-1-azoniabicyclo[3.2.1]octane chloride. The mixture is filtered, concentrated and triturated (minimal iPrOH) to give 3.73 g in two crops, as a solid: $[\alpha]^{25}_D$=33 (c 0.97, DMSO); HRMS (FAB) calcd for $C_7H_{11}NO$ (M+H$^+$) 126.0919, found 126.0937.

(3R,5R)-1-azabicyclo[3.2.1]octan-3-amine dihydrochloride

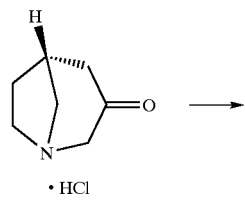

To a flask containing (5R)-1-azabicyclo[3.2.1]octan-3-one hydrochloride (3.64 g, 22.6 mmol), hydroxylamine hydrochloride (2.04 g, 29.4 mmol), and ethanol (130 mL) is added sodium acetate trihydrate (9.23 g, 67.8 mmol). The mixture stirred for 3 h and is filtered and concentrated. The resulting white solid is taken up in n-propanol (100 mL) and sodium (~13.6 g, 618 mmol) is added in 20–25 portions. The reaction spontaneously begins to reflux, and the reaction is heated in an oil bath (100° C.). The addition is complete in ~20 min and the mixture solidifies after ~40 min. The oil bath is removed and n-propanol (2×25 mL) is added dissolving the remaining sodium metal. The mixture is carefully quenched through the dropwise addition of $H_2O$ (100 mL). Saturated aq. NaCl (20 mL) is added, and the layers are separated. The organic layer is dried ($MgSO_4$), filtered, treated with freshly prepared MeOH/HCl, and concentrated. The resulting solid is triturated with 30 mL EtOH, filtered and dried in vaccuo to afford 3.51 g as a white solid: $[\alpha]^{25}_D$=−3 (c 0.94, DMSO); $^1$H NMR (400 MHz, DMSO-$d_6$) δ 3.60–3.80, 2.95–3.10, 2.65–2.75, 1.90–2.15, 1.70–1.90; HRMS (FAB) calcd for $C_7H_{14}N_2$ (M+H$^+$) 127.1235, found 127.1235.

Preparation of the 3.2.2 Amines

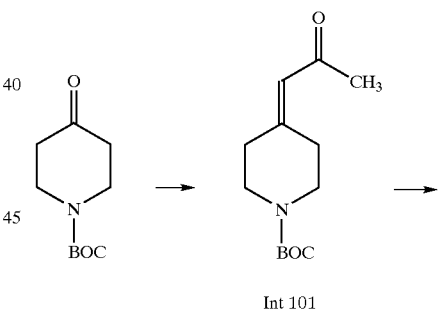

Int 101

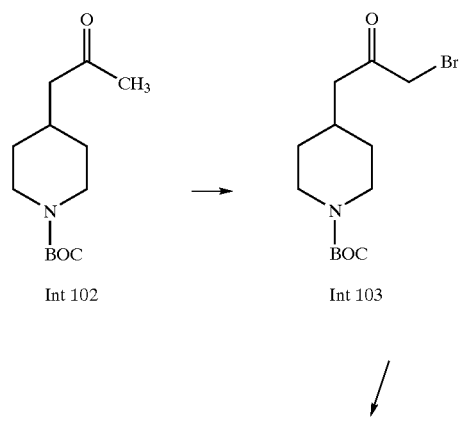

Int 102          Int 103

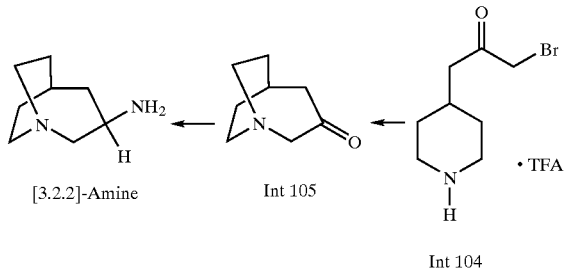

Preparation of tert-butyl 4-(2-oxopropylidene)piperidine-1-carboxylate (Int 101):

Sodium hydride (60% oil dispersion, 2.01 g, 50.2 mmol) was washed with pentane (3×) and suspended in dry THF (40 mL). The solution was cooled to 0° C. before diethyl (2-oxopropyl)phosphonate (9.75 g, 50.2 mmol) was added dropwise. After complete addition, the solution was warmed to rt and stirred for 30 min. tert-Butyl 4-oxo-1-piperidinecarboxylate (5.0 g, 25.1 mmol) was added in portions over 10 min, followed by stirring at rt for 2 h. A saturated aqueous solution of ammonium chloride was added, followed by dilution with ether. The organic layer was extracted with water. The organic layer is dried over anhydrous MgSO$_4$, filtered and concentrated to a yellow oil. The crude product was purified by flash chromatography on silica gel. Elution with hexanes-ether (60:40) gave 4.5 g (75%) of Int 101 as a white solid: $^1$NMR (CDCl$_3$) δ 6.2, 3.5, 3.4, 2.9, 2.3, 2.2, 1.5.

Preparation of tert-butyl 4-(2-oxopropyl)piperidine-1-carboxylate (Int 102):

A mixture of Int 101 (4.5 g, 19 mmol) and 10% palladium on activated carbon (450 mg) in EtOH (150 mL) was placed in a Parr bottle and hydrogenated for 5 h at 50 psi. The mixture was filtered through Celite, and the filtrate was concentrated in vacuo to afford 4.3 g (94%) of Int 102 as a clear oil: $^1$H NMR (CDCl$_3$) δ 4.1, 2.8, 2.4, 2.2, 2.0, 1.7, 1.5, 1.1.

Preparation of tert-butyl 4-(3-bromo-2-oxopropyl)piperidine-1-carboxylate (Int 103):

To a stirred solution lithium hexamethyldisilylamide in THF (20.0 mL, 1.0 M) in a −78° C. bath was added chlorotrimethylsilane (11.0 mL, 86.4 mmol) dropwise. The mixture was stirred at −78° C. for 20 min, followed by addition of 102 (3.21 g, 13.3 mmol) in a solution of THF (50 mL) dropwise. After complete addition, the mixture was stirred at −78° C. for 30 min. The mixture was warmed to 0° C. in an ice-water bath and phenyltrimethylammonium tribromide (5.25 g, 14.0 mmol) was added. The mixture was stirred in an ice-bath for 30 min, followed by the addition of water and ether. The aqueous layer was washed with ether, and the combined organic layers were washed with saturated aqueous sodium thiosulfate solution. The organic layer was dried over anhydrous MgSO$_4$, filtered and concentrated in vacuo to afford a yellow oil. The crude product was purified by flash chromatography on silica gel. Elution with hexanes-ether (60:40) gave 2.2 g (52%) of Int 103 as a lt. yellow oil: $^1$H NMR (CDCl$_3$) δ 4.2–4.1, 3.9, 2.8, 2.7, 2.6, 2.1–2.0, 1.7, 1.5, 1.2–1.1.2.

Preparation of 1-bromo-3-piperidin-4-ylacetone trifluoroacetate (Int 104):

To a stirred solution of 103 (2.2 g, 6.9 mmol) in CH$_2$Cl$_2$ (30 mL) in an ice-water bath was added trifluoroacetic acid (10 mL, 130 mmol). The mixture was stirred at 0° C. for 30 min. The volatiles were removed in vacuo to afford 2.0 g (87%) of Int 104 as a yellow residue: MS (ESI) for C$_8$H$_{15}$BrNO [M+H] m/e 220.

Preparation of 1-azabicyclo[3.2.2]nonan-3-one (Int 105):

To a stirred solution of DIEA (13 mL) in acetonitrile (680 mL) at reflux temperature was added a solution of Int 104(2.0 g, 6.0 mmol) in acetonitrile (125 mL) over a 4 h period via syringe pump. The mixture was kept at reflux temperature overnight. The mixture was concentrated in vacuo and the remaining residue was partitioned between a saturated aqueous K$_2$CO$_3$ solution and CHCl$_3$—MeOH (90:10). The aqueous layer was extracted with CHCl$_3$—MeOH (90:10), and the combined organic layers were dried over MgSO$_4$, filtered and concentrated in vacuo to a brown oil. The crude product was purified by flash chromatography on silica gel. Elution with CHCl$_3$—MeOH—NH$_4$OH (95:4.5:0.5) gave 600 mg (72%) of Int 105 as a clear solid: $^1$H NMR (CDCl$_3$) δ 3.7, 3.3–3.2, 3.1–3.0, 2.7, 2.3, 2.0–1.8.

Preparation of 1-azabicyclo[3.2.2]nonan-3-amine bis(4-methylbenzenesulfonate)([3.2.2]-Amine):

To a stirred mixture of Int 105 (330 mg, 2.4 mmol) and sodium acetate.trihydrate (670 mg, 4.8 mmol) in EtOH (6.0 mL) was added hydroxylamine.hydrochloride (200 mg, 2.8 mmol). The mixture was stirred at rt for 10 h. The mixture was filtered and the filtrate was concentrated in vacuo to a yellow solid. To a solution of the solid (350 mg, 2.3 mmol) in n-propanol (30 mL) at reflux temperature was added sodium metal (2.0 g, 87 mmol) in small portions over 30 min. Heating at reflux was continued for 2 h. The solution is cooled to rt and brine is added. The mixture is extracted with n-propanol, and the combined organic layers are concentrated in vacuo. The residue was taken up in CHCl$_3$ and the remaining solids were filtered. The filtrate was dried over anhydrous MgSO$_4$, filtered and concentrated in vacuo to a clear solid. To a stirred solution of the solid (320 mg, 2.3 mmol) in EtOH (4 mL) was added p-toluenesulfonic acid monohydrate (875 mg, 4.6 mmol). The solution was warmed in a water bath to 45° C. for 30 min, followed by concentration of the solvent to afford 710 mg (62%) of [3.2.2]-Amine as a white solid: $^1$H NMR (CD$_3$OD) δ 7.7, 7.3, 4.1–3.9, 3.6–3.4, 2.6–2.5, 2.4, 2.2–2.1, 2.1–2.0, 1.9.

Resolution of Stereoisomers:

The amine can be coupled to form the appropriate amides or thioamides as a racemic mixture. The racemic mixture can then be resolved by chromatography using chiral columns or chiral HPLC, techniques widely known in the art, to provide the requisite resolved enantiomers 3(R) and 3(S) of said amides or thioamides.

Coupling the Amine with the Requisite Acid:

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. Moreover, the examples provided are carried out using one amine. However, any amine could be used making non-critical changes but starting with the amine not identified. The invention includes the following examples in pure stereoisomeric form or as racemic mixtures.

EXAMPLE 1

Endo-N-(1-azabicyclo[2.2.1]hept-3-yl)-5-bromo-thiophene-2-carboxamide.fumarate

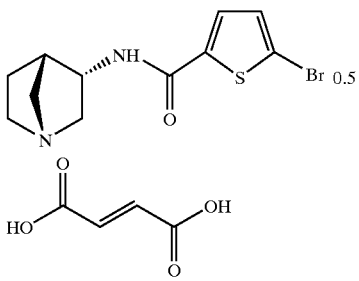

Step 1a

To a stirred suspension of 5-bromo-thiophene-2-carboxylic acid (136 mg, 0.66 mmol) in dry $CH_2Cl_2$ (3.0 mL) is added TEA (92 μL, 0.66 mmol), followed by DPPA (118 μL, 0.55 mmol). In a separate flask, to a stirred solution of Amine 2 (200 mg, 0.44 mmol) in water (0.5 mL) and DMF (3.0 mL) is added TEA (245 μL, 1.76 mmol). After 10 min, the amine solution is rapidly added to the carboxylic acid solution, and the combined mixture is stirred for 24 h at rt. The reaction mixture is partitioned between saturated aqueous $K_2CO_3$ solution and $CH_2Cl_2$. The aqueous layer is extracted with $CH_2Cl_2$, and the combined organic layers are washed with brine, dried over $MgSO_4$, filtered and concentrated in vacuo to a clear residue. The crude product is purified by flash chromatography on silica gel. Elution with $CHCl_3$—MeOH—$NH_4OH$ (90:9:1) gave 59 mg (45%) of a white solid: MS (ESI) m/e 302 [M+H].

Step 1b

To a stirred solution of the product from Step 26a (70 mg, 0.23 mmol) in acetone (5 mL) is added a hot solution of fumaric acid (27 mg, 0.23 mmol) in IPA (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 60 mg (62%) of Example 1 as white solid: $^1H$ NMR ($CD_3OD$) δ 7.6, 7.2, 6.7, 4.5, 3.6, 3.4–3.1, 2.9, 2.1–1.9.

EXAMPLE 2

N-(exo-(4S)-1-azabicyclo[2.2.1]hept-3-yl)-5-bromo-thiophene-2-carboxamide.fumarate

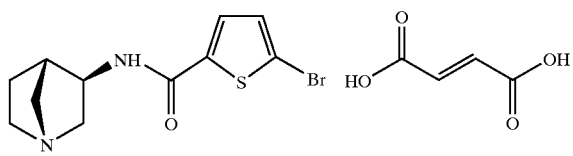

Step 2a.

To a stirred suspension of 5-bromo-thiophene-2-carboxylic acid (136 mg, 0.66 mmol) in dry $CH_2Cl_2$ (3.0 mL) is added TEA (92 μL, 0.66 mmol), followed by DPPA (118 μL, 0.55 mmol). In a separate flask, to a stirred solution of exo-(4S)-[2.2.1]-3-Amine (200 mg, 0.44 mmol) in water (0.5 mL) and DMF (3.0 mL) is added TEA (245 μL, 1.76 mmol). After 10 min, the amine solution is rapidly added to the carboxylic acid solution, and the combined mixture is stirred for 24 h at rt. The reaction mixture is partitioned between saturated aqueous $K_2CO_3$ solution and $CH_2Cl_2$. The aqueous layer is extracted with $CH_2Cl_2$, and the combined organic layers are washed with brine, dried over $MgSO_4$, filtered and concentrated in vacuo to a clear residue. The crude product is purified by flash chromatography on silica gel. Elution with $CHCl_3$—MeOH—$NH_4OH$ (90:9:1) gave 59 mg (45%) of a white solid: MS (ESI) m/e 302 [M+H].

To a stirred solution of the product of Step 2a (59 mg, 0.20 mmol) in acetone (5 mL) is added a hot solution of fumaric acid (23 mg, 0.20 mmol) in IPA (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 50 mg (61%) of Example 2 as white solid: $^1H$ NMR ($CD_3OD$) δ 7.6, 7.2, 6.7, 4.2, 3.7, 3.5–3.4, 3.2, 3.0, 2.2, 1.8.

EXAMPLE 3

N-[exo-4(S)-1-azabicyclo[2.2.1]hept-3-yl]-5-phenylthiophene-2-carboxamide.fumarate

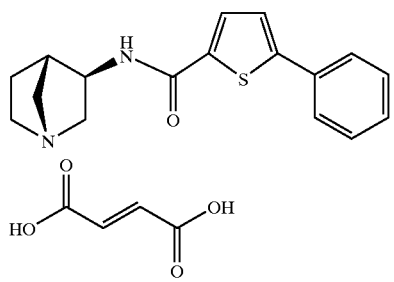

Step 3a

5-Bromothiophene-2-carboxaldehyde (1.0 g, 5.2 mmol) is added to a solution of tetrakis(triphenylphosphine)palladium (0) (180 mg, 0.16 mmol) in degassed THF (10 mL). The resulting solution is stirred for 5 min. A solution of phenylboronic acid (760 mg, 6.2 mmol) in THF (10 mL) is added followed by aqueous $Na_2CO_3$ (2M, 5.2 mL). The mixture is heated at reflux for 24 h. The reaction mixture is allowed to cool, poured into ether, and washed twice with water. The ether layer is dried over $Na_2SO_4$ and concentrated in vacuo. The crude product is purified by flash column chromatography (1:1 hexanes:$CH_2Cl_2$) to yield 5-phenylthiophene-2-carboxaldehyde (900 mg, 91%). $^1H$ NMR (300 MHz, $CDCl_3$) δ 7.38–7.45, 7.65–7.68, 7.73, 9.88.

Step 3b

The product of Step 3a (750 mg, 4 mmol) is dissolved in a mixture of THF, t-BuOH, and water (2:1:1, 60 mL). $KH_2PO_4$ (1.36 g, 10 mmol) is added followed by $NaClO_2$ (900 mg, 10 mmol). The mixture is stirred at rt for 5 days. Aqueous NaOH (2M, 10 mL) is added, and a majority of the organic solvents are removed in vacuo yielding an aqueous suspension. This suspension is diluted with water and washed three times with $CH_2Cl_2$. The aqueous layer is acidified to pH<6 with 25% $H_2SO4$ and the product is extracted three times with $CH_2Cl_2$. The combined organic washes are dried over $Na_2SO_4$, filtered and concentrated in vacuo to yield 5-phenylthiophene-2-carboxylic acid (417 mg, 51%). MS for $C_{11}H_8O_2S$ (ESI) (M–H)⁻ m/z 203.

Step 3c

To a stirred solution of 5-phenylthiophene-2-carboxylic acid (100 mg, 0.50 mmol) in dry DMF (10 mL) is added DIEA (265 μL, 1.5 mmol), followed by exo-(4S)-[2.2.1]-3-Amine (230 mg, 0.50 mmol). The solution is cooled with an ice bath before 190 mg (0.50 mmol) of HATU is added. The solution is allowed to warm to rt and stir for 16 h. The solvent is removed in vacuo, and the remaining residue is partitioned between saturated aqueous $K_2CO_3$ solution and 9:1 $CHCl_3$—MeOH. The aqueous layer is extracted with 9:1 $CHCl_3$—MeOH, and the combined organic layers are washed with brine, dried over $MgSO_4$, filtered and concentrated in vacuo to afford the free base of Example 3 as a light yellow solid (150 mg, 100%): MS for $C_{17}H_{18}ON_2S$ (ESI) m/e 299 $(M+H)^+$.

Step 3d

To a stirred solution of the product from Step 3c (150 mg, 0.50 mmol) in MeOH (2 mL) is added a hot solution of fumaric acid (58 mg, 0.50 mmol) in IPA (2 mL). The mixture is stirred for 30 min in a 50° C. water bath. The solvents are removed in vacuo and the remaining residue is dissolved in ether (5 mL). The mixture is stirred overnight at rt. The solid precipitate is collected by filtration and washed with acetone. The solid is dried in vacuo overnight to give 180 mg (87%) of Example 3 as a white solid: $^1$H NMR ($CD_3OD$) δ 7.8, 7.7, 7.5–7.4, 6.7, 4.2, 3.7–3.6, 3.5–3.3, 3.2, 3.0, 2.2–2.1, 1.8.

EXAMPLE 4

5-(2-Aminophenyl)-N-[exo-4(S)-1-azabicyclo[2.2.1]hept-3-yl]-thiophene-2-carboxamide

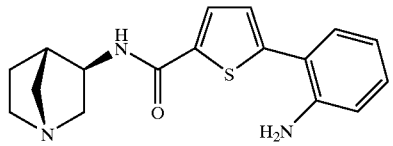

5-(2-Nitrophenyl)-N-[exo-4(S)-1-azabicyclo[2.2.1]hept-3-yl]-thiophene-2-carboxamide can be reduced to the amine applying $H_2$ under pressure in the presence of Pd/C using EtOH and $CH_2Cl_2$ as the solvent to give Example 4.

EXAMPLE 5

N-[exo-4(S)-1-azabicyclo[2.2.1]hept-3-yl]-5-pyridin-3-yl-thiophene-2-carboxamide

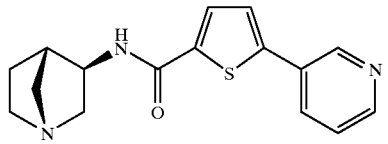

Step 5a

In a flask are placed 3-pyridinediethylborane (0.81 g, 5.5 mmol), 2-bromothiophene-5-carboxaldehyde (0.59 mL, 5.0 mmol), and $Pd(PPh_3)_4$ (0.17 g, 0.15 mmol). The flask is vacuum purged and nitrogen filled three times followed by addition of a 4:1 mixture of toluene-EtOH (8.3 mL) by syringe. After careful vacuum purge/nitrogen fill (3×), a solution of $Na_2CO_3$ (2M, 5 mL, 10.0 mmol) is added by syringe, and the flask is vacuum purged and nitrogen filled (3×). The reaction mixture is heated to 90° C. and stirred for 22 h. The reaction mixture is cooled to rt and diluted with $H_2O$. The aqueous solution is extracted with ether (3×). The combined ether layers are then washed with water (3×) and brine (2×). The organic layer is dried over $MgSO_4$, diluted with EtOAc for solubility, then filtered and concentrated. The crude product is then chromatographed over silica gel (10/30/50% EtOAc-heptane gradient) to provide 5-(3-pyridinyl)-2-thiophenecarboxaldehyde as a yellow solid (0.34 g, 35%). $^1$NMR (400 MHz, $CDCl_3$): 9.97, 9.05, 8.68, 8.13, 7.83, 7.59–7.54.

Example 5 can be made from the product of Step 5a by using the procedure discussed in Steps 3b and 3c, making non-critical variations.

EXAMPLE 6

N-[exo-4(S)-1-azabicyclo[2.2.1]hept-3-yl]-5'-methyl-2,2'-bithiophene-5-carboxamide

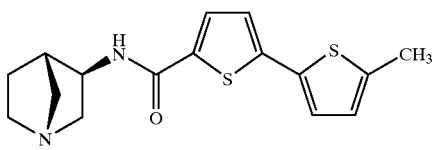

Step 6a

In a flask are placed 2-bromothiophene-5-carboxylic acid (1.20 g, 5.81 mmol), 5-methylthiophene-2-boronic acid (0.99 g, 6.97 mmol), and $Pd(PPh_3)_4$ (0.20 g, 0.17 mmol). The flask is then vacuum purged and nitrogen filled (3×). THF (12 mL) is then added by syringe followed by vacuum purge and nitrogen fill (3×). A solution of $Na_2CO_3$ (2M, 5.8 mL, 11.6 mmol) is added followed by vacuum purge and nitrogen fill (3×). The reaction mixture is heated to reflux for 19 h then cooled to rt and diluted with water. The aqueous solution is extracted with ether (3×). The aqueous layer is then acidified and extracted with EtOAc (3×). The combined organic layers are dried over $MgSO_4$, filtered, and concentrated to provide an inseparable 3:1 mixture of 2-bromothiophene-5-carboxylic acid and bithiophene product. To separate the compounds the methyl esters are formed: In a flask are placed the aforementioned mixture, MeOH (50 mL) and conc $H_2SO_4$ (5 drops) and heated to reflux for 24 h. The solution is concentrated and chromatographed over silica gel (2% acetone-heptane) to provide methyl 5'-methyl-2,2'-bithiophene-5-carboxylate as a solid (0.37 g, 26% 2 steps). $^1$H NMR (400 MHz, $CDCl_3$) δ 7.69, 7.10, 7.07, 6.73, 3.91, 2.52.

Step 6b

The product of Step 6a (0.37 g, 1.54 mmol), dioxane (5 mL) and LiOH (1N, 3.1 mL, 3.1 mmol) are placed in a flask. Additional dioxane (5 mL) is then added for solubility and stirred for 24 h at rt. 1N HCl is added slowly until pH<6, whereupon a precipitate forms. The precipitate is then collected by filtration, rinsed with water, and dried in a 70° C. vacuum oven to provide 5'-methyl-2,2'-bithiophene-5-carboxylic acid as a yellow solid (0.30 g, 86%). MS for $C_{10}H_8O_2S_2$ (ESI) $(M-H)^-$ m/z 223.

Example 6 can be made using the product of Step 6b as the starting material and using the procedure discussed in either Step 1a or Step 2a, making non-critical variations.

EXAMPLE 7

N-[exo-4(S)-1-azabicyclo[2.2.1]hept-3-yl]-5'-chloro-2,2'-bithiophene-5-carboxamide

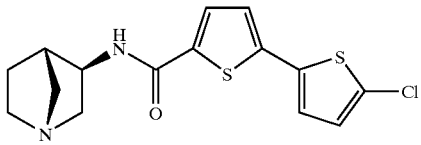

Step 7a

In a flask are placed 2-bromo-5-chlorothiophene (0.55 mL, 5.0 mmol) and Pd(PPh$_3$)$_4$ (0.17 g, 0.15 mmol), and the flask is vacuum purged and nitrogen filled (3×). THF (10 mL) is added by syringe and stirred 10 min. In a separate flask is placed 5-formyl-2-thiopheneboronic acid (0.94 g, 6.0 mmol) and EtOH (2 mL) and stirred until dissolved. This mixture is added by syringe to the first flask followed by vacuum purge and nitrogen fill (3×). A solution of Na$_2$CO$_3$ (2M, 5.0 mL, 10.0 mmol) is added by syringe followed by vacuum purge and nitrogen fill (3×). The reaction mixture is heated at 85° C. for 20 h. The reaction is cooled to rt and diluted with water. The aqueous solution is extracted with ether (3×). The combined ether layers are washed with water (3×) then brine (2×). The ether is dried over MgSO$_4$, filtered, and concentrated. The crude product is purified over silica gel (5% EtOAc-heptane) to provide 5'-chloro-2,2'-bithiophene-5-carboxaldehyde as an orange solid (0.27 g, 24%).

$^1$H NMR (400 MHz, CDCl$_3$) δ 9.89, 7.69, 7.20, 7.16, 6.93.

Example 7 can be made from the product of Step 7a as the starting material by using the procedures discussed in Steps 3b and 3c, making non-critical variations.

EXAMPLE 8

N-[exo-4(S)-1-azabicyclo[2.2.1]hept-3-yl]-5-nitro-thiophene-2-carboxamide

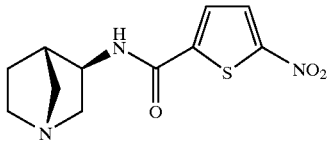

Example 8 can be made from 2-nitrothiophene-5-carboxaldehyde by using the procedure discussed in Steps 3b and 3c, making non-critical variations.

EXAMPLE 9

5-(Aminomethyl)-N-[exo-4(S)-1-azabicyclo[2.2.1]hept-3-yl]-thiophene-2-carboxamide

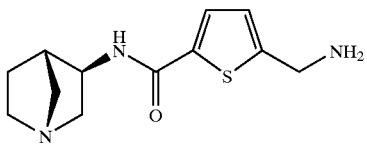

Step 9a

A 500 mL receiving flask is placed in an ice bath, and to the flask is added thiophene-2-methylamine (5.0 mL, 48.7 mmol), CH$_2$Cl$_2$ (250 mL) then di-tert-butyl dicarbonate (12.7 g, 73.0 mmol) in 2–3 g portions over 5 min. The reaction mixture is stirred for 3 h then washed with 1N HCl (3×), 1N NaOH (3×) and brine (2×). The organic layer is dried over MgSO$_4$, filtered and concentrated to a yellow oil. The oil is chromatographed over silica gel (2.5–5% EtOAc-heptane gradient) to provide 8.70 g (84%) of tert-butyl 2-thienylmethylcarbamate as a clear oil. MS for C$_{10}$H$_{15}$NO$_2$S (ESI) (M+H)$^+$ m/z 214.

Step 9b

In a flask is placed the product of Step 9a (3.50 g, 16.4 mmol) and dry THF (80 mL) then cooled in an acetone/solid CO$_2$ bath. Lithium diisopropylamide (18.0 mL, 36.1 mmol, 2.0M solution in heptane/THF/ethylbenzene) is added in a slow stream by syringe. The resulting orange solution is stirred for 10 min and then quenched with excess dry ice. The solution is warmed over 1 h and the THF removed in vacuo. The crude product is diluted with CH$_2$Cl$_2$ and washed with 1N HCl (3×). The CH$_2$Cl$_2$ is removed in vacuo and replaced with EtOAc due to insolubility. The organic solution is dried over MgSO$_4$, filtered, and concentrated to provide a dark orange oil, which is chromatographed over silica gel (25–90% EtOAc-heptane gradient) to provide 0.873 g (21%) of 5-([(tert-butoxycarbonyl)amino]methyl)-2-thiophenecarboxylic acid as an off-white foam. $^1$H NMR (400 MHz, CDCl$_3$) δ 12.96, 7.60, 7.56, 6.97, 4.28, 1.40.

Example 9 can be made by using the product of Step 9b as a starting material and using the procedure discussed in either Step 1a or Step 2a, making non-critical variations.

EXAMPLE 10

N-[exo-4(S)-1-azabicyclo[2.2.1]hept-3-yl]-5-cyano-thiophene-2-carboxamide

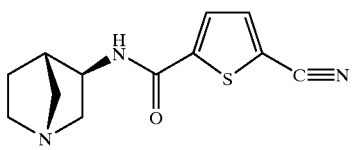

Step 10a

In a 500 mL receiving flask are placed thiophene-2-carbonitrile (5.0 mL, 53.8 mmol) and THF (270 mL) and cooled in an acetone/solid CO$_2$ bath. Lithium diisopropylamide (40.3 mL, 80.7 mmol, 2.0M solution in heptane/THF/ethylbenzene) is added in a slow stream via syringe. The solution is stirred for 10 min then quenched with an excess of dry ice. The reaction mixture is warmed in a water bath and the THF removed in vacuo. The slurry is taken up in 1N NaOH and extracted with ether (3×). The aqueous layer is then acidified to pH<6 with conc. HCl, whereupon a brown precipitate forms. This precipitate is filtered off and to the resulting eluent is added 1N HCl which results in precipitation of the product. The product is collected by filtration then triturated with CH$_2$Cl$_2$. Purification over silica gel (1:2.5:100 formic acid:MeOH:CH$_2$Cl$_2$) provides 5-cyano-thiophene-2-carboxylic acid as a solid (1.79 g, 22%). $^1$H NMR (400 MHz, CDCl$_3$) δ 14.10, 8.00, 7.80.

Example 10 can be made by using the product of Step 10a as a starting material and using the procedure discussed in either Step 1a or Step 2a, making non-critical variations.

EXAMPLE 11

N-[exo-4(S)-1-azabicyclo[2.2.1]hept-3-yl]-5-(pyridin-2-yl)-thiophene-2-carboxamide.fumarate

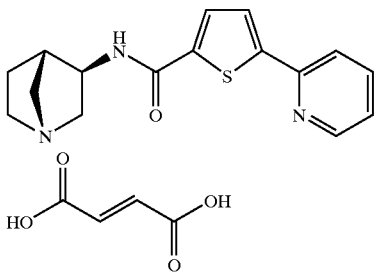

Following the procedure of Step 3c from Example 3, the free base of Example 11 is obtained in quantitative yield as a light yellow solid: MS for $C_{16}H_{17}ON_3S$ (ESI) m/e 300 (M+H)$^+$.

Following the procedure of Step 3d from Example 3, Example 11 is obtained in 84% yield as a white solid: $^1$H NMR (CD$_3$OD) δ 8.5, 7.9, 7.8, 7.7, 7.4, 6.7, 4.2, 3.7, 3.4–3.3, 3.2, 3.0, 2.2–2.1, 1.8.

EXAMPLE 12

N-[exo-4(S)-1-azabicyclo[2.2.1]hept-3-yl]-5-(2-methylthiazol-4-yl)-thiophene-2-carboxamide

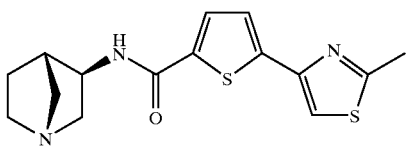

Step 12a

Aqueous LiOH (1N, 1.5 mL) is added to a solution of methyl 5-(2-methylthiazol-4-yl)-thiophene-2-carboxylate (81 mg, 0.34 mmol) in dioxane (1 mL). The reaction is stirred at rt for 2 hr. Aqueous HCl (1N, 4 mL) is added and the resultant precipitate is collected by filtration, washed with water, and dried to give 5-(2-methylthiazol-4-yl)-thiophene-2-carboxylic acid (53 mg, 69%). $^1$H NMR (300 MHz, DMSO-d$_6$) δ 8.03, 7.69, 7.59, 2.70.

Example 12 can be made by using the product of Step 12a as a starting material and using the procedure outlined for Example 1 or Example 2, making non-critical variations.

EXAMPLE 13

N-[exo-4(S)-1-azabicyclo[2.2.1]hept-3-yl]-5-[2-(3-chlorophenyl)-vinyl]-thiophene-2-carboxamide

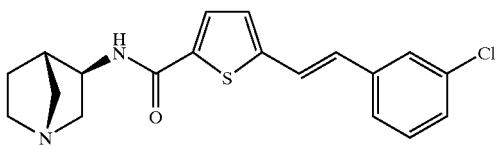

Example 13 can be prepared from methyl 5-[2-(3-chlorophenyl) vinyl]-thiophene-2-carboxylate according to the procedure used to make the compound of Example 12, making non-critical variations.

EXAMPLE 14

N-[exo-4(S)-1-azabicyclo[2.2.1]hept-3-yl]-5-(4-chlorophenylsulfanyl)-thiophene-2-carboxamide

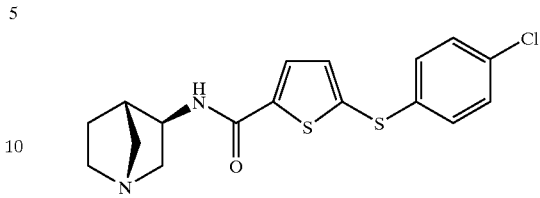

Step 14a

Sodium hydride (60%, 1.2 g, 30 mmol) is added to a solution of 4-chlorothiophenol (4.3 g, 30 mmol) in THF (30 mL). The resulting solution is stirred for 10 min then the solvent is removed in vacuo. Acetone (60 mL) is added followed by 5-bromothiophene-2-carboxaldehyde (30 mL, 25 mmol). The mixture is stirred at rt for 2 hr. The solvent is removed in vacuo and the resulting slurry diluted with CH$_2$Cl$_2$. This solution is washed three times with 1N NaOH then dried over MgSO$_4$, filtered and concentrated in vacuo. The crude product is purified by flash column chromatography (gradient of 1 to 5% EtOAc in heptane) to give 5-(4-chlorophenylsulfanyl)-thiophene-2-carboxaldehyde (6.2 g, 98%). $^1$H NMR (300 MHz, CDCl$_3$) δ 7.13, 7.31–7.39, 7.63, 9.78.

Step 14b

The product of Step 14a (6.1 g, 24 mmol) is dissolved in a mixture of THF, t-BuOH, and water (3:3:1, 255 mL). 2-Methyl-2-butene (20.3 mL, 192 mmol) is added followed by KH$_2$PO$_4$ (9.8 g, 72 mmol) and then NaClO$_2$ (80%, 8.17 g, 72.3 mmol). The mixture is stirred at rt for 2 hr. Aqueous KHSO$_4$ (0.5M, 200 mL) is added and the organic solvents are removed in vacuo to produce an aqueous suspension of the product. The precipitate is collected by filtration, dissolved in 1N NaOH and washed two times with ether. The aqueous solution is then acidified to pH<6 with concentrated HCl and a precipitate formed. The precipitate is collected by filtration and washed with 0.5M KHSO$_4$ then water. The solid is dried in vacuo to give 5-(4-chlorophenylsulfanyl)-thiophene-2-carboxylic acid (5.7 g, 87%). MS for $C_{11}H_7ClO_2S_2$ (ESI) (M−H)$^-$ m/z 269.

Step 14c

Example 14 can be obtained using the coupling procedures discussed herein. The salt can be obtained as discussed herein.

EXAMPLE 15

N-[exo-4(S)-1-azabicyclo[2.2.1]hept-3-yl]-5-phenoxy-thiophene-2-carboxamide

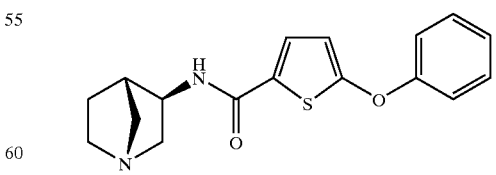

Step 15a

Phenol (3.3 g, 35 mmol) is added in portions to a suspension of 60% NaH (1.3 g, 35 mmol) in DMSO (100 mL). The resulting mixture is stirred for 30 min then 5-nitrothiophene-2-carboxaldehyde (5 g, 32 mmol) is added.

After 1 hr the reaction mixture is poured into water (1L) and washed with ether (4×500 mL). The combined organic layers are dried over Na$_2$SO$_4$, filtered and evaporated to dryness. The resulting material is dissolved in MeOH and passed through a column (2.5 cm×20 cm) of Amberjet 4400 (OH$^-$ form). The eluent is dried in vacuo then evaporated twice from CH$_3$CN. The crude product is purified by column chromatography in EtOAc-hexanes (1:1) to yield 5-phenoxy-thiophene-2-carboxaldehyde (304 mg, 5%). $^1$H NMR (300 MHz, CDCl$_3$) δ 6.52, 7.20, 7.27, 7.45, 7.55, 9.75.

Step 15b

5-Phenoxy-thiophene-2-carboxaldehyde (325 mg, 1.6 mmol) is dissolved in a mixture of THF (10 mL), t-BuOH (5 mL) and water (5 mL). NaH$_2$PO$_4$ (650 mg, 4.8 mmol) is added followed by NaClO$_2$ (432 mg, 4.8 mmol). The resulting mixture is stirred for 24 hr at rt. Aqueous NaOH (2M, 5 mL) is added, and the organic solvents are removed in vacuo. The resulting aqueous suspension is poured into water (50 mL) and washed with ether (3×50 mL). The aqueous layer is acidified to pH<2 with 25% H$_2$SO$_4$ then washed with CH$_2$Cl$_2$ (3×50 mL). The combined organic washes are dried over Na$_2$SO$_4$, filtered and concentrated in vacuo. The crude product is dissolved in hot aqueous acetone and filtered. The solvents are gradually removed until a precipitate forms. The solid is collected by filtration and dried in vacuo to yield 5-phenoxy-thiophene-2-carboxylic acid (192 mg, 55%). MS for C$_{11}$H$_7$O$_3$S (ESI) (M+H)$^+$ m/z 219.

Example 15 can be made according to the procedures discussed herein, starting with 5-phenoxy-thiophene-2-carboxylic acid and making non-critical variations.

EXAMPLE 16

N-[exo-4(S)-1-azabicyclo[2.2.1]hept-3-yl]-5-(2-hydroxyphenyl)-thiophene-2-carboxamide

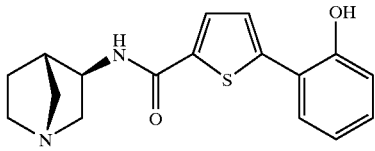

Step 16a

Tetrakis(triphenylphosphine)palladium(0) (133 mg, 0.12 mmol) is added to a solution of 5-bromothiophene-2-carboxylic acid (850 mg, 4.6 mmol) in degassed THF (10 mL). The resulting solution is stirred for 5 min and then 2-(4,4,5,5-tetramethyl)-1,3,2-dioxaborolan-2-yl) phenol (1 g, 4.6 mmol) is added followed by aqueous Na$_2$CO$_3$ (2M, 6.9 mL). The mixture is heated at reflux overnight. The reaction mixture is allowed to cool, poured into water (50 mL), and washed with ether (3×50 mL). The aqueous layer is acidified with concentrated HCl to pH<2. The resulting precipitate is collected by filtration, washed with water and dried in vacuo to yield 5-(2-hydroxyphenyl)-thiophene-2-carboxylic acid (761 mg, 83%). MS for C$_{11}$H$_7$O$_3$S (ESI) (M−H)$^+$ m/z 219.

Example 16 can be obtained using the coupling methods discussed herein.

EXAMPLE 17

N-[exo-4(S)-1-azabicyclo[2.2.1]hept-3-yl]-5-(3-hydroxyphenyl)-thiophene-2-carboxamide

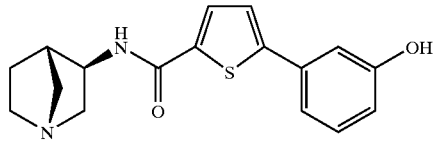

Example 17 can be made from the 3-hydroxyphenylboronic acid according to the procedure of Example 16, making non-critical variations.

EXAMPLE 18

N-[exo-4(S)-1-azabicyclo[2.2.1]hept-3-yl]-5-(3-fluoro-4-hydroxyphenyl)-thiophene-2-carboxamide

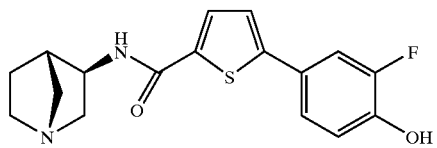

Step 18a

Example 18 can be obtained by starting from N-[exo-4(S)-1-azabicyclo[2.2.1]hept-3-yl]-5-(3-benzyloxyphenyl)-thiophene-2-carboxamide, which can be obtained following the procedures outlined for Example 3 using 3-benzyloxyphenylboronic acid as the acid. The intermediate can then be dissolved in MeOH and poured through a plug of Amberjet 4400 (OH$^-$ form). The solvent can be removed in vacuo, and the product can be redissolved in EtOH. This solution can be added to a suspension of 10% Pd/C in EtOH. Cyclohexadiene (360 mL, 3.8 mmol) would be added, and the reaction heated at 60° C. for 6 hr. The reaction mixture can then be diluted with MeOH and filtered through celite. The solvents can be removed in vacuo to give the free base. A salt can be formed as discussed herein.

EXAMPLE 19

N-[exo-4(S)-1-azabicyclo[2.2.1]hept-3-yl]-2-(phenylsulfanyl)-1,3-thiazole-5-carboxamide

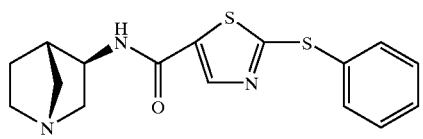

Step 19a

A suspension of ethyl 2-bromo-1,3-thiazole-5-carboxylate (1.5 g, 6.15 mmol, 1 eq) and K$_2$CO$_3$ (1.7 g, 12.3 mmol, 2 eq) in EtOH (60 mL) is cooled in an ice bath, and thiophenol (0.631 mL, 6.15 mmol, 1 eq) is added. The reaction is monitored by HPLC until the starting material is consumed. The reaction mixture is filtered (to remove a solid by-product), and the solvent is removed in vacuo. The crude mixture is purified by silica gel chromatography using a Biotage Flash 40S column using 2% EtOAc in hexanes to afford ethyl 2-phenylsulfanyl-thiazole-5-carboxylate as an oil (0.784 g, 46%). MS (ESI) for C$_{12}$H$_{11}$NO$_2$S$_2$ m/z 266.1 (M+H)$^+$.

Step 19b

Potassium hydroxide (1.58 g, 28.2 mmol, 10 eq) is added to a solution of the product from Step 45a (0.748 g, 2.82 mmol, 1 eq) in EtOH (15 mL) and water (10.5 mL). The reaction is stirred for 1.5 hr, diluted with water (30 mL) and EtOH (30 mL), and acidified by addition of 3 N HCl until a white precipitate forms. The precipitate is filtered and purified by recrystallization from water and EtOH to give 2-phenylsulfanyl-thiazole-5-carboxylic acid as a white crystalline solid (0.307 g). MS (ESI) for $C_{10}H_7NO_2S_2$ m/z 235.9 (M−H)⁻.

Example 19 can be obtained using the coupling methods discussed herein.

EXAMPLE 20

N-[exo-4(S)-1-azabicyclo[2.2.1]hept-3-yl]-2-phenyl-1,3-thiazole-5-carboxamide

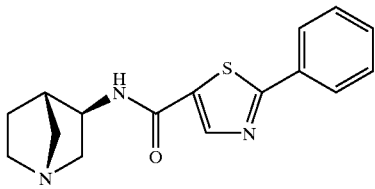

Step 20a

A solution of α-formyl-α-chloroacetate (9.34 g, 49.5 mmol, 1 eq) and thiobenzamide (6.79 g, 49.5 mmol, 1 eq) in EtOH (37.0 mL) is refluxed for 1 hr. The solution changes from an orange/brown color to a deep green. This solution is washed with water and extracted with $CH_2Cl_2$. The organic fraction is dried over $Na_2SO_4$, filtered, and the solvent removed in vacuo. The product is purified by column chromatography using a Biotage Flash 40M column (20% hexanes/EtOAc) to give ethyl 2-phenyl-thiazole-5-carboxylate as a deep orange oil (1.82 g, 15%). MS (ESI) for $C_{12}H_{13}NO_3S$ m/z 252.1 (M+H)⁺.

Making non-critical variations, Example 20 can be prepared using procedures discussed for Example 19.

EXAMPLE 21

N-[exo-4(S)-1-azabicyclo[2.2.1]hept-3-yl]-2-(2-fluorophenyl)-1,3-thiazole-5-carboxamide

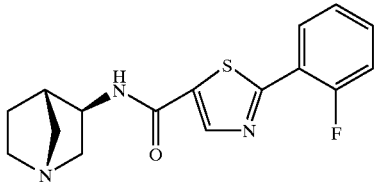

Step 21a

Tetrakis(triphenylphosphine)palladium (0) (0.58 g, 0.5 mmol), and a degassed solution of 2.0M $Na_2CO_3$ (10 mL) are added to a degassed solution of ethyl 2-bromo-1,3-thiazole-5-carboxylate (1.18 g, 5.0 mmol) and 2-fluorophenylboronic acid (0.77 g, 5.5 mmol) in DME (10 mL). The resulting suspension is stirred under argon at 80° C. for 4 hr. The reaction mixture is cooled, diluted with EtOAc, and then washed with two portions of 1.0 M NaOH, then one portion of brine. The combined organic phases are concentrated in vacuo, and the resulting oil purified with flash chromatography to give ethyl 2-(2-fluorophenyl)-1,3-thiazole-5-carboxylate. Yield 37%. HRMS (FAB) calculated for $C_{12}H_{10}FNO_2S+H$ 252.0495, found 252.0496.

Example 21 can be obtained by hydrolyzing the product from Step 21a and coupling using procedures discussed herein.

EXAMPLE 22

N-[exo-4(S)-1-azabicyclo[2.2.1]hept-3-yl]-2-(methylamino)-1,3-thiazole-5-carboxamide

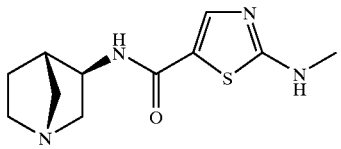

Step 22a

A flask is charged with a solution of ethyl 2-amino-1,3-thiazole-5-carboxylate (2.65 g, 15.4 mmol) and 4-dimethylaminopyridine (10 mg) in THF (75 mL). Di-(tert-butyl) dicarbonate (3.6 mL, 15.4 mmol,1.0 eq) and TEA (4.3 mL, 30.8 2.0 eq) are added, and the resulting solution is stirred at rt for 90 min. The reaction mixture is concentrated to dryness, and the crude product is crystallized from $CHCl_3$/hexanes to give ethyl 2-[(tert-butoxycarbonyl)amino]-1,3-thiazole-5-carboxylate as a light brown solid. Yield 68%. HRMS (FAB) calculated for $C_{11}H_{16}N_2O_4S+H$ 273.0909, found 273.0897.

Step 22b

A flask is charged with a suspension of sodium hydride (60% in mineral oil) (0.109 g, 2.72 mmol) in THF (5 mL). The ethyl 2-[(tert-butoxycarbonyl)amino]-1,3-thiazole-5-carboxylate (0.735 g, 2.70 mmol) is added, followed by iodomethane (175 µL, 2.70 mmol) and the resulting suspension is heated to reflux for 3 hr, then cooled to rt. Water is added, followed by 1.0 N NaOH. The basic phase is extracted with 3 portions of EtOAc. The combined organic phases are washed with brine, dried over $Na_2SO_4$, filtered, and concentrated to give a clear oil purified with flash chromatography to give ethyl 2-[(tert-butoxycarbonyl)(methyl)amino]-1,3-thiazole-5-carboxylate. Yield 45%. HRMS (FAB) calculated for $C_{12}H_{18}N_2O_4S+H$ 287.1065, found 287.1068.

Step 22c

The product of Step 22b is hydrolyzed according to Step 19b, making non-critical variations to give 2-[(tert-butoxycarbonyl)(methyl)amino]-1,3-thiazole-5-carboxylic acid. Yield 49%. HRMS (FAB) calculated for $C_{10}H_{14}N_2O_4S+H$ 259.0752, found 259.0750.

Step 22d

The product of Step 22c can be coupled according to Step 19c. The citrate can be prepared from the crude reaction mixture without chromatography, and crystallized until tert-butyl 5-([1-azabicyclo[2.2.1]oct-3-ylamino]carbonyl)-1,3-thiazol-2-yl(methyl)carbamate is of analytical purity.

Example 22 can be obtained by treating the product from Step 22d with a solution of 4.0N HCl/dioxane. The product can be crystallized from IPA/ether.

EXAMPLE 23

N-[exo-4(S)-1-azabicyclo[2.2.1]hept-3-yl]-5-(3-chlorophenyl)-1,3-oxazole-2-carboxamide

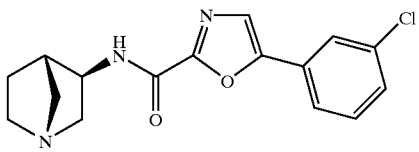

Step 23a

A mixture of 3-chlorophenylacyl bromide (5.18 g, 22.2 mmol, 1 eq), sodium diformylimide (2.11 g, 22.2 mmol, 1 eq) and $CH_3CN$ (125 mL) is heated in an 80° C. oil bath. After 3.5 h, the mixture is filtered and evaporated. The residue is treated with EtOH (40 mL) and HCl (10 mL, 12 N). The mixture was then heated in a 50° C. water bath for 30 min and evaporated. The resulting solid is triturated with acetone and collected by filtration to afford 2-amino-1-(3-chlorophenyl)ethanone hydrochloride (2.86 g, 62%). MS (ESI) for $C_8H_8ClNO$ m/z 170 $(M+H)^+$.

Step 23b

A mixture of the product from Step 23a (2.83 g, 13.7 mmol, 1 eq), ethyl chlorooxoacetate (1.87 g, 13.7 mmol, 1 eq), and $CH_2Cl_2$ (40 mL) is cooled in an ice-$H_2O$ bath. The mixture is treated with a solution of TEA (4.0 mL, 29 mmol, 2.1 eq) in $CH_2Cl_2$ (20 mL), and the reaction is warmed to rt overnight. Water is added and the organic layer is separated, dried over $MgSO_4$, filtered, and evaporated. The resulting solid is triturated with hexane/2-propanol and dried in vacuo to provide ethyl [[2-(3-chlorophenyl)-2-oxoethyl]amino](oxo) (2.70 g, 72%). MS (ESI) for $C_{12}H_{12}ClNO_4$ m/z 270 $(M+H)^+$.

Step 23c

A mixture of the product from Step 23b (1.28 g, 4.70 mmol, 1 eq), benzene (8 mL), and $POCl_3$ (2.0 mL, 21 mmol) is heated under reflux for 65 h and cooled. The mixture is then evaporated and extracted between $CHCl_3$ and water. The organic layer is separated, dried over $MgSO_4$, filtered, and evaporated. The residue is crystallized from EtOH to give ethyl 5-(3-chlorophenyl)-1,3-oxazole-2-carboxylate (0.61 g, 51%).

MS (ESI) for $C_{12}H_{10}ClNO_3$ m/z 252 $(M+H)^+$.

Example 23 can be obtained using coupling procedures discussed herein.

EXAMPLE 24

N-[exo-4(S)-1-azabicyclo[2.2.1]hept-3-yl]-4-methyl-5-phenyl-1,3-thiazole-2-carboxamide

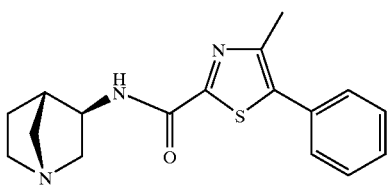

Step 24a

2-Bromo-1-phenylpropan-1-one (8.97 g, 42.1 mmol, 1 eq) is added dropwise to a suspension of diformylimide sodium salt (4.80 g, 50.5 mmol, 1.2 eq) in 80 mL $CH_3CN$. The reaction is stirred for 60 h at 70–75° C. The hot mixture is filtered to remove the salts and the solids are washed with $CH_3CN$. The combined filtrates are concentrated in vacuo, dissolved in 40 mL 6N HCl and heated under reflux for 0.75 h. The solvents are removed under reduced pressure and the product is recrystallized from IPA to give 2-amino-1-phenylpropan-1-one hydrochloride (6.15 g, 79%). MS (ESI) for $C_9H_{11}NO$ m/z 150.2 $(M+H)^+$.

Step 24b

TEA (3.22 mL, 0.0231 mol, 2.1 eq) is added dropwise to a suspension of the product from Step 24a (2.05 g, 11.0 mmol, 1 eq) and ethyl oxalyl chloride (1.24 mL, 11.0 mmol, 1 eq) in 50 mL $CH_2Cl_2$ in an ice/water bath. The mixture is allowed to slowly warm to rt. After stirring overnight, water and 20 mL 1N HCl are added. The aqueous layer is extracted with $CH_2Cl_2$. The combined organic layers are dried over $MgSO_4$, filtered and concentrated to give ethyl [(1-methyl-2-oxo-2-phenylethyl)amino](oxo)acetate as a yellow oil (2.58 g, 94%). MS (ESI) for $C_{13}H_{15}NO_4$ m/z 250.2 $(M+H)^+$.

Step 24c

The product from Step 24b (2.58 g, 10.4 mmol, 1 eq) and $P_2S_5$ (4.83 g, 10.9 mmol, 1.05 eq) are suspended in 30 mL $CHCl_3$. The mixture is heated under reflux. After 12 h, water and solid $K_2CO_3$ are carefully added until all material dissolves. The aqueous layer is made sufficiently basic with 1N NaOH (pH more than 10) and extracted with EtOAc. The combined organic layers are washed with 1N NaOH and brine, dried over $MgSO_4$, filtered and concentrated to give ethyl 4-methyl-5-phenyl-1,3-thiazole-2-carboxylate as a yellow oil (2.51 g, 98%). MS (ESI) for $C_{13}H_{13}NO_2S$ m/z 248.1 $(M+H)^+$.

Example 24 can be obtained using coupling methods discussed herein.

EXAMPLE 25

N-[exo-4(S)-1-azabicyclo[2.2.1]hept-3-yl]-5-phenyl-furan-2-carboxamide.fumarate

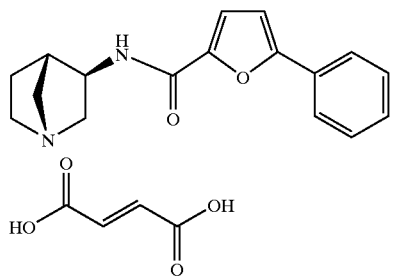

Step 25a

A solution of 5-bromo-furan-2-carbaldehyde (1.08 g, 6.16 mmol, 1 eq), phenylboronic acid (0.90 g, 7.39 mmol, 1.1 eq), tetrabutylammonium bromide (1.99 g, 6.16 mmol, 1 eq), palladium acetate (30 mg, 0.0.12 mmol 0.02 eq), $K_2CO_3$ (2.13 g, 15.4 mmol, 2.5 eq) in water (10 mL) is stirred under nitrogen at rt overnight. The reaction is diluted with 40 mL water and extracted with EtOAc (3×100 mL). The organic layers are combined and stirred with charcoal for 30 min, then dried over $MgSO_4$ and filtered. The solvent is removed under reduced pressure to give 5-phenyl-furan-2-carbaldehyde as an oil. The product is purified by silica gel chromatography using a Biotage Flash 40M column (10% EtOAc/heptane).

Step 25b

To a solution of the product from Step 25a (0.650 g, 3.78 mmol, 1 eq) in water (5.5 mL), t-BuOH (18.0 mL), and THF (18.0 mL) is added 2-methyl-2-butene (3.2 mL, 30.2 mmol, 8 eq), potassium phosphate monobasic (1.54 g, 11.3 mmol, 3 eq), then NaClO₂ (1.03 g, 11.3 mmol, 3 eq) in that order. After 4 hr, the reaction is complete and diluted with 1 N NaOH (100 mL). The aqueous solution is extracted with ether (2×100 mL), and the aqueous layer is acidified with conc. HCl. The resulting solution is extracted with $CH_2Cl_2$ (3×100 mL). The organic layers are dried over $MgSO_4$, and the solvent removed. 5-Phenyl-furan-2-carboxylic acid is purified by silica gel chromatography using a Biotage Flash 40M column (10% EtOAc/1% formic acid/heptane). The solid remaining after removal of the solvent is filtered and recrystallized from EtOH and water to give the acid as a white crystalline solid (0.499 g, 70.2%). HRMS (FAB) calculated for $C_{11}H_8O_3$+H 189.0473, found 189.0403.

Following the procedure of Step 3c, the free base of Example 25 is obtained in quantitative yield as a light yellow solid: MS (ESI) m/e 283 [M+H].

Following the procedure of
Step 3d, Example 25 is obtained in 80% yield as a white solid: ¹H NMR (DMSO-d₆) δ 8.3, 7.9, 7.5, 7.4, 7.2, 7.1, 6.5, 3.8, 3.1, 3.0–2.8, 2.7–2.6, 1.8–1.7, 1.3.

The following examples are prepared from the requisite boronic acid, furaldehyde, or furan-carboxylic acid according to the procedures for Example 25, making non-critical variations.

EXAMPLE 26

N-[exo-4(S)-1-azabicyclo[2.2.1]hept-3-yl]-5-(2-fluorophenyl)-furan-2-carboxamide.fumarate (from 2-fluorophenylboronic acid). ¹H NMR (DMSO-d₆) δ 8.4, 8.1, 7.5–7.4, 7.3, 7.0, 6.6, 3.8, 3.1, 3.0–2.8, 2.6, 1.8–1.7, 1.3.

EXAMPLE 27

N-[exo-(4S)-1-azabicyclo[2.2.1]hept-3-yl]-5-(3-fluorophenyl)-furan-2-carboxamide (from 3-fluorophenylboronic acid). The yield for the coupling and obtaining the salt is 62.5%. ¹H NMR (400 MHz, CD₃OD): 7.96–7.92, 7.26, 7.24–7.20, 6.93, 6.71, 4.23, 3.66, 3.45–3.35, 3.21–3.18, 3.06, 2.16, 1.82.

EXAMPLE 28

N-[exo-(4S)-1-azabicyclo[2.2.1]hept-3-yl]-5-(4-fluorophenyl)-furan-2-carboxamide (from 4-fluorophenylboronic acid). The yield for the coupling and obtaining the salt is 50%. ¹H NMR (400 MHz. CD₃OD): 7.74–7.70, 7.48, 7.28, 7.13, 7.04, 6.71, 4.28, 3.72, 3.52–3.38, 3.27–3.25, 3.08, 2.20, 1.80.

EXAMPLE 29

N-[exo-4(S)-1-azabicyclo[2.2.1]hept-3-yl]-5-(2,3-difluorophenyl)-furan-2-carboxamide

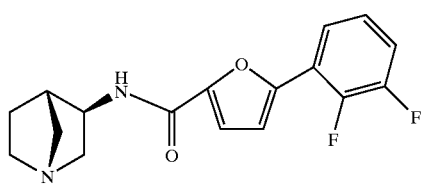

Example 29 can be obtained in the following way: N-[exo-4(S)-1-azabicyclo[2.2.1]hept-3-yl]-5-bromo-furan-2-carboxamide (1 eq), 2,3-difluorophenylboronic acid (1.1 eq), and tetrabutylammonium bromide (1 eq), palladium acetate (0.02 eq), $K_2CO_3$ (3.5 eq) are stirred in an amount of water to afford about a 0.6M concentration of the carboxamide. The reaction is stirred under argon overnight. The reaction is purified by silica gel chromatography using a Biotage Flash system.

Example 30 is prepared from the requisite boronic acid and N-[exo-4(S)-1-azabicyclo[2.2.1]hept-3-yl]-5-bromo-furan-2-carboxamide, making non-critical variations:

EXAMPLE 30

N-[exo-4(S)-1-azabicyclo[2.2.1]hept-3-yl]-5-(4-methylphenyl)-furan-2-carboxamide.fumarate (from p-tolylboronic acid). ¹H NMR (DMSO-d₆) δ 6 8.3, 7.8, 7.3, 7.2, 7.0, 6.6, 3.8, 3.2–3.1, 3.0–2.8, 2.7, 2.3, 1.8–1.7, 1.3.

EXAMPLE 31

5-(2-Aminophenyl)-N-[exo-4(S)-1-azabicyclo[2.2.1]hept-3-yl]-furan-2-carboxamide

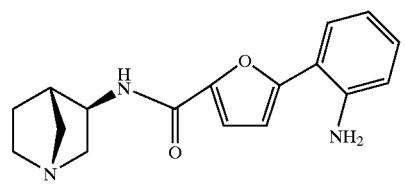

Example 31 can be prepared by the following: To a solution of N-[1-aza-bicyclo[2.2.1]oct-3-yl]-5-(2-nitrophenyl)-furan-2-carboxamide in was added Pd/C (10 mol %). This mixture was placed on a Parr shaker under 40 psi hydrogen until starting material is consumed. The palladium is removed by filtration over a pad of celite, and the solvent is removed.

EXAMPLE 32

N-[exo-4(S)-1-azabicyclo[2.2.1]hept-3-yl]-5-(phenylethynyl)-furan-2-carboxamide

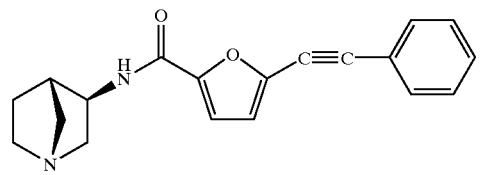

Step 32a

To a solution of 5-bromofuraldehyde (1.0 g, 5.71 mmol, 1 eq), copper (I) iodide (0.163 g, 0.857 mmol, 0.15 eq), trans-dichlorobis(triphenylphosphine) palladium(II) (0.20 g, 0.287 mmol, 0.05 eq), and TEA (3.98 mL, 28.6 mmol, 5 eq) in THF (45 mL) is added dropwise phenyl acetylene (1.25 mL, 11.4 mmol, 2 eq). After 48 hr, the reaction appears complete. The reaction is filtered over a pad of celite, and the solvent is removed under reduced pressure. The reaction is purified by silica gel chromatography using a Biotage Flash 40M column (10% EtOAc/heptane) to give 5-phenylethynyl-furan-2-aldehyde as a yellow orange crystalline solid (0.765 g, 68.3%).

MS (ESI) for $C_{13}H_8O_2$ m/z 197.1 (M+H)⁺.

Following the general procedure of Example 25, making non-critical variations but starting with 5-phenylethylnyl-furan-2-aldehyde, Example 32 can be synthesized.

EXAMPLE 33

N-[exo-4(S)-1-azabicyclo[2.2.1]hept-3-yl]-5-phenoxy-furan-2-carboxamide

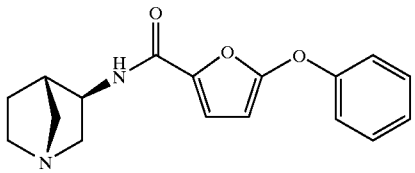

Example 33 can be obtained as follows: A solution of N-[exo-4(S)-1-azabicyclo[2.2.1]hept-3-yl]-5-bromo-furan-2-carboxamide (1 eq), sodium phenoxide (10.1 eq), in DMSO (for about 1.0 M solution of the carboxamide) is stirred under nitrogen at rt overnight. The reaction is diluted with water and extracted with $CH_2Cl_2$. The organic layer is washed with water, satd $NaHCO_3$, brine, and dried over $MgSO_4$ to afford the desired product.

EXAMPLE 34

N-[exo-4(S)-1-azabicyclo[2.2.1]hept-3-yl]-1-methyl-5-phenyl-1H-pyrrole-2-carboxamide

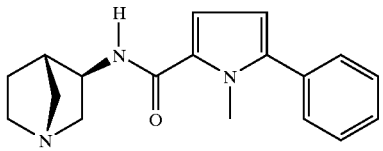

Step 34a

To a dry flask is added methyl 1-methyl-1H-pyrrole-2-carboxylate (12.0 g, 86.4 mmol) and 150 mL of dry $CH_2Cl_2$, and the flask is wrapped in foil and purged with nitrogen. N-Bromosuccinimide (16.2 g, 90.7 mmol) is added in one portion and the mixture is stirred at rt for 0.5 h. The reaction mixture is washed with water (50 mL) and brine (50 mL), dried over $MgSO_4$, filtered, and concentrated under reduced pressure. Fractional distillation gives 12.0 g of methyl 5-bromo-1-methyl-1H-pyrrole-2-carboxylate as a yellow oil (64% yield). MS for $C_7H_8NO_2Br$ (ESI) (M)+ m/z 217.1.

Step 34b

The product from step 34a is added to a solution of tetrakis(triphenylphosphine)palladium(0) (0.530 g, 0.459 mmol) in 90 mL of ethylene glycol dimethyl ether. The resulting solution is stirred under nitrogen for 5 min and then phenylboronic acid (1.34 g, 11.0 mmol) is added followed by a solution of $Na_2CO_3$ (19.5 g, 183 mmol) in 90 mL of $H_2O$. The mixture is heated at reflux for 24 hr. The reaction mixture is allowed to cool to rt, 100 mL of $CH_2Cl_2$ is added, and the layers are separated. The aqueous layer is extracted with $CH_2Cl_2$ (3×50 mL) and combined organic layers are dried over $MgSO_4$, filtered, and concentrated in vacuo. The crude product is purified by flash column chromatography (5% EtOAc in hexane) to give 1.89 g of methyl 1-methyl-5-phenyl-1H-pyrrole-2-carboxylate as a yellow oil (96% yield). MS for $C_{13}H_{13}NO_2$ (ESI) (M+H)+ m/z 216.1.

Step 152c

Lithium hydroxide (1.39 g, 33.2 mmol) is added to a solution of the product from Step 34b (1.43 g, 6.64 mmol) in 96 mL of a 1.25:1:1 $H_2O$:MeOH:THF solvent mixture. The reaction is stirred at 50° C. for 2 h. Aqueous HCl (1N, 50 mL) is added and the resultant precipitate is collected by filtration, washed with water, and dried to give 0.851 g of 1-methyl-5-phenyl-1H-pyrrole-2-carboxylic acid as a tan solid (64% yield). MS for $C_{12}H_{11}NO_2$ (ESI) (M–H)+ m/z 200.1.

Example 34 can be obtained using coupling procedures discussed herein.

EXAMPLE 35

N-[exo-4(S)-1-azabicyclo[2.2.1]hept-3-yl]-5-phenyl-1,3-oxazole-2-carboxamide.fumarate

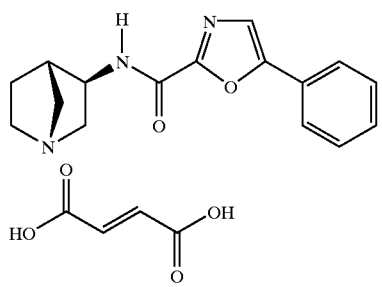

Step 35a

To a stirred solution of 120 mg (0.63 mmol) of 5-phenyl-1,3-oxazole-2-carboxylic acid (see: Saito, S.; Tanaka, C., *J. Pharm. Sci. Japan*, 76, 1956, 305–7) in dry DMF (10 mL) is added DIEA (2.33 mL, 1.34 mmol), followed by exo-4(S)-[2.2.1]-3-Amine (200 mg, 0.44 mmol). The solution is cooled with an ice bath before 167 mg (0.44 mmol) of HATU is added. The solution is allowed to warm to rt and stir for 16 h. The solvent is removed in vacuo, and the remaining residue is partitioned between saturated aqueous $K_2CO_3$ solution and 9:1 $CHCl_3$—MeOH. The aqueous layer is extracted with 9:1 $CHCl_3$-MeOH, and the combined organic layers are washed with brine, dried over $MgSO_4$, filtered and concentrated in vacuo to afford the free base of Example 35 as a light yellow solid (91 mg, 73%): MS for $C_{16}H_{17}O_2N_3$ (ESI) m/e 284 (M+H)+.

To a stirred solution of the product from Step 35a (91 mg, 0.32 mmol) in acetone (2 mL) is added a hot solution of fumaric acid (37 mg, 0.32 mmol) in IPA (2 mL). The mixture is stirred for 30 min in a 50° C. water bath. The solvents are removed in vacuo and the remaining residue is dissolved in acetone (5 mL). The mixture is stirred overnight at rt. The solid precipitate is collected by filtration and washed with acetone. The solid is dried in vacuo overnight to give 96 mg (75%) of Example 35 as a white solid: $^1$H NMR (DMSO-$d_6$) δ 9.1, 7.9, 7.8, 7.5, 7.4, 6.5, 3.8, 3.1, 3.0–2.8, 2.6, 1.7, 1.3.

The following examples can be prepared using the coupling procedure for Example 35, making non-critical variations and using the appropriate carboxylic acids.

EXAMPLE 36

N-[exo-4(S)-1-azabicyclo[2.2.1]hept-3-yl]-2-phenyl-1,3-oxazole-5-carboxamide (from 2-phenyl-1,3-oxazole-5-carboxylic acid, see Belen'kii, L. I.; Cheskis, M. A.; Zvolinskii, V. P.; Obukhov, A. E. *Chem. Heterocycl. Compd.* (*Engl. Transl.*); 22; 1986; 654–663).

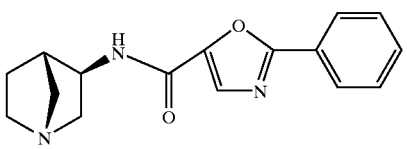

EXAMPLE 37

N-[exo-4(S)-1-azabicyclo[2.2.1]hept-3-yl]-2-phenyl-1,3-oxazole-4-carboxamide (from 2-phenyl-1,3-oxazole-4-carboxylic acid, see Korte, F.; Stoeriko, K. *Chem. Ber.*; 93; 1960; 1033–1042).

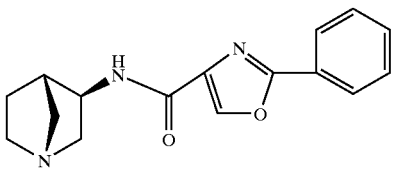

EXAMPLE 38

N-[exo-4(S)-1-azabicyclo[2.2.1]hept-3-yl]-5-phenylisoxazole-3-carboxamide (from 5-phenylisoxazole-3-carboxylic acid, see Vaughan, W. R.; Spencer, J. L. *J. Org. Chem.*; 25; 1960; 1160–1164).

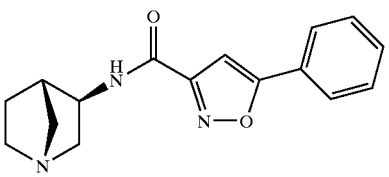

EXAMPLE 39

N-[exo-4(S)-1-azabicyclo[2.2.1]hept-3-yl]-5-phenyl-thiophene-2-carbothioamide

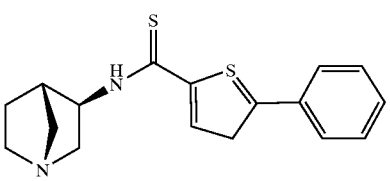

Step 39a

To a cooled (−10 to 0° C.) solution of n-BuLi (22.7 mL, 33.4 mmol) in THF (10 mL) is added dropwise a solution of 2-phenyl-thiophene (5.46 g, 34.0 mmol) in THF (15 mL). The resulting green solution is stirred at 0° C. After 30 minutes, a solution of copper (I) bromide (0.87 g, 6.1 mmol) and lithium bromide (1.29 g, 14.9 mmol) in THF (20 mL) is added to the cooled reaction solution over several minutes. The resulting dark green solution is stirred at 0° C. for 15 minutes, at which time, carbon disulfide (2.0 mL, 34.0 mmol) is added dropwise over 15 minutes. The resulting dark brown solution is stirred for 30 minutes, then iodomethane (2.9 mL, 46.4 mmol) is added dropwise to the reaction solution over 5 minutes. The resulting dark brown solution is allowed to warm to room temperature and stirred for 1 hour, then is quenched with a solution of potassium cyanide in water (100 mL). The biphasic mixture was diluted with EtOAc and washed with brine, dried over MgSO$_4$, filtered, and concentrated to give a dark orange solid (8.5 grams) which is purified with flash chromatography on silica gel (eluent: gradient of heptane to 2% THF/heptane) to give methyl 5-phenyl-thiophene-2-carbodithioate as an orange solid. Yield 34%. HRMS (FAB) calculated for C$_{12}$H$_{10}$S$_3$+H 251.0023, found 251.0023.

Example 39 can be obtained using coupling procedures discussed herein.

EXAMPLE 40

N-[(exo)-1-azabicyclo[3.2.1]oct-3-yl]-5-phenyl-1,3-oxazole-2-carboxamide

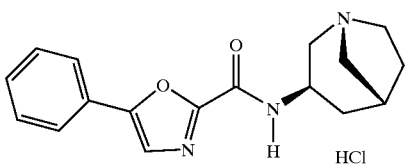

A mixture of exo-[3.2.1]-Amine (0.270 g, 1.36 mmol), 5-phenyl-1,3-oxazole-2-carboxylic acid (see: Saito, S.; Tanaka, C., *J. Pharm. Sci. Japan*, 76, 1956, 305-7) (0.256 g, 1.36 mmol), THF (15 mL), DIEA (0.7 mL, 4.10 mmol), and DMF (4 mL) is cooled in an ice bath and treated with HATU (0.516 g, 1.36 mmol). The mixture warmed to rt and is evaporated. The residue is diluted with CHCl$_3$ and washed with aqueous NaOH (1N). The organic layer is dried (MgSO$_4$), filtered, evaporated, and the resulting oil purified by flash column chromatography (1:6:90; conc. NH$_4$OH-MeOH—CHCl$_3$). The hydrochloride salt is formed and triturated with EtOAc/hexane to yield Example 40 (0.246 g, 54%). MS for C$_{17}$H$_{19}$N$_3$O$_2$.HCl (ESI) (MH)$^+$ m/z=298.

EXAMPLE 41

N-[(3R,5R)-1-azabicyclo[3.2.1]oct-3-yl]-5-bromothiophene-2-carboxamide hydrochloride

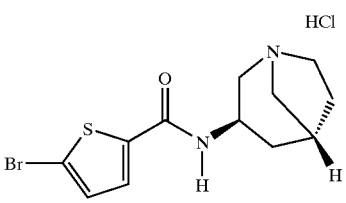

The free base of Example 41 is obtained following the procedures for Example 40, and using 3R,5R-[3.2.1]-Amine as the amine. The free base is treated with MeOH/HCl, evaporated, triturated (EtOH/Et$_2$O) and dried in vaccuo to afford Example 41 as a solid in 87% yield from the coupling: $^1$H NMR (400 MHz, DMSO-d$_6$) d 10.61, 8.70–8.85, 7.71, 7.31, 4.30–4.55, 3.05–3.55, 2.65–2.75, 2.00–2.20, 1.80–1.95, 1.65–1.80.

EXAMPLE 42

N-[(3R,5R)-1-Azabicyclo[3.2.1]oct-3-yl]-5-phenyl-2-furan-carboxamide hydrochloride

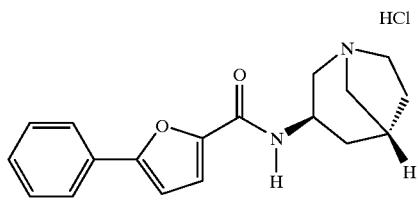

The free base of Example 42 is obtained following Example 40, and using 3R,5R-[3.2.1]-Amine as the amine. The crude material is treated with MeOH/HCl, evaporated, triturated (Et₂O) and dried in vaccuo to afford Example 42 as a foam in 68% yield from the coupling; ¹NMR (400 MHz, DMSO-d₆) d 8.35–8.45, 7.90; 7.49; 7.39; 7.23; 7.12; 4.40–4.65, 3.05–3.55, 2.65–2.75, 2.05–2.20, 1.85–2.00, 1.75–1.85

EXAMPLE 43

N-[(3R,5R)-1-azabicyclo[3.2.1]oct-3-yl]-5-(2-fluorophenyl)-furan-2-carboxamide hydrochloride

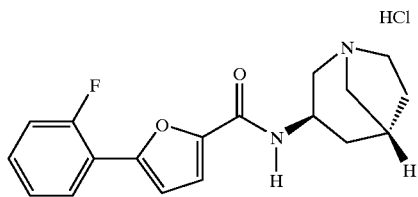

The free base of Example 43 is obtained following Example 40, and using 3R,5R-[3.2.1]-Amine as the amine. The crude material is treated with MeOH/HCl, evaporated, triturated (EtOH/Et₂O) and dried in vaccuo to afford Example 43 as a solid in 72% yield from the coupling: ¹NMR (400 MHz, DMSO-d₆) d 10.75, 8.50–8.65, 8.13, 7.35–7.55, 7.29, 6.97, 4.40–4.60, 3.10–3.60, 2.65–2.80, 2.05–2.22, 1.75–2.05

EXAMPLE 44

N-[(3R,5R)-1-azabicyclo[3.2.1]oct-3-yl]-5-phenyl-1,3-oxazole-2-carboxamide hydrochloride

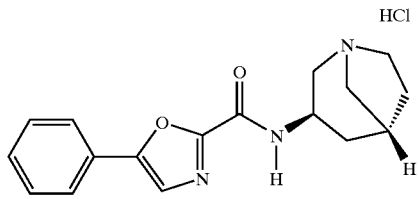

A mixture of 5-phenyl-1,3-oxazole-2-carboxylic acid (0.241 g), 3R,5R-[3.2.1]-Amine (0.221 g), ethanol (7 mL) and sodium ethoxide (0.153 g) is heated at 100° C. After 36 h, the mixture is concentrated and partitioned between EtOAc and H₂O. The organic layers are separated, dried (MgSO₄), filtered and concentrated. The crude product is chromatographed (Biotage 40S, (1:9:89) NH₄OH-MeOH—CHCl3). The product fractions are pooled, concentrated, treated with EtOH, and concentrated again. The residue is treated with MeOH/HCl, evaporated, triturated (EtOH/Et₂O) and dried in vaccuo to afford 0.128 g (35%) of Example 44 as a solid: ¹H NMR (400 MHz, DMSO-d₆) d 10.67, 8.95–9.05, 7.95, 7.83, 7.54, 7.46, 4.40–4.55, 3.05–3.60, 2.65–2.75, 2.05–2.20, 1.75–2.00.

EXAMPLE 45

5-[4-(acetylamino)phenyl]-N-[(3R,5R)-1-azabicyclo[3.2.1]oct-3-yl]-1,3-oxazole-2-carboxamide (2E)-but-2-enedioic acid

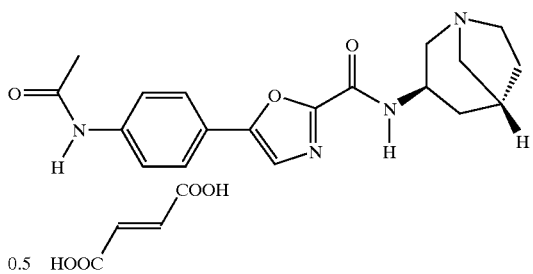

A mixture of 3R,5R-[3.2.1]-Amine (0.600 g), ethyl 5-(4-nitrophenyl)-1,3-oxazole-2-carboxylate (1.11 g), ethanol (20 mL) and sodium ethoxide (0.429 g) is heated in a 100° C. oil bath for 16 h. Then additional ethyl 5-(4-nitrophenyl)-1,3-oxazole-2-carboxylate (0.111 g) is added and heating continued for 4 h. The mixture is cooled, concentrated and the residue partitioned between EtOAc/1 N NaOH. The organic layer is separated, dried (MgSO₄), filtered and evaporated. The residue is chromatographed (Biotage 40S, 1:10:89-NH₄OH-MeOH—CHCl₃) and product fractions pooled and concentrated to afford 0.463 g of the intermediate N-[(3R,5R)-1-azabicyclo[3.2.1]oct-3-yl]-5-(4-nitrophenyl)-1,3-oxazole-2-carboxamide as a solid:

MS (ESI+) m/z (MH+) 343.

A mixture of nitro intermediate (0.444 g), 10% Pd/C (0.223 g) and MeOH (40 mL) is shaken under H₂ (45 PSI) for 16 h. The mixture is then filtered through Celite and HCl in methanol is added. The mixture is concentrated to give 0.286 g of Example 165 as a solid: MS (ESI+) m/z (MH+) 313.

An ice chilled suspension of 5-(4-aminophenyl)-N-[(3R,5R)-1-azabicyclo[3.2.1]oct-3-yl]-1,3-oxazole-2-carboxamide (0.294 g), CH₂Cl₂ (20 mL), and acetyl chloride (0.07 mL) is treated with TEA (0.59 ml) under N₂. Additional acetyl chloride (0.02 mL) is added and the mixture allowed to warm to rt overnight. After 16 h, the mixture is diluted with water (~10 mL) and 1 N NaOH (~2 mL). The organic layer is collected, dried (MgSO₄), filtered and chromatographed (Biotage 40 S, 1:9:90-NH₄OH:MeOH:CHCl₃). The product fractions are pooled, concentrated, treated with 1.0 eq. fumaric acid, and EtOH (~10 ml). The mixture is concentrated and the resulting solid was triturated with EtOH/Et₂O. The solid is collected and dried in a vacuum oven at 50° C. overnight to afford 0.069 g of Example 45 as a solid:

¹H NMR (400 MHz, DMSO-d₆) d 10.19, 8.70–8.80, 7.70–7.85, 6.49, 4.20–4.35, 3.44, 2.90–3.15, 2.75–2.90, 2.60–2.70, 2.40–2.50, 2.07, 1.70–1.90, 1.05.

EXAMPLE 46

N-(1-azabicyclo[3.2.2]non-3-yl)-5-bromothiophene-2-carboxamide 4-methylbenzenesulfonate

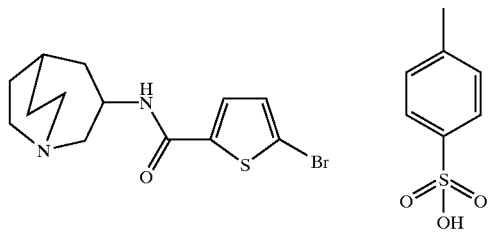

To a stirred solution of [3.2.2]-Amine (310 mg, 0.64 mmol) in DMF (8.0 mL) in a 0° C. ice bath is added sequentially DIEA (334 μL, 1.92 mmol), 5-bromothiophene-2-carboxylic acid (140 mg, 0.67 mmol) and HATU (243 mg, 0.64 mmol). The mixture is stirred in the 0° C. ice bath for 15 min, followed by warming to rt and stirring overnight. The mixture is concentrated in vacuo to a brown residue. The residue is partitioned between saturated aqueous potassium carbonate solution and CHCl$_3$-MeOH (90:10). The aqueous layer is extracted with CHCl$_3$-MeOH (90:10), and the combined organic layers are washed with brine, dried over anhydrous MgSO$_4$, filtered and concentrated in vacuo. The crude product is purified by flash chromatography on silica gel. Elution with CHCl$_3$-MeOH—NH$_4$OH (95:4.5:0.5) to give 119 mg (56%) of a solid.

To a stirred solution of the solid (19 mg, 0.36 mmol) in acetone is added p-toluenesulfonic acid mono hydrate (69 mg, 0.36 mmol). The solution is heated in a water bath at 45° C. for 30 min, followed by concentration of the solvent in vacuo. EtOAc (3.0 mL) is added to the residue, which caused a solid to precipitate. The solid is filtered and dried in vacuo to give 164 mg (87%) of Example 46 as a white solid: $^1$H NMR (CD$_3$OD) δ 8.4, 7.7, 7.5, 7.3, 7.2, 4.6, 3.8, 3.6, 3.5, 3.4, 3.2, 2.4–2.3, 2.2–2.0, 1.9.

Materials and Methods for Determining α7 nAChR Agonist Activity

Cell-based Assay for Measuring the EC$_{50}$ of α7 nAChR Agonists

Construction and Expression of the α7-5HT$_3$ Receptor:

The cDNA encoding the N-terminal 201 amino acids from the human α7 nAChR that contain the ligand binding domain of the ion channel is fused to the cDNA encoding the pore forming region of the mouse 5HT$_3$ receptor as described by Eisele J L, et al., Chimaeric nicotinic-serotonergic receptor combines distinct ligand binding and channel specificities, Nature (1993), December 2;366(6454):479–83, and modified by Groppi, et al., WO 00/73431. The chimeric α7-5HT$_3$ ion channel is inserted into pGS175 and pGS179 which contain the resistance genes for G-418 and hygromycin B, respectively. Both plasmids were simultaneously transfected into SH-EP1 cells and cell lines were selected that were resistant to both G-418 and hyrgromycin B. Cell lines expressing the chimeric ion channel were identified by their ability to bind fluorescent (α-bungarotoxin on their cell surface. The cells with the highest amount of fluorescent α-bungarotoxin binding were isolated using a Fluorescent Activated Cell Sorter (FACS). Cell lines that stably expressed the chimeric α7-5HT$_3$ were identified by measuring fluorescent α-bungarotoxin binding after growing the cells in minimal essential medium containing nonessential amino acids supplemented with 10% fetal bovine serum, L-glutamine, 100 units/ml penicillin/streptomycin, 250 ng/mg fungizone, 400 μg/ml hygromycin B, and 400 μg/ml G-418 at 37° C. with 6% CO$_2$ in a standard mammalian cell incubator for at least 4 weeks in continuous culture.

Assay of the Activity of the Chimeric α7-5HT$_3$ Receptor

To assay the activity of the α7-5HT$_3$ ion channel, cells expressing the channel were plated into each well of either a 96 or 384 well dish (Corning #3614) and grown to confluence prior to assay. On the day of the assay, the cells were loaded with a 1:1 mixture of 2 mM Calcium Green 1, AM (Molecular Probes) dissolved in anhydrous DMSO and 20% pluronic F-127 (Molecular Probes). This solution is added directly to the growth media of each well to achieve a final concentration 2 μM. The cells were incubated with the dye for 60 min at 37° C. and then washed with a modified version of Earle's balanced salt solution (MMEBSS) as described in WO 00/73431. The ion conditions of the MMEBSS is adjusted to maximize the flux of calcium ion through the chimeric α7-5HT$_3$ ion channel as described in WO 00/7343 1. The activity of compounds on the chimeric α7-5HT$_3$ ion channel is analyzed on FLIPR. The instrument is set up with an excitation wavelength of 488 nanometers using 500 milliwatts of power. Fluorescent emission is measured above 525 nanometers with an appropriate F-stop to maintain a maximal signal to noise ratio. Agonist activity of each compound is measured by directly adding the compound to cells expressing the chimeric α7-5HT$_3$ ion channel and measuring the resulting increase in intracellular calcium that is caused by the agonist-induced activation of the chimeric ion channel. The assay is quantitative such that concentration-dependent increase in intracelluar calcium is measured as concentration-dependent change in Calcium Green fluorescence. The effective concentration needed for a compound to cause a 50% maximal increase in intracellular calcium is termed the EC$_{50}$. The following examples of the present invention have EC$_{50}$ values from about 30 nM to about 16,000 nM: Examples 1–3, 11, 25–29, 30, 35, 40–46.

Binding Constants:

Another way for measuring α7 nAChR agonist activity is to determine binding constants of a potential agonist in a competition binding assay. For α7 nAChR agonists, there is good correlation between functional EC$_{50}$ values using the chimeric α7-5HT$_3$ ion channel as a drug target and binding affinity of compounds to the endogenous α7 nAChR.

Membrane Preparation.

Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at rt and diluted with Kreb's −20 mM Hepes buffer pH 7.0 (at rt) containing 4.16 mM NaHCO$_3$, 0.44 mM KH$_2$PO$_4$, 127 mM NaCl, 5.36 mM KCl, 1.26 mM CaCl$_2$, and 0.98 mM MgCl$_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay.

For saturation studies, 0.4 mL homogenate are added to test tubes containing buffer and various concentrations of radioligand, and are incubated in a final volume of 0.5 mL for 1 hour at 25° C. Nonspecific binding is determined in tissues incubated in parallel in the presence of 0.05 mls MLA for a final concentration of 1 μM, added before the radioligand. In competition studies, drugs are added in increasing concentrations to the test tubes before addition of 0.05 mls [$^3$H]-MLA for a final concentration 3.0 to 4.0 nM. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis.

In competition binding studies, the inhibition constant (Ki) is calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

What is claimed:

1. A compound of Formula I:

Azabicyclo-N(R$_1$)—C(=X)—W  Formula I wherein, X is O or S;

R$_1$ is H, alkyl, cycloalkyl, halogenated alkyl, or aryl;

W is a cyclic heteroaromatic moiety where the heteroatoms can be from 1–2 atoms selected from oxygen, sulfur, or nitrogen of the following structures:

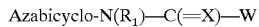

(a)

or (b)

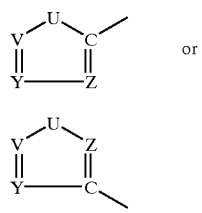

wherein U is —O— or —S—;

V and Y are independently =N—, or =C(R$_{VY}$)—;

Z is =N—, or =CH—, provided that when both V and Y are =C(R$_{VY}$)— and Z is =CH—, only one =C(R$_{VY}$)— can be =CH—, further provided that when U is —O—, Y is =C(R$_{VY}$)— and Z is =C(H)—, V cannot be =N—, and further provided that no more than one of V, Y, or Z is a heteroatom;

R$_U$ is H, alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —SO$_2$R$_8$;

Each R$_{VY}$ is independently H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —OR$_8$, —OR$_{14}$, —SR$_8$, —SR$_{14}$, F, Cl, Br, I, —NR$_8$R$_8$, —NR$_{14}$R$_{14}$, —C(O)R$_8$, —C(O)R$_{14}$, —C(O)NR$_8$R$_8$, —C(O)NR$_{14}$R$_{14}$, —C(R$_6$)=N(R$_{16}$), —CN, —NR$_8$C(O)R$_{11}$, —S(O)$_2$NR$_8$R$_8$, —OS(O)$_2$R$_{11}$, —S(O)$_2$R$_8$, —S(O)$_2$R$_{14}$, —NR$_8$S(O)$_2$R$_8$, —N(H)C(O)N(H)R$_8$, —NO$_2$,R$_7$R$_9$, or 0–3 substituents independently selected from F, Cl, Br, I, or R$_{15}$;

Azabicyclo is

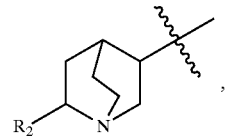

I

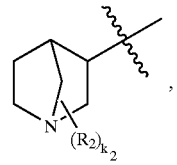

II

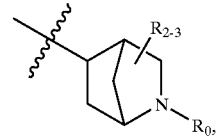

III

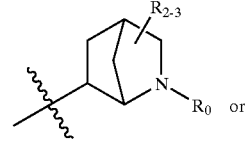

IV

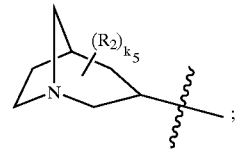

V

R$_0$ is H, lower alkyl, substituted lower alkyl, or halogenated lower alkyl;

R$_2$ is alkyl, halogenated alkyl, substituted alkyl, cycloalkyl, aryl or R$_2$ is absent provided that k$_2$, k$_5$, or k$_6$ is 0;

k$_2$ is 0 or 1;

k$_5$ and k$_6$ are independently 0, 1, or 2;

R$_{2-3}$ is H, alkyl, halogenated alkyl, substituted alkyl, F, Cl, Br, or I;

R$_6$ is H, F, Cl, CN, alkyl, substituted alkyl, cycloalkyl, halogenated alkyl, and aryl;

R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is a 9-membered fused-ring moiety having a 6-membered ring fused to a 5-membered ring and having the formula

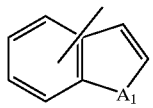

wherein $A_1$ is O, S, or $NR_{19}$,

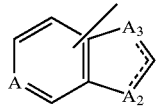

wherein A is $CR_{18}$ or N, $A_2$ and $A_3$ are independently selected from $CR_{18}$, $C(R_{18})_2$, O, S, N, or $NR_{19}$, provided that both $A_2$ and $A_3$ are not simultaneously O, simultaneously S, or simultaneously O and S, or

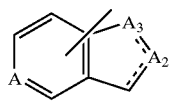

wherein A is $CR_{18}$ or N, $A_2$ and $A_3$ are independently selected from $CR_{18}$, $C(R_{18})_2$, O, S, N, or $NR_{19}$, each 9-membered fused-ring moiety having 0–1 substituent selected from $R_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from F, Cl, Br, or I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from F, Cl, Br, or I, and having a bond directly or indirectly attached to the core molecule where valency allows;

Each $R_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, $R_7$, $R_9$, or phenyl having 1 substituent selected from $R_{20}$ and further having 0–3 substituents independently selected from F, Cl, Br, or I;

Each $R_{11}$ is independently H, alkyl, cycloalkyl, heterocycloalkyl, halogenated alkyl, halogenated cycloalkyl, or halogenated heterocycloalkyl;

$R_{13}$ is —$OR_{11}$, $SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$CF_3$, or —$NO_2$;

Each $R_{14}$ is independently H, alkyl, halogenated alkyl, limited substituted alkyl, cycloalkyl, halogenated cycloalkyl, substituted cycloalkyl, heterocycloalkyl, halogenated heterocycloalkyl, or substituted heterocycloalkyl;

$R_{15}$ is alkyl, substituted alkyl, halogenated alkyl, —$OR_{11}$, —CN, —$NO_2$, —$NR_{10}R_{10}$;

$R_{16}$ is —$OR_{17}$, —$NR_{17}R_{17}$, —$NR_{17}C(O)R_{17}$, —$NR_{17}S(O)_2R_{17}$, —$N(R_{17})C(O)NR_{17}R_{17}$, —$NR_{17}C(O)OR_{17}$;

$R_{17}$ is H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, phenyl, phenyl having 1–4 substituents independently selected from F, Cl, Br, I and $R_{15}$, naphthyl, or naphthyl having 1–4 substituents independently selected from F, Cl, Br, I and $R_{15}$;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, F, Cl, Br, or I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$NR_{11}R_{11}$, —$C(O)R_{11}$, —$C(O)NR_{11}R_{11}$, —CN, —$NR_{13}C(O)R_{11}$, —$S(O)_2NR_{11}R_{11}$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

or pharmaceutically acceptable salt, racemic mixture, or pure enantiomer thereof.

2. The compound of claim 1, wherein X is O.

3. The compound of claim 2, wherein $R_1$ is H, alkyl, or cycloalkyl.

4. The compound of claim 3, wherein W is (a).

5. The compound of claim 4, wherein (a) is thiophen-2-yl, furan-2-yl, 1,3-thiazol-5-yl, 1,3-oxazol-2-yl, 1,3-thiazol-2-yl or 1,3-oxazol-5-yl, any of which is optionally substituted on carbon independently with alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, limited substituted alkyl, limited substituted alkenyl, limited substituted alkynyl, aryl, —$OR_8$, —$OR_{14}$, —$SR_8$, —$SR_{14}$, F, Cl, Br, I, —$NR_8R_8$, —$NR_{14}R_{14}$, —$C(O)R_8$, —$C(O)R_{14}$, —$C(O)NR_8R_8$, —$C(O)NR_{14}R_{14}$, —$C(R_6)$=$N(R_{16})$, —CN, —$NR_8C(O)R_{11}$, —$S(O)_2NR_8R_8$, —$OS(O)_2R_{11}$, —$S(O)_2R_8$, —$S(O)_2R_{14}$, —$NR_8S(O)_2R_8$, —$N(H)C(O)N(H)R_8$, —$NO_2$, $R_7$, $R_9$, and 0–3 substituents independently selected from F, Cl, Br, I, or $R_{15}$, and 0–3 substituents independently selected from F, Cl, Br, I, or $R_{15}$; and further optionally substituted on nitrogen with alkyl, cycloalkyl, heterocycloalkyl, halogenated alkyl, halogenated cycloalkyl, halogenated heterocycloalkyl, substituted alkyl, limited substituted alkyl, substituted cycloalkyl, substituted heterocycloalkyl, aryl, or —$SO_2R_8$.

6. The compound according to claim 5, wherein (a) is thiophen-2-yl, furan-2-yl, 1,3-thiazol-2-yl, or 1,3-oxazol-2-yl, any of which is optionally substituted with up to 2 substituents wherein the substituents are bromo, chloro, methyl, phenyl, 2-fluorophenyl, 3-fluorophenyl, 4-fluorophenyl, 2-chlorophenyl, 3-chlorophenyl, 4-chlorophenyl, 2-methoxyphenyl, 3-methoxyphenyl, 4-methoxyphenyl, 2-methylphenyl, 3-methylphenyl, 4-methylphenyl, 2-hydroxyphenyl, 3-hydroxyphenyl, 4-hydroxyphenyl, 2-aminophenyl, 3-aminophenyl, 4-aminophenyl, 2-acetylaminophenyl, 3-acetylaminophenyl, 4-acetylaminophenyl, 2-trifluoroacetamidophenyl, 3-trifluoroacetamidophenyl, 4-trifluoroacetamidophenyl, or pyridinyl.

7. The compound of claim 6, wherein $R_1$ is H or lower alkyl.

8. The compound of claim 7, wherein Azabicyclo is II or V.

9. The compound of claim 8, wherein $R_2$ is lower alkyl or is absent provided that $k_2$ or $k_5$ is 0.

10. The compound of claim 9, wherein the compound is
N-[(3R,5R)-1-azabicyclo[3.2.1]oct-3-yl]-5-bromothiophene-2-carboxamide;
N-[(exo-4(S))-1-azabicyclo[2.2.1]hept-3-yl]-5-bromothiophene-2-carboxamide;
N-[(exo-4(S))-1-azabicyclo[2.2.1]hept-3-yl]-5-(pyridin-2-yl)-thiophene-2-carboxamide;
N-[(exo-4(S))-1-azabicyclo[2.2.1]hept-3-yl]-5-phenylthiophene-2-carboxamide;
N-[(3R,5R)-1-azabicyclo[3.2.1]oct-3-yl]-5-phenyl-2-furamide;
N-[(3R,5R)-1-azabicyclo[3.2.1]oct-3-yl]-5-(2-fluorophenyl)-2-furamide;
N-[(exo-4(S))-1-azabicyclo[2.2.1]hept-3-yl]-5-phenyl-2-furamide;
N-[(exo-4(S))-1-azabicyclo[2.2.1]hept-3-yl]-5-(2-fluorophenyl)-2-furamide;
N-[(exo-4(S))-1-azabicyclo[2.2.1]hept-3-yl]-5-(3-fluorophenyl)-2-furamide;
N-[(exo-4(S))-1-azabicyclo[2.2.1]hept-3-yl]-5-(4-fluorophenyl)-2-furamide;
N-[(exo-4(S))-1-azabicyclo[2.2.1]hept-3-yl]-5-(4-methylphenyl)-2-furamide;
N-[(3R,5R)-1-azabicyclo[3.2.1]oct-3-yl]-5-phenyl-1,3-oxazole-2-carboxamide;
5-(4-aminophenyl)-N-[(3R,5R)-1-azabicyclo[3.2.1]oct-3-yl]-1,3-oxazole-2-carboxamide;
5-(4-acetylaminophenyl)-N-[(3R,5R)-1-azabicyclo[3.2.1]oct-3-yl]-1,3-oxazole-2-carboxamide;
N-[(exo-4(S))-1-azabicyclo[2.2.1]hept-3-yl]-5-phenyl-1,3-oxazole-2-carboxamide; or a pharmaceutically acceptable salt thereof, provided that the compound is the pure enantiomer or racemic mixture thereof.

11. The compound of claim 9, wherein the compound is
N-[(3R,5R)-1-azabicyclo[3.2.1]oct-3-yl]-5-chlorothiophene-2-carboxamide;
N-[(3R,5R)-1-azabicyclo[3.2.1]oct-3-yl]-5-methylthiophene-2-carboxamide;
N-[(3R,5R)-1-azabicyclo[3.2.1]oct-3-yl]-5-phenylthiophene-2-carboxamide;
N-[(3R,5R)-1-azabicyclo[3.2.1]oct-3-yl]-5-(2-fluorophenyl)thiophene-2-carboxamide;
N-[(3R,5R)-1-azabicyclo[3.2.1]oct-3-yl]-5-(3-fluorophenyl)thiophene-2-carboxamide;
N-[(3R,5R)-1-azabicyclo[3.2.1]oct-3-yl]-5-(4-fluorophenyl)thiophene-2-carboxamide;
N-[(3R,5R)-1-azabicyclo[3.2.1]oct-3-yl]-5-(2-chlorophenyl)thiophene-2-carboxamide;
N-[(3R,5R)-1-azabicyclo[3.2.1]oct-3-yl]-5-(3-chlorophenyl)thiophene-2-carboxamide;
N-[(3R,5R)-1-azabicyclo[3.2.1]oct-3-yl]-5-(4-chlorophenyl)thiophene-2-carboxamide;
N-[(3R,5R)-1-azabicyclo[3.2.1]oct-3-yl]-5-(2-methoxyphenyl)thiophene-2-carboxamide;
N-[(3R,5R)-1-azabicyclo[3.2.1]oct-3-yl]-5-(3-methoxyphenyl)thiophene-2-carboxamide;
N-[(3R,5R)-1-azabicyclo[3.2.1]oct-3-yl]-5-(4-methoxyphenyl)thiophene-2-carboxamide;
N-[(3R,5R)-1-azabicyclo[3.2.1]oct-3-yl]-5-(2-methylphenyl)thiophene-2-carboxamide;
N-[(3R,5R)-1-azabicyclo[3.2.1]oct-3-yl]-5-(3-methylphenyl)thiophene-2-carboxamide;
N-[(3R,5R)-1-azabicyclo[3.2.1]oct-3-yl]-5-(4-methylphenyl)thiophene-2-carboxamide;
N-[(3R,5R)-1-azabicyclo[3.2.1]oct-3-yl]-5-(2-hydroxyphenyl)thiophene-2-carboxamide;
N-[(3R,5R)-1-azabicyclo[3.2.1]oct-3-yl]-5-(3-hydroxyphenyl)thiophene-2-carboxamide;
N-[(3R,5R)-1-azabicyclo[3.2.1]oct-3-yl]-5-(4-hydroxyphenyl)thiophene-2-carboxamide;
5-(2-aminophenyl)-N-[(3R,5R)-1-azabicyclo[3.2.1]oct-3-yl]thiophene-2-carboxamide;
5-(3-aminophenyl)-N-[(3R,5R)-1-azabicyclo[3.2.1]oct-3-yl]thiophene-2-carboxamide;
5-(4-aminophenyl)-N-[(3R,5R)-1-azabicyclo[3.2.1]oct-3-yl]thiophene-2-carboxamide;
5-(2-acetylaminophenyl)-N-[(3R,5R)-1-azabicyclo[3.2.1]oct-3-yl]thiophene-2-carboxamide;
5-(3-acetylaminophenyl)-N-[(3R,5R)-1-azabicyclo[3.2.1]oct-3-yl]thiophene-2-carboxamide;
5-(4-acetylaminophenyl)-N-[(3R,5R)-1-azabicyclo[3.2.1]oct-3-yl]thiophene-2-carboxamide;
N-[(3R,5R)-1-azabicyclo[3.2.1]oct-3-yl]-5-(2-trifluoroacetamidophenyl)thiophene-2-carboxamide;
N-[(3R,5R)-1-azabicyclo[3.2.1]oct-3-yl]-5-(3-trifluoroacetamidophenyl)thiophene-2-carboxamide;
N-[(3R,5R)-1-azabicyclo[3.2.1]oct-3-yl]-5-(4-trifluoroacetamidophenyl)thiophene-2-carboxamide;

or a pharmaceutically acceptable salt thereof, provided that the compound is the pure enantiomer or racemic mixture thereof.

12. The compound of claim 9, wherein the compound is
N-[(3R,5R)-1-azabicyclo[3.2.1]oct-3-yl]-5-bromo-2-furamide;
N-[(3R,5R)-1-azabicyclo[3.2.1]oct-3-yl]-5-chloro-2-furamide;
N-[(3R,5R)-1-azabicyclo[3.2.1]oct-3-yl]-5-methyl-2-furamide;
N-[(3R,5R)-1-azabicyclo[3.2.1]oct-3-yl]-5-(3-fluorophenyl)-2-furamide;
N-[(3R,5R)-1-azabicyclo[3.2.1]oct-3-yl]-5-(4-fluorophenyl)-2-furamide;
N-[(3R,5R)-1-azabicyclo[3.2.1]oct-3-yl]-5-(2-chlorophenyl)-2-furamide;
N-[(3R,5R)-1-azabicyclo[3.2.1]oct-3-yl]-5-(3-chlorophenyl)-2-furamide;
N-[(3R,5R)-1-azabicyclo[3.2.1]oct-3-yl]-5-(4-chlorophenyl)-2-furamide;
N-[(3R,5R)-1-azabicyclo[3.2.1]oct-3-yl]-5-(2-methoxyphenyl)-2-furamide;
N-[(3R,5R)-1-azabicyclo[3.2.1]oct-3-yl]-5-(3-methoxyphenyl)-2-furamide;
N-[(3R,5R)-1-azabicyclo[3.2.1]oct-3-yl]-5-(4-methoxyphenyl)-2-furamide;
N-[(3R,5R)-1-azabicyclo[3.2.1]oct-3-yl]-5-(2-methylphenyl)-2-furamide;
N-[(3R,5R)-1-azabicyclo[3.2.1]oct-3-yl]-5-(3-methylphenyl)-2-furamide;
N-[(3R,5R)-1-azabicyclo[3.2.1]oct-3-yl]-5-(4-methylphenyl)-2-furamide;
N-[(3R,5R)-1-azabicyclo[3.2.1]oct-3-yl]-5-(2-hydroxyphenyl)-2-furamide;
N-[(3R,5R)-1-azabicyclo[3.2.1]oct-3-yl]-5-(3-hydroxyphenyl)-2-furamide;
N-[(3R,5R)-1-azabicyclo[3.2.1]oct-3-yl]-5-(4-hydroxyphenyl)-2-furamide;
5-(2-aminophenyl)-N-[(3R,5R)-1-azabicyclo[3.2.1]oct-3-yl]-2-furamide;
5-(3-aminophenyl)-N-[(3R,5R)-1-azabicyclo[3.2.1]oct-3-yl]-2-furamide;
5-(4-aminophenyl)-N-[(3R,5R)-1-azabicyclo]3.2.1]oct-3-yl]-2-furamide;
5-(2-acetylaminophenyl)-N-[(3R,5R)-1-azabicyclo[3.2.1]oct-3-yl]-2-furamide;
5-(3-acetylaminophenyl)-N-[(3R,5R)-1-azabicyclo[3.2.1]oct-3-yl]-2-furamide;
5-(4-acetylaminophenyl)-N-[(3R,5R)-1-azabicyclo[3.2.1]oct-3-yl]-2-furamide;
N-[(3R,5R)-1-azabicyclo[3.2.1]oct-3-yl]-5-(2-trifluoroacetamidophenyl)-2-furamide;
N-[(3R,5R)-1-azabicyclo[3.2.1]oct-3-yl]-5-(3-trifluoroacetamidophenyl)-2-furamide;
N-[(3R,5R)-1-azabicyclo[3.2.1]oct-3-yl]-5-(4-trifluoroacetamidophenyl)-2-furamide; or a pharmaceutically acceptable salt thereof, provided that the compound is the pure enantiomer or racemic mixture thereof.

13. The compound of claim 9, wherein the compound is
N-[(3R,5R)-1-azabicyclo[3.2.1]oct-3-yl]-5-bromo-1,3-thiazole-2-carboxamide;
N-[(3R,5R)-1-azabicyclo[3.2.1]oct-3-yl]-5-chloro-1,3-thiazole-2-carboxamide;
N-[(3R,5R)-1-azabicyclo[3.2.1]oct-3-yl]-5-methyl-1,3-thiazole-2-carboxamide;
N-[(3R,5R)-1-azabicyclo[3.2.1]oct-3-yl]-5-phenyl-1,3-thiazole-2-carboxamide;
N-[(3R,5R)-1-azabicyclo[3.2.1]oct-3-yl]-5-(2-fluorophenyl)-1,3-thiazole-2-carboxamide;
N-[(3R,5R)-1-azabicyclo[3.2.1]oct-3-yl]-5-(3-fluorophenyl)-1,3-thiazole-2-carboxamide;
N-[(3R,5R)-1-azabicyclo[3.2.1]oct-3-yl]-5-(4-fluorophenyl)-1,3-thiazole-2-carboxamide
N-[(3R,5R)-1-azabicyclo[3.2.1]oct-3-yl]-5-(2-chlorophenyl)-1,3-thiazole-2-carboxamide
N-[(3R,5R)-1-azabicyclo[3.2.1]oct-3-yl]-5-(3-chlorophenyl)-1,3-thiazole-2-carboxamide
N-[(3R,5R)-1-azabicyclo[3.2.1]oct-3-yl]-5-(4-chlorophenyl)-1,3-thiazole-2-carboxamide;
N-[(3R,5R)-1-azabicyclo[3.2.1]oct-3-yl]-5-(2-methoxyphenyl)-1,3-thiazole-2-carboxamide;
N-[(3R,5R)-1-azabicyclo[3.2.1]oct-3-yl]-5-(3-methoxyphenyl)-1,3-thiazole-2-carboxamide;
N-[(3R,5R)-1-azabicyclo[3.2.1]oct-3-yl]-5-(4-methoxyphenyl)-1,3-thiazole-2-carboxamide;
N-[(3R,5R)-1-azabicyclo[3.2.1]oct-3-yl]-5-(2-methylphenyl)-1,3-thiazole-2-carboxamide;
N-[(3R,5R)-1-azabicyclo[3.2.1]oct-3-yl]-5-(3-methylphenyl)-1,3-thiazole-2-carboxamide;
N-[(3R,5R)-1-azabicyclo[3.2.1]oct-3-yl]-5-(4-methylphenyl)-1,3-thiazole-2-carboxamide;
N-[(3R,5R)-1-azabicyclo[3.2.1]oct-3-yl]-5-(2-hydroxyphenyl)-1,3-thiazole-2-carboxamide;
N-[(3R,5R)-1-azabicyclo[3.2.1]oct-3-yl]-5-(3-hydroxyphenyl)-1,3-thiazole-2-carboxamide;
N-[(3R,5R)-1-azabicyclo[3.2.1]oct-3-yl]-5-(4-hydroxyphenyl)-1,3-thiazole-2-carboxamide;
5-(2-aminophenyl)-N-[(3R,5R)-1-azabicyclo[3.2.1]oct-3-yl]-1,3-thiazole-2-carboxamide;
5-(3-aminophenyl)-N-[(3R,5R)-1-azabicyclo[3.2.1]oct-3-yl]-1,3-thiazole-2-carboxamide
5-(4-aminophenyl)-N-[(3R,5R)-1-azabicyclo[3.2.1]oct-3-yl]-1,3-thiazole-2-carboxamide;
5-(2-acetylaminophenyl)-N-[(3R,5R)-1-azabicyclo[3.2.1]oct-3-yl]-1,3-thiazole-2-carboxamide;
5-(3-acetylaminophenyl)-N-[(3R,5R)-1-azabicyclo[3.2.1]oct-3-yl]-1,3-thiazole-2-carboxamide;
5-(4-acetylaminophenyl)-N-[(3R,5R)-1-azabicyclo[3.2.1]oct-3-yl]-1,3-thiazole-2-carboxamide;
N-[(3R,5R)-1-azabicyclo[3.2.1]oct-3-yl]-5-(2-trifluoroacetamidophenyl)-1,3-thiazole-2-carboxamide;
N-[(3R,5R)-1-azabicyclo[3.2.1]oct-3-yl]-5-(3-trifluoroacetamidophenyl)-1,3-thiazole-2-carboxamide;
N-[(3R,5R)-1-azabicyclo[3.2.1]oct-3-yl]-5-(4-trifluoroacetamidophenyl)-1,3-thiazole-2-carboxamide; or a pharmaceutically acceptable salt thereof, provided that the compound is the pure enantiomer or racemic mixture thereof.

14. The compound of claim 9, wherein the compound is
N-[(3R,5R)-1-azabicyclo[3.2.1]oct-3-yl]-5-bromo-1,3-oxazole-2-carboxamide;

N-[(3R,5R)-1-azabicyclo[3.2.1]oct-3-yl]-5-chloro-1,3-oxazole-2-carboxamide;
N-[(3R,5R)-1-azabicyclo[3.2.1]oct-3-yl]-5-methyl-1,3-oxazole-2-carboxamide;
N-[(3R,5R)-1-azabicyclo[3.2.1]oct-3-yl]-5-(2-fluorophenyl)-1,3-oxazole-2-carboxamide;
N-[(3R,5R)-1-azabicyclo[3.2.1]oct-3-yl]-5-(3-fluorophenyl)-1,3-oxazole-2-carboxamide;
N-[(3R,5R)-1-azabicyclo[3.2.1]oct-3-yl]-5-(4-fluorophenyl)-1,3-oxazole-2-carboxamide;
N-[(3R,5R)-1-azabicyclo[3.2.1]oct-3-yl]-5-(2-chlorophenyl)-1,3-oxazole-2-carboxamide;
N-[(3R,5R)-1-azabicyclo[3.2.1]oct-3-yl]-5-(3-chlorophenyl)-1,3-oxazole-2-carboxamide;
N-[(3R,5R)-1-azabicyclo[3.2.1]oct-3-yl]-5-(4-chlorophenyl)-1,3-oxazole-2-carboxamide
N-[(3R,5R)-1-azabicyclo[3.2.1]oct-3-yl]-5-(2-methoxyphenyl)-1,3-oxazole-2-carboxamide;
N-[(3R,5R)-1-azabicyclo[3.2.1]oct-3-yl]-5-(3-methoxyphenyl)-1,3-oxazole-2-carboxamide
N-[(3R,5R)-1-azabicyclo[3.2.1]oct-3-yl]-5-(4-methoxyphenyl)-1,3-oxazole-2-carboxamide;
N-[(3R,5R)-1-azabicyclo[3.2.1]oct-3-yl]-5-(2-methylphenyl)-1,3-oxazole-2-carboxamide;
N-[(3R,5R)-1-azabicyclo[3.2.1]oct-3-yl]-5-(3-methylphenyl)-1,3-oxazole-2-carboxamide;
N-[(3R,5R)-1-azabicyclo[3.2.1]oct-3-yl]-5-(4-methylphenyl)-1,3-oxazole-2-carboxamide;
N-[(3R,5R)-1-azabicyclo[3.2.1]oct-3-yl]-5-(2-hydroxyphenyl)-1,3-oxazole-2-carboxamide;
N-[(3R,5R)-1-azabicyclo[3.2.1]oct-3-yl]-5-(3-hydroxyphenyl)-1,3-oxazole-2-carboxamide;
N-[(3R,5R)-1-azabicyclo[3.2.1]oct-3-yl]-5-(4-hydroxyphenyl)-1,3-oxazole-2-carboxamide;
5-(2-aminophenyl)-N-[(3R,5R)-1-azabicyclo[3.2.1]oct-3-yl]-1,3-oxazole-2-carboxamide;
5-(3-aminophenyl)-N-[(3R,5R)-1-azabicyclo[3.2.1]oct-3-yl]-1,3-oxazole-2-carboxamide;
5-(2-acetylaminophenyl)-N-[(3R,5R)-1-azabicyclo[3.2.1]oct-3-yl]-1,3-oxazole-2-carboxamide;
5-(3-acetylaminophenyl)-N-[(3R,5R)-1-azabicyclo[3.2.1]oct-3-yl]-1,3-oxazole-2-carboxamide;
N-[(3R,5R)-1-azabicyclo[3.2.1]oct-3-yl]-5-(2-trifluoroacetamidophenyl)-1,3-oxazole-2-carboxamide;
N-[(3R,5R)-1-azabicyclo[3.2.1]oct-3-yl]-5-(3-trifluoroacetamidophenyl)-1,3-oxazole-2-carboxamide;
N-[(3R,5R)-1-azabicyclo[3.2.1]oct-3-yl]-5-(4-trifluoroacetamidophenyl)-1,3-oxazole-2-carboxamide;
a pharmaceutically acceptable salt thereof, provided that the compound is the pure enantiomer or racemic mixture thereof.

15. The compound of claim 9, wherein the compound is
N-[(exo-4(S))-1-azabicyclo[2.2.1]hept-3-yl]-5-chlorothiophene-2-carboxamide;
N-[(exo-4(S))-1-azabicyclo[2.2.1]hept-3-yl]-5-methylthiophene-2-carboxamide;
N-[(exo-4(S))-1-azabicyclo[2.2.1]hept-3-yl]-5-(2-fluorophenyl)thiophene-2-carboxamide;
N-[(exo-4(S))-1-azabicyclo[2.2.1]hept-3-yl]-5-(3-fluorophenyl)thiophene-2-carboxamide;
N-[(exo-4(S))-1-azabicyclo[2.2.1]hept-3-yl]-5-(4-fluorophenyl)thiophene-2-carboxamide;
N-[(exo-4(S))-1-azabicyclo[2.2.1]hept-3-yl]-5-(2-chlorophenyl)thiophene-2-carboxamide;
N-[(exo-4(S))-1-azabicyclo[2.2.1]hept-3-yl]-5-(3-chlorophenyl)thiophene-2-carboxamide;
N-[(exo-4(S))-1-azabicyclo[2.2.1]hept-3-yl]-5-(4-chlorophenyl)thiophene-2-carboxamide;
N-[(exo-4(S))-1-azabicyclo[2.2.1]hept-3-yl]-5-(2-methoxyphenyl)thiophene-2-carboxamide;
N-[(exo-4(S))-1-azabicyclo[2.2.1]hept-3-yl]-5-(3-methoxyphenyl)thiophene-2-carboxamide;
N-[(exo-4(S))-1-azabicyclo[2.2.1]hept-3-yl]-5-(4-methoxyphenyl)thiophene-2-carboxamide;
N-[(exo-4(S))-1-azabicyclo[2.2.1]hept-3-yl]-5-(2-methylphenyl)thiophene-2-carboxamide;
N-[(exo-4(S))-1-azabicyclo[2.2.1]hept-3-yl]-5-(3-methylphenyl)thiophene-2-carboxamide;
N-[(exo-4(S))-1-azabicyclo[2.2.1]hept-3-yl]-5-(4-methylphenyl)thiophene-2-carboxamide;
N-[(exo-4(S))-1-azabicyclo[2.2.1]hept-3-yl]-5-(2-hydroxyphenyl)thiophene-2-carboxamide;
N-[(exo-4(S))-1-azabicyclo[2.2.1]hept-3-yl]-5-(3-hydroxyphenyl)thiophene-2-carboxamide;
N-[(exo-4(S))-1-azabicyclo[2.2.1]hept-3-yl]-5-(4-hydroxyphenyl)thiophene-2-carboxamide;
5-(2-aminophenyl)-N-[(exo-4(S))-1-azabicyclo[2.2.1]hept-3-yl]thiophene-2-carboxamide;
5-(3-aminophenyl)-N-[(exo-4(S))-1-azabicyclo[2.2.1]hept-3-yl]thiophene-2-carboxamide;
5-(4-aminophenyl)-N-[(exo-4(S))-1-azabicyclo[2.2.1]hept-3-yl]thiophene-2-carboxamide;
5-(2-acetylaminophenyl)-N-[(exo-4(S))-1-azabicyclo[2.2.1]hept-3-yl]thiophene-2-carboxamide;
5-(3-acetylaminophenyl)-N-[(exo-4(S))-1-azabicyclo[2.2.1]hept-3-yl]thiophene-2-carboxamide;
5-(4-acetylaminophenyl)-N-[(exo-4(S))-1-azabicyclo[2.2.1]hept-3-yl]thiophene-2-carboxamide;
N-[(exo-4(S))-1-azabicyclo[2.2.1]hept-3-yl]-5-(2-trifluoroacetamidophenyl)thiophene-2-carboxamide;
N-[(exo-4(S))-1-azabicyclo[2.2.1]hept-3-yl]-5-(3-trifluoroacetamidophenyl)thiophene-2-carboxamide;
N-[(exo-4(S))-1-azabicyclo[2.2.1]hept-3-yl]-5-(4-trifluoroacetamidophenyl)thiophene-2-carboxamide;
or a pharmaceutically acceptable salt thereof, provided that the compound is the pure enantiomer or racemic mixture thereof.

16. The compound of claim 9, wherein the compound is
N-[(exo-4(S))-1-azabicyclo[2.2.1]hept-3-yl]-5-bromo-2-furamide;
N-[(exo-4(S))-1-azabicyclo[2.2.1]hept-3-yl]-5-chloro-2-furamide;
N-[(exo-4(S))-1-azabicyclo[2.2.1]hept-3-yl]-5-methyl-2-furamide;
N-[(exo-4(S))-1-azabicyclo[2.2.1]hept-3-yl]-5-(2-chlorophenyl)-2-furamide;
N-[(exo-4(S))-1-azabicyclo[2.2.1]hept-3-yl]-5-(3-chlorophenyl)-2-furamide;
N-[(exo-4(S))-1-azabicyclo[2.2.1]hept-3-yl]-5-(4-chlorophenyl)-2-furamide;
N-[(exo-4(S))-1-azabicyclo[2.2.1]hept-3-yl]-5-(2-methoxyphenyl)-2-furamide;

N-[(exo-4(S))-1-azabicyclo[2.2.1]hept-3-yl]-5-(3-methoxyphenyl)-2-furamide;
N-[(exo-4(S))-1-azabicyclo[2.2.1]hept-3-yl]-5-(4-methoxyphenyl)-2-furamide;
N-[(exo-4(S))-1-azabicyclo[2.2.1]hept-3-yl]-5-(2-methylphenyl)-2-furamide;
N-[(exo-4(S))-1-azabicyclo[2.2.1]hept-3-yl]-5-(3-methylphenyl)-2-furamide;
N-[(exo-4(S))-1-azabicyclo[2.2.1]hept-3-yl]-5-(2-hydroxyphenyl)-2-furamide;
N-[(exo-4(S))-1-azabicyclo[2.2.1]hept-3-yl]-5-(3-hydroxyphenyl)-2-furamide;
N-[(exo-4(S))-1-azabicyclo[2.2.1]hept-3-yl]-5-(4-hydroxyphenyl)-2-furamide;
5-(2-aminophenyl)-N-[(exo-4(S))-1-azabicyclo[2.2.1]hept-3-yl]-2-furamide;
5-(3-aminophenyl)-N-[(exo-4(S))-1-azabicyclo[2.2.1]hept-3-yl]-2-furamide;
5-(4-aminophenyl)-N-[(exo-4(S))-1-azabicyclo[2.2.1]hept-3-yl]-2-furamide;
5-(2-acetylaminophenyl)-N-[(exo-4(S))-1-azabicyclo[2.2.1]hept-3-yl]-2-furamide;
5-(3-acetylaminophenyl)-N-[(exo-4(S))-1-azabicyclo[2.2.1]hept-3-yl]-2-furamide;
5-(4-acetylaminophenyl)-N-[(exo-4(S))-1-azabicyclo[2.2.1]hept-3-yl]-2-furamide;
N-[(exo-4(S))-1-azabicyclo[2.2.1]hept-3-yl]-5-(2-trifluoroacetamidophenyl)-2-furamide;
N-[(exo-4(S))-1-azabicyclo[2.2.1]hept-3-yl]-5-(3-trifluoroacetamidophenyl)-2-furamide;
N-[(exo-4(S))-1-azabicyclo[2.2.1]hept-3-yl]-5-(4-trifluoroacetamidophenyl)-2-furamide; or a pharmaceutically acceptable salt thereof, provided that the compound is the pure enantiomer or racemic mixture thereof.

17. The compound of claim 9, wherein the compound is
N-[(exo-4(S))-1-azabicyclo[2.2.1]hept-3-yl]-5-bromo-1,3-thiazole-2-carboxamide;
N-[(exo-4(S))-1-azabicyclo[2.2.1]hept-3-yl]-5-chloro-1,3-thiazole-2-carboxamide;
N-[(exo-4(S))-1-azabicyclo[2.2.1]hept-3-yl]-5-methyl-1,3-thiazole-2-carboxamide;
N-[(exo-4(S))-1-azabicyclo[2.2.1]hept-3-yl]-5-phenyl-1,3-thiazole-2-carboxamide;
N-[(exo-4(S))-1-azabicyclo[2.2.1]hept-3-yl]-5-(2-fluorophenyl)-1,3-thiazole-2-carboxamide;
N-[(exo-4(S))-1-azabicyclo[2.2.1]hept-3-yl]-5-(3-fluorophenyl)-1,3-thiazole-2-carboxamide;
N-[(exo-4(S))-1-azabicyclo[2.2.1]hept-3-yl]-5-(4-fluorophenyl)-1,3-thiazole-2-carboxamide;
N-[(exo-4(S))-1-azabicyclo[2.2.1]hept-3-yl]-5-(2-chlorophenyl)-1,3-thiazole-2-carboxamide;
N-[(exo-4(S))-1-azabicyclo[2.2.1]hept-3-yl]-5-(3-chlorophenyl)-1,3-thiazole-2-carboxamide;
N-[(exo-4(S))-1-azabicyclo[2.2.1]hept-3-yl]-5-(4-chlorophenyl)-1,3-thiazole-2-carboxamide;
N-[(exo-4(S))-1-azabicyclo[2.2.1]hept-3-yl]-5-(2-methoxyphenyl)-1,3-thiazole-2-carboxamide;
N-[(exo-4(S))-1-azabicyclo[2.2.1]hept-3-yl]-5-(3-methoxyphenyl)-1,3-thiazole-2-carboxamide;
N-[(exo-4(S))-1-azabicyclo[2.2.1]hept-3-yl]-5-(4-methoxyphenyl)-1,3-thiazole-2-carboxamide;
N-[(exo-4(S))-1-azabicyclo[2.2.1]hept-3-yl]-5-(2-methylphenyl)-1,3-thiazole-2-carboxamide;
N-[(exo-4(S))-1-azabicyclo[2.2.1]hept-3-yl]-5-(3-methylphenyl)-1,3-thiazole-2-carboxamide;
N-[(exo-4(S))-1-azabicyclo[2.2.1]hept-3-yl]-5-(4-methylphenyl)-1,3-thiazole-2-carboxamide;
N-[(exo-4(S))-1-azabicyclo[2.2.1]hept-3-yl]-5-(2-hydroxyphenyl)-1,3-thiazole-2-carboxamide;
N-[(exo-4(S))-1-azabicyclo[2.2.1]hept-3-yl]-5-(3-hydroxyphenyl)-1,3-thiazole-2-carboxamide;
N-[(exo-4(S))-1-azabicyclo[2.2.1]hept-3-yl]-5-(4-hydroxyphenyl)-1,3-thiazole-2-carboxamide;
5-(2-aminophenyl)-N-[(exo-4(S))-1-azabicyclo[2.2.1]hept-3-yl]-1,3-thiazole-2-carboxamide;
5-(3-aminophenyl)-N-[(exo-4(S))-1-azabicyclo[2.2.1]hept-3-yl]-1,3-thiazole-2-carboxamide;
5-(4-aminophenyl)-N-[(exo-4(S))-1-azabicyclo[2.2.1]hept-3-yl]-1,3-thiazole-2-carboxamide;
5-(2-acetylaminophenyl)-N-[(exo-4(S))-1-azabicyclo[2.2.1]hept-3-yl]-1,3-thiazole-2-carboxamide;
5-(3-acetylaminophenyl)-N-[(exo-4(S))-1-azabicyclo[2.2.1]hept-3-yl]-1,3-thiazole-2-carboxamide;
5-(4-acetylaminophenyl)-N-[(exo-4(S))-1-azabicyclo[2.2.1]hept-3-yl]-1,3-thiazole-2-carboxamide;
N-[(exo-4(S))-1-azabicyclo[2.2.1]hept-3-yl]-5-(2-trifluoroacetamidophenyl)-1,3-thiazole-2-carboxamide;
N-[(exo-4(S))-1-azabicyclo[2.2.1]hept-3-yl]-5-(3-trifluoroacetamidophenyl)-1,3-thiazole-2-carboxamide;
N-[(exo-4(S))-1-azabicyclo[2.2.1]hept-3-yl]-5-(4-trifluoroacetamidophenyl)-1,3-thiazole-2-carboxamide; or a pharmaceutically acceptable salt thereof, provided that the compound is the pure enantiomer or racemic mixture thereof.

18. The compound of claim 9, wherein the compound is
N-[(exo-4(S))-1-azabicyclo[2.2.1]hept-3-yl]-5-bromo-1,3-oxazole-2-carboxamide;
N-[(exo-4(S))-1-azabicyclo[2.2.1]hept-3-yl]-5-chloro-1,3-oxazole-2-carboxamide;
N-[(exo-4(S))-1-azabicyclo[2.2.1]hept-3-yl]-5-methyl-1,3-oxazole-2-carboxamide;
N-[(exo-4(S))-1-azabicyclo[2.2.1]hept-3-yl]-5-(2-fluorophenyl)-1,3-oxazole-2-carboxamide;
N-[(exo-4(S))-1-azabicyclo[2.2.1]hept-3-yl]-5-(3-fluorophenyl)-1,3-oxazole-2-carboxamide;
N-[(exo-4(S))-1-azabicyclo[2.2.1]hept-3-yl]-5-(4-fluorophenyl)-1,3-oxazole-2-carboxamide;
N-[(exo-4(S))-1-azabicyclo[2.2.1]hept-3-yl]-5-(2-chlorophenyl)-1,3-oxazole-2-carboxamide;
N-[(exo-4(S))-1-azabicyclo[2.2.1]hept-3-yl]-5-(3-chlorophenyl)-1,3-oxazole-2-carboxamide;
N-[(exo-4(S))-1-azabicyclo[2.2.1]hept-3-yl]-5-(4-chlorophenyl)-1,3-oxazole-2-carboxamide;
N-[(exo-4(S))-1-azabicyclo[2.2.1]hept-3-yl]-5-(2-methoxyphenyl)-1,3-oxazole-2-carboxamide;
N-[(exo-4(S))-1-azabicyclo[2.2.1]hept-3-yl]-5-(3-methoxyphenyl)-1,3-oxazole-2-carboxamide;
N-[(exo-4(S))-1-azabicyclo[2.2.1]hept-3-yl]-5-(4-methoxyphenyl)-1,3-oxazole-2-carboxamide;
N-[(exo-4(S))-1-azabicyclo[2.2.1]hept-3-yl]-5-(2-methylphenyl)-1,3-oxazole-2-carboxamide;

N-[(exo-4(S))-1-azabicyclo[2.2.1]hept-3-yl]-5-(3-methylphenyl)-1,3-oxazole-2-carboxamide;
N-[(exo-4(S))-1-azabicyclo[2.2.1]hept-3-yl]-5-(4-methylphenyl)-1,3-oxazole-2-carboxamide;
N-[(exo-4(S))-1-azabicyclo[2.2.1]hept-3-yl]-5-(2-hydroxyphenyl)-1,3-oxazole-2-carboxamide;
N-[(exo-4(S))-1-azabicyclo[2.2.1]hept-3-yl]-5-(3-hydroxyphenyl)-1,3-oxazole-2-carboxamide;
N-[(exo-4(S))-1-azabicyclo[2.2.1]hept-3-yl]-5-(4-hydroxyphenyl)-1,3-oxazole-2-carboxamide;
5-(2-aminophenyl)-N-[(exo-4(S))-1-azabicyclo[2.2.1]hept-3-yl]-1,3-oxazole-2-carboxamide;
5-(3-aminophenyl)-N-[(exo-4(S))-1-azabicyclo[2.2.1]hept-3-yl]-1,3-oxazole-2-carboxamide;
5-(4-aminophenyl)-N-[(exo-4(S))-1-azabicyclo[2.2.1]hept-3-yl]-1,3-oxazole-2-carboxamide;
5-(2-acetylaminophenyl)-N-[(exo-4(S))-1-azabicyclo[2.2.1]hept-3-yl]-1,3-oxazole-2-carboxamide;
5-(3-acetylaminophenyl)-N-[(exo-4(S))-1-azabicyclo[2.2.1]hept-3-yl]-1,3-oxazole-2-carboxamide;
5-(4-acetylaminophenyl)-N-[(exo-4(S))-1-azabicyclo[2.2.1]hept-3-yl]-1,3-oxazole-2-carboxamide;
N-[(exo-4(S))-1-azabicyclo[2.2.1]hept-3-yl]-5-(2-trifluoroacetamidophenyl)-1,3-oxazole-2-carboxamide;
N-[(exo-4(S))-1-azabicyclo[2.2.1]hept-3-yl]-5-(3-trifluoroacetamidophenyl)-1,3-oxazole-2-carboxamide;
N-[(exo-4(S))-1-azabicyclo[2.2.1]hept-3-yl[-5-(4-trifluoroacetamidophenyl)-1,3-oxazole-2-carboxamide;
or a pharmaceutically acceptable salt thereof, provided that the compound is the pure enantiomer or racemic mixture thereof.

19. The compound of claim 7, wherein Azabicyclo is I, III, IV, or V.

20. The compound of claim 19, wherein $R_{23}$ is H or lower alkyl and wherein $R_2$ is lower alkyl or $R_2$ is absent provided that $k_6$ is 0.

21. The compound of claim 20, wherein the compound is
N-[(3R)-6-methyl-1-azabicyclo[2.2.2]oct-3-yl]-5-bromothiophene-2-carboxamide;
N-[(3R)-6-methyl-1-azabicyclo[2.2.2]oct-3-yl]-5-chlorothiophene-2-carboxamide;
N-[(3R)-6-methyl-1-azabicyclo[2.2.2]oct-3-yl]-5-methylthiophene-2-carboxamide;
N-[(3R)-6-methyl-1-azabicyclo[2.2.2]oct-3-yl]-5-phenylthiophene-2-carboxamide;
N-[(3R)-6-methyl-1-azabicyclo[2.2.2]oct-3-yl]-5-(2-fluorophenyl)thiophene-2-carboxamide;
N-[(3R)-6-methyl-1-azabicyclo[2.2.2]oct-3-yl]-5-(3-fluorophenyl)thiophene-2-carboxamide;
N-[(3R)-6-methyl-1-azabicyclo[2.2.2]oct-3-yl]-5-(4-fluorophenyl)thiophene-2-carboxamide;
N-[(3R)-6-methyl-1-azabicyclo[2.2.2]oct-3-yl]-5-(2-chlorophenyl)thiophene-2-carboxamide;
N-[(3R)-6-methyl-1-azabicyclo[2.2.2]oct-3-yl]-5-(3-chlorophenyl)thiophene-2carboxamide;
N-[(3R)-6-methyl-1-azabicyclo[2.2.2]oct-3-yl]-5-(4-chlorophenyl)thiophene-2-carboxamide;
N-[(3R)-6-methyl-1-azabicyclo[2.2.2]oct-3-yl]-5-(2-methoxyphenyl)thiophene-2-carboxamide;
N-[(3R)-6-methyl-1-azabicyclo[2.2.2]oct-3-yl]-5-(3-methoxyphenyl)thiophene-2-carboxamide;
N-[(3R)-6-methyl-1-azabicyclo[2.2.2]oct-3-yl]-5-(4-methoxyphenyl)thiophene-2-carboxamide;
N-[(3R)-6-methyl-1-azabicyclo[2.2.2]oct-3-yl]-5-(2-methylphenyl)thiophene-2-carboxamide;
N-[(3R)-6-methyl-1-azabicyclo[2.2.2]oct-3-yl]-5-(3-methylphenyl)thiophene-2-carboxamide;
N-[(3R)-6-methyl-1-azabicyclo[2.2.2]oct-3-yl]-5-(4-methylphenyl)thiophene-2-carboxamide;
N-[(3R)-6-methyl-1-azabicyclo[2.2.2]oct-3-yl]-5-(2-hydroxyphenyl)thiophene-2-carboxamide;
N-[(3R)-6-methyl-1-azabicyclo[2.2.2]oct-3-yl]-5-(3-hydroxyphenyl)thiophene-2-carboxamide;
N-[(3R)-6-methyl-1-azabicyclo[2.2.2]oct-3-yl]-5-(4-hydroxyphenyl)thiophene-2-carboxamide;
5-(2-aminophenyl)-N-[(3R)-6-methyl-1-azabicyclo[2.2.2]oct-3-yl]thiophene-2-carboxamide;
5-(3-aminophenyl)-N-[(3R)-6-methyl-1-azabicyclo[2.2.2]oct-3-yl]thiophene-2-carboxamide;
5-(4-aminophenyl)-N-[(3R)-6-methyl-1-azabicyclo[2.2.2]oct-3-yl]thiophene-2-carboxamide;
5-(2-acetylaminophenyl)-N-[(3R)-6-methyl-1-azabicyclo[2.2.2]oct-3-yl]thiophene-2-carboxamide;
5-(3-acetylaminophenyl)-N-[(3R)-6-methyl-1-azabicyclo[2.2.2]oct-3-yl]thiophene-2-carboxamide;
5-(4-acetylaminophenyl)-N-[(3R)-6-methyl-1-azabicyclo[2.2.2]oct-3-yl]thiophene-2-carboxamide;
N-[(3R)-6-methyl-1-azabicyclo[2.2.2]oct-3-yl]-5-(2-trifluoroacetamidophenyl)thiophene-2-carboxamide;
N-[(3R)-6-methyl-1-azabicyclo[2.2.2]oct-3-yl]-5-(3-trifluoroacetamidophenyl)thiophene-2-carboxamide;
N-[(3R)-6-methyl-1-azabicyclo[2.2.2]oct-3-yl]-5-(4-trifluoroacetamidophenyl)thiophene-2-carboxamide;
N-[(3R)-6-methyl-1-azabicyclo[2.2.2]oct-3-yl]-5-bromo-2-furamide;
N-[(3R)-6-methyl-1-azabicyclo[2.2.2]oct-3-yl]-5-chloro-2-furamide;
N-[(3R)-6-methyl-1-azabicyclo[2.2.2]oct-3-yl]-5-methyl-2-furamide;
N-[(3R)-6-methyl-1-azabicyclo[2.2.2]oct-3-yl]-5-phenyl-2-furamide;
N-[(3R)-6-methyl-1-azabicyclo[2.2.2]oct-3-yl]-5-(2-fluorophenyl)-2-furamide;
N-[(3R)-6-methyl-1-azabicyclo[2.2.2]oct-3-yl]-5-(3-fluorophenyl)-2-furamide;
N-[(3R)-6-methyl-1-azabicyclo[2.2.2]oct-3-yl]-5-(4-fluorophenyl)-2-furamide;
N-[(3R)-6-methyl-1-azabicyclo[2.2.2]oct-3-yl]-5-(2-chlorophenyl)-2-furamide;
N-[(3R)-6-methyl-1-azabicyclo[2.2.2]oct-3-yl]-5-(3-chlorophenyl)-2-furamide;
N-[(3R)-6-methyl-1-azabicyclo[2.2.2]oct-3-yl]-5-(4-chlorophenyl)-2-furamide;
N-[(3R)-6-methyl-1-azabicyclo[2.2.2]oct-3-yl]-5-(2-methoxyphenyl)-2-furamide;
N-[(3R)-6-methyl-1-azabicyclo[2.2.2]oct-3-yl]-5-(3-methoxyphenyl)-2-furamide;
N-[(3R)-6-methyl-1-azabicyclo[2.2.2]oct-3-yl]-5-(4-methoxyphenyl)-2-furamide;
N-[(3R)-6-methyl-1-azabicyclo[2.2.2]oct-3-yl]-5-(2-methylphenyl)-2-furamide;

N-[(3R)-6-methyl-1-azabicyclo[2.2.2]oct-3-yl]-5-(3-methylphenyl)-2-furamide;
N-[(3R)-6-methyl-1-azabicyclo[2.2.2]oct-3-yl]-5-(4-methylphenyl)-2-furamide;
N-[(3R)-6-methyl-1-azabicyclo[2.2.2]oct-3-yl]-5-(2-hydroxyphenyl)-2-furamide;
N-[(3R)-6-methyl-1-azabicyclo[2.2.2]oct-3-yl]-5-(3-hydroxyphenyl)-2-furamide;
N-[(3R)-6-methyl-1-azabicyclo[2.2.2]oct-3-yl]-5-(4-hydroxyphenyl)-2-furamide;
5-(2-aminophenyl)-N-[(3R)-6-methyl-1-azabicyclo[2.2.2]oct-3-yl]-2-furamide;
5-(3-aminophenyl)-N-[(3R)-6-methyl-1-azabicyclo[2.2.2]oct-3-yl]-2-furamide;
5-(4-aminophenyl)-N-[(3R)-6-methyl-1-azabicyclo[2.2.2]oct-3-yl]-2-furamide;
5-(2-acetylaminophenyl)-N-[(3R)-6-methyl-1-azabicyclo[2.2.2]oct-3-yl]-2-furamide;
5-(3-acetylaminophenyl)-N-[(3R)-6-methyl-1-azabicyclo[2.2.2]oct-3-yl]-2-furamide;
5-(4-acetylaminophenyl)-N-[(3R)-6-methyl-1-azabicyclo[2.2.2]oct-3-yl]-2-furamide;
N-[(3R)-6-methyl-1-azabicyclo[2.2.2]oct-3-yl]-5-(2-trifluoroacetamidophenyl)-2-furamide;
N-[(3R)-6-methyl-1-azabicyclo[2.2.2]oct-3-yl]-5-(3-trifluoroacetamidophenyl)-2-furamide;
N-[(3R)-6-methyl-1-azabicyclo[2.2.2]oct-3-yl]-5-(4-trifluoroacetamidophenyl)-2-furamide;
N-[(3R)-6-methyl-1-azabicyclo[2.2.2]oct-3-yl]-5-bromo-1,3-thiazole-2-carboxamide;
N-[(3R)-6-methyl-1-azabicyclo[2.2.2]oct-3-yl]-5-chloro-1,3-thiazole-2-carboxamide;
N-[(3R)-6-methyl-1-azabicyclo[2.2.2]oct-3-yl]-5-methyl-1,3-thiazole-2-carboxamide;
N-[(3R)-6-methyl-1-azabicyclo[2.2.2]oct-3-yl]-5-phenyl-1,3-thiazole-2-carboxamide;
N-[(3R)-6-methyl-1-azabicyclo[2.2.2]oct-3-yl]-5-(2-fluorophenyl)-1,3-thiazole-2-carboxamide;
N-[(3R)-6-methyl-1-azabicyclo[2.2.2]oct-3-yl]-5-(3-fluorophenyl)-1,3-thiazole-2-carboxamide;
N-[(3R)-6-methyl-1-azabicyclo[2.2.2]oct-3-yl]-5-(4-fluorophenyl)-1,3-thiazole-2-carboxamide;
N-[(3R)-6-methyl-1-azabicyclo[2.2.2]oct-3-yl]-5-(2-chlorophenyl)-1,3-thiazole-2-carboxamide;
N-[(3R)-6-methyl-1-azabicyclo[2.2.2]oct-3-yl]-5-(3-chlorophenyl)-1,3-thiazole-2-carboxamide;
N-[(3R)-6-methyl-1-azabicyclo[2.2.2]oct-3-yl]-5-(4-chlorophenyl)-1,3-thiazole-2-carboxamide;
N-[(3R)-6-methyl-1-azabicyclo[2.2.2]oct-3-yl]-5-(2-methoxyphenyl)-1,3-thiazole-2-carboxamide;
N-[(3R)-6-methyl-1-azabicyclo[2.2.2]oct-3-yl]-5-(3-methoxyphenyl)-1,3-thiazole-2-carboxamide;
N-[(3R)-6-methyl-1-azabicyclo[2.2.2]oct-3-yl]-5-(4-methoxyphenyl)-1,3-thiazole-2-carboxamide;
N-[(3R)-6-methyl-1-azabicyclo[2.2.2]oct-3-yl]-5-(2-methylphenyl)-1,3-thiazole-2-carboxamide;
N-[(3R)-6-methyl-1-azabicyclo[2.2.2]oct-3-yl]-5-(3-methylphenyl)-1,3-thiazole-2-carboxamide;
N-[(3R)-6-methyl-1-azabicyclo[2.2.2]oct-3-yl]-5-(4-methylphenyl)-1,3-thiazole-2-carboxamide;
N-[(3R)-6-methyl-1-azabicyclo[2.2.2]oct-3-yl]-5-(2-hydroxyphenyl)-1,3-thiazole-2-carboxamide;
N-[(3R)-6-methyl-1-azabicyclo[2.2.2]oct-3-yl]-5-(3-hydroxyphenyl)-1,3-thiazole-2-carboxamide;
N-[(3R)-6-methyl-1-azabicyclo[2.2.2]oct-3-yl]-5-(4-hydroxyphenyl)-1,3-thiazole-2-carboxamide;
5-(2-aminophenyl)-N-[(3R)-6-methyl-1-azabicyclo[2.2.2]oct-3-yl]-1,3-thiazole-2-carboxamide;
5-(3-aminophenyl)-N-[(3R)-6-methyl-1-azabicyclo[2.2.2]oct-3-yl]-1,3-thiazole-2-carboxamide;
5-(4-aminophenyl)-N-[(3R)-6-methyl-1-azabicyclo[2.2.2]oct-3-yl]-1,3-thiazole-2-carboxamide;
5-(2-acetylaminophenyl)-N-[(3R)-6-methyl-1-azabicyclo[2.2.2]oct-3-yl]-1,3-thiazole-2-carboxamide;
5-(3-acetylaminophenyl)-N-[(3R)-6-methyl-1-azabicyclo[2.2.2]oct-3-yl]-1,3-thiazole-2-carboxamide;
5-(4-acetylaminophenyl)-N-[(3R)-6-methyl-1-azabicyclo[2.2.2]oct-3-yl]-1,3-thiazole-2-carboxamide;
N-[(3R)-6-methyl-1-azabicyclo[2.2.2]oct-3-yl]-5-(2-trifluoroacetamidophenyl)-1,3-thiazole-2-carboxamide;
N-[(3R)-6-methyl-1-azabicyclo[2.2.2]oct-3-yl]-5-(3-trifluoroacetamidophenyl)-1,3-thiazole-2-carboxamide;
N-[(3R)-6-methyl-1-azabicyclo[2.2.2]oct-3-yl]-5-(4-trifluoroacetamidophenyl)-1,3-thiazole-2-carboxamide;
N-[(3R)-6-methyl-1-azabicyclo[2.2.2]oct-3-yl]-5-bromo-1,3-oxazole-2-carboxamide;
N-[(3R)-6-methyl-1-azabicyclo[2.2.2]oct-3-yl]-5-chloro-1,3-oxazole-2-carboxamide;
N-[(3R)-6-methyl-1-azabicyclo[2.2.2]oct-3-yl]-5-methyl-1,3-oxazole-2-carboxamide;
N-[(3R)-6-methyl-1-azabicyclo[2.2.2]oct-3-yl]-5-phenyl-1,3-oxazole-2-carboxamide;
N-[(3R)-6-methyl-1-azabicyclo[2.2.2]oct-3-yl]-5-(2-fluorophenyl)-1,3-oxazole-2-carboxamide;
N-[(3R)-6-methyl-1-azabicyclo[2.2.2]oct-3-yl]-5-(3-fluorophenyl)-1,3-oxazole-2-carboxamide;
N-[(3R)-6-methyl-1-azabicyclo[2.2.2]oct-3-yl]-5-(4-fluorophenyl)-1,3-oxazole-2-carboxamide;
N-[(3R)-6-methyl-1-azabicyclo[2.2.2]oct-3-yl]-5-(2-chlorophenyl)-1,3-oxazole-2-carboxamide;
N-[(3R)-6-methyl-1-azabicyclo[2.2.2]oct-3-yl]-5-(3-chlorophenyl)-1,3-oxazole-2-carboxamide;
N-[(3R)-6-methyl-1-azabicyclo[2.2.2]oct-3-yl]-5-(4-chlorophenyl)-1,3-oxazole-2-carboxamide;
N-[(3R)-6-methyl-1-azabicyclo[2.2.2]oct-3-yl]-5-(2-methoxyphenyl)-1,3-oxazole-2-carboxamide;
N-[(3R)-6-methyl-1-azabicyclo[2.2.2]oct-3-yl]-5-(3-methoxyphenyl)-1,3-oxazole-2-carboxamide;
N-[(3R)-6-methyl-1-azabicyclo[2.2.2]oct-3-yl]-5-(4-methoxyphenyl)-1,3-oxazole-2-carboxamide;
N-[(3R)-6-methyl-1-azabicyclo[2.2.2]oct-3-yl]-5-(2-methylphenyl)-1,3-oxazole-2-carboxamide;
N-[(3R)-6-methyl-1-azabicyclo[2.2.2]oct-3-yl]-5-(3-methylphenyl)-1,3-oxazole-2-carboxamide;
N-[(3R)-6-methyl-1-azabicyclo[2.2.2]oct-3-yl]-5-(4-methylphenyl)-1,3-oxazole-2-carboxamide;
N-[(3R)-6-methyl-1-azabicyclo[2.2.2]oct-3-yl]-5-(2-hydroxyphenyl)-1,3-oxazole-2-carboxamide;
N-[(3R)-6-methyl-1-azabicyclo[2.2.2]oct-3-yl]-5-(3-hydroxyphenyl)-1,3-oxazole-2-carboxamide;
N-[(3R)-6-methyl-1-azabicyclo[2.2.2]oct-3-yl]-5-(4-hydroxyphenyl)-1,3-oxazole-2-carboxamide;

5-(2-aminophenyl)-N-[(3R)-6-methyl-1-azabicyclo[2.2.2]oct-3-yl]-1,3-oxazole-2-carboxamide;
5-(3-aminophenyl)-N-[(3R)-6-methyl-1-azabicyclo[2.2.2]oct-3-yl]-1,3-oxazole-2-carboxamide;
5-(4-aminophenyl)-N-[(3R)-6-methyl-1-azabicyclo[2.2.2]oct-3-yl]-1,3-oxazole-2-carboxamide;
5-(2-acetylaminophenyl)-N-[(3R)-6-methyl-1-azabicyclo[2.2.2]oct-3-yl]-1,3-oxazole-2-carboxamide;
5-(3-acetylaminophenyl)-N-[(3R)-6-methyl-1-azabicyclo[2.2.2]oct-3-yl]-1,3-oxazole-2-carboxamide;
5-(4-acetylaminophenyl)-N-[(3R)-6-methyl-1-azabicyclo[2.2.2]oct-3-yl]-1,3-oxazole-2-carboxamide;
N-[(3R)-6-methyl-1-azabicyclo[2.2.2]oct-3-yl]-5-(2-trifluoroacetamidophenyl)-1,3-oxazole-2-carboxamide;
N-[(3R)-6-methyl-1-azabicyclo[2.2.2]oct-3-yl]-5-(3-trifluoroacetamidophenyl)-1,3-oxazole-2-carboxamide;
N-[(3R)-6-methyl-1-azabicyclo[2.2.2]oct-3-yl]-5-(4-trifluoroacetamidophenyl)-1,3-oxazole-2-carboxamide;
N-[(3R)-1-azabicyclo[3.2.2]non-3-yl]-5-phenyl-1,3-oxazole-2-carboxamide; or a pharmaceutically acceptable salt thereof, provided that the compound is the pure enantiomer or racemic mixture thereof.

22. The compound of claim 20, wherein the compound is
N-[2-azabicyclo[2.2.1]hept-5-yl]-5-bromothiophene-2-carboxamide;
N-[2-azabicyclo[2.2.1]hept-5-yl]-5-chlorothiophene-2-carboxamide;
N-[2-azabicyclo[2.2.1]hept-5-yl]-5-methylthiophene-2-carboxamide;
N-[2-azabicyclo[2.2.1]hept-5-yl]-5-phenylthiophene-2-carboxamide;
N-[2-azabicyclo[2.2.1]hept-5-yl]-5-(2-fluorophenyl)thiophene-2-carboxamide;
N-[2-azabicyclo[2.2.1]hept-5-yl]-5-(3-fluorophenyl)thiophene-2-carboxamide;
N-[2-azabicyclo[2.2.1]hept-5-yl]-5-(4-fluorophenyl)thiophene-2-carboxamide;
N-[2-azabicyclo[2.2.1]hept-5-yl]-5-(2-chlorophenyl)thiophene-2-carboxamide;
N-[2-azabicyclo[2.2.1]hept-5-yl]-5-(3-chlorophenyl)thiophene-2-carboxamide;
N-[2-azabicyclo[2.2.1]hept-5-yl]-5-(4-chlorophenyl)thiophene-2-carboxamide;
N-[2-azabicyclo[2.2.1]hept-5-yl]-5-(2-methoxyphenyl)thiophene-2-carboxamide;
N-[2-azabicyclo[2.2.1]hept-5-yl]-5-(3-methoxyphenyl)thiophene-2-carboxamide;
N-[2-azabicyclo[2.2.1]hept-5-yl]-5-(4-methoxyphenyl)thiophene-2-carboxamide;
N-[2-azabicyclo[2.2.1]hept-5-yl]-5-(2-methylphenyl)thiophene-2-carboxamide;
N-[2-azabicyclo[2.2.1]hept-5-yl]-5-(3-methylphenyl)thiophene-2-carboxamide;
N-[2-azabicyclo[2.2.1]hept-5-yl]-5-(4-methylphenyl)thiophene-2-carboxamide;
N-[2-azabicyclo[2.2.1]hept-5-yl]-5-(2-hydroxyphenyl)thiophene-2-carboxamide;
N-[2-azabicyclo[2.2.1]hept-5-yl]-5-(3-hydroxyphenyl)thiophene-2-carboxamide;
N-[2-azabicyclo[2.2.1]hept-5-yl]-5-(4-hydroxyphenyl)thiophene-2-carboxamide;
5-(2-aminophenyl)-N-[2-azabicyclo[2.2.1]hept-5-yl]thiophene-2-carboxamide;
5-(3-aminophenyl)-N-[2-azabicyclo[2.2.1]hept-5-yl]thiophene-2-carboxamide;
5-(4-aminophenyl)-N-[2-azabicyclo[2.2.1]hept-5-yl]thiophene-2-carboxamide;
5-(2-acetylaminophenyl)-N-[2-azabicyclo[2.2.1]hept-5-yl]thiophene-2-carboxamide;
5-(3-acetylaminophenyl)-N-[2-azabicyclo[2.2.1]hept-5-yl]thiophene-2-carboxamide;
5-(4-acetylaminophenyl)-N-[2-azabicyclo[2.2.1]hept-5-yl]thiophene-2-carboxamide;
N-[2-azabicyclo[2.2.1]hept-5-yl]-5-(2-trifluoroacetamidophenyl)thiophene-2-carboxamide;
N-[2-azabicyclo[2.2.1]hept-5-yl]-5-(3-trifluoroacetamidophenyl)thiophene-2-carboxamide;
N-[2-azabicyclo[2.2.1]hept-5-yl]-5-(4-trifluoroacetamidophenyl)thiophene-2-carboxamide;
N-[2-azabicyclo[2.2.1]hept-5-yl]-5-bromo-2-furamide;
N-[2-azabicyclo[2.2.1]hept-5-yl]-5-chloro-2-furamide;
N-[2-azabicyclo[2.2.1]hept-5-yl]-5-methyl-2-furamide;
N-[2-azabicyclo[2.2.1]hept-5-yl]-5-phenyl-2-furamide;
N-[2-azabicyclo[2.2.1]hept-5-yl]-5-(2-fluorophenyl)-2-furamide;
N-[2-azabicyclo[2.2.1]hept-5-yl]-5-(3-fluorophenyl)-2-furamide;
N-[2-azabicyclo[2.2.1]hept-5-yl]-5-(4-fluorophenyl)-2-furamide;
N-[2-azabicyclo[2.2.1]hept-5-yl]-5-(2-chlorophenyl)-2-furamide;
N-[2-azabicyclo[2.2.1]hept-5-yl]-5-(3-chlorophenyl)-2-furamide;
N-[2-azabicyclo[2.2.1]hept-5-yl]-5-(4-chlorophenyl)-2-furamide;
N-[2-azabicyclo[2.2.1]hept-5-yl]-5-(2-methoxyphenyl)-2-furamide;
N-[2-azabicyclo[2.2.1]hept-5-yl]-5-(3-methoxyphenyl)-2-furamide;
N-]2-azabicyclo[2.2.1]hept-5-yl]-5-(4-methoxyphenyl)-2-furamide;
N-[2-azabicyclo[2.2.1]hept-5-yl]-5-(2-methylphenyl)-2-furamide;
N-[2-azabicyclo[2.2.1]hept-5-yl]-5-(3-methylphenyl)-2-furamide;
N-[2-azabicyclo[2.2.1]hept-5-yl]-5-(4-methylphenyl)-2-furamide;
N-[2-azabicyclo[2.2.1]hept-5-yl]-5-(2-hydroxyphenyl)-2-furamide;
N-[2-azabicyclo[2.2.1]hept-5-yl]-5-(3-hydroxyphenyl)-2-furamide;
N-[2-azabicyclo[2.2.1]hept-5-yl]-5-(4-hydroxyphenyl)-2-furamide;
5-(2-aminophenyl)-N-[2-azabicyclo[2.2.1]hept-5-yl]-2-furamide;
5-(3-aminophenyl)-N-[2-azabicyclo[2.2.1]hept-5-yl]-2-furamide;
5-(4-aminophenyl)-N-[2-azabicyclo[2.2.1]hept-5-yl]-2-furamide;
5-(2-acetylaminophenyl)-N-[2-azabicyclo[2.2.1]hept-5-yl]-2-furamide;

5-(3-acetylaminophenyl)-N-[2-azabicyclo[2.2.1]hept-5-yl]-2-furamide;

5-(4-acetylaminophenyl)-N-[2-azabicyclo[2.2.1]hept-5-yl]-2-furamide;

N-[2-azabicyclo[2.2.1]hept-5-yl]-5-(2-trifluoroacetamidophenyl)-2-furamide;

N-[2-azabicyclo[2.2.1]hept-5-yl]-5-(3-trifluoroacetamidophenyl)-2-furamide;

N-[2-azabicyclo[2.2.1]hept-5-yl]-5-(4-trifluoroacetamidophenyl)-2-furamide;

N-[2-azabicyclo[2.2.1]hept-5-yl]-5-bromo-1,3-thiazole-2-carboxamide;

N-[2-azabicyclo[2.2.1]hept-5-yl]-5-chloro-1,3-thiazole-2-carboxamide;

N-[2-azabicyclo[2.2.1]hept-5-yl]-5-methyl-1,3-thiazole-2-carboxamide;

N-[2-azabicyclo[2.2.1]hept-5-yl]-5-phenyl-1,3-thiazole-2-carboxamide;

N-[2-azabicyclo[2.2.1]hept-5-yl]-5-(2-fluorophenyl)-1,3-thiazole-2-carboxamide;

N-[2-azabicyclo[2.2.1]hept-5-yl]-5-(3-fluorophenyl)-1,3-thiazole-2-carboxamide;

N-[2-azabicyclo[2.2.1]hept-5-yl]-5-(4-fluorophenyl)-1,3-thiazole-2-carboxamide;

N-[2-azabicyclo[2.2.1]hept-5-yl]-5-(2-chlorophenyl)-1,3-thiazole-2-carboxamide;

N-[2-azabicyclo[2.2.1]hept-5-yl]-5-(3-chlorophenyl)-1,3-thiazole-2-carboxamide;

N-[2-azabicyclo[2.2.1]hept-5-yl]-5-(4-chlorophenyl)-1,3-thiazole-2-carboxamide;

N-[2-azabicyclo[2.2.1]hept-5-yl]-5-(2-methoxyphenyl)-1,3-thiazole-2-carboxamide;

N-[2-azabicyclo[2.2.1]hept-5-yl]-5-(3-methoxyphenyl)-1,3-thiazole-2-carboxamide;

N-[2-azabicyclo[2.2.1]hept-5-yl]-5-(4-methoxyphenyl)-1,3-thiazole-2-carboxamide;

N-[2-azabicyclo[2.2.1]hept-5-yl]-5-(2-methylphenyl)-1,3-thiazole-2-carboxamide;

N-[2-azabicyclo[2.2.1]hept-5-yl]-5-(3-methylphenyl)-1,3-thiazole-2-carboxamide;

N-[2-azabicyclo[2.2.1]hept-5-yl]-5-(4-methylphenyl)-1,3-thiazole-2-carboxamide;

N-[2-azabicyclo[2.2.1]hept-5-yl]-5-(2-hydroxyphenyl)-1,3-thiazole-2-carboxamide;

N-[2-azabicyclo[2.2.1]hept-5-yl]-5-(3-hydroxyphenyl)-1,3-thiazole-2-carboxamide;

N-[2-azabicyclo[2.2.1]hept-5-yl]-5-(4-hydroxyphenyl)-1,3-thiazole-2-carboxamide;

5-(2-aminophenyl)-N-[2-azabicyclo[2.2.1]hept-5-yl]-1,3-thiazole-2-carboxamide;

5-(3-aminophenyl)-N-[2-azabicyclo[2.2.1]hept-5-yl]-1,3-thiazole-2-carboxamide;

5-(4-aminophenyl)-N-[2-azabicyclo[2.2.1]hept-5-yl]-1,3-thiazole-2-carboxamide;

5-(2-acetylaminophenyl)-N-[2-azabicyclo[2.2.1]hept-5-yl]-1,3-thiazole-2-carboxamide;

5-(3-acetylaminophenyl)-N-[2-azabicyclo[2.2.1]hept-5-yl]-1,3-thiazole-2-carboxamide;

5-(4-acetylaminophenyl)-N-[2-azabicyclo[2.2.1]hept-5-yl]-1,3-thiazole-2-carboxamide;

N-[2-azabicyclo[2.2.1]hept-5-yl]-5-(2-trifluoroacetamidophenyl)-1,3-thiazole-2-carboxamide N-[2-azabicyclo[2.2.1]hept-5-yl]-5-(3-trifluoroacetamidophenyl)-1,3-thiazole-2-carboxamide;

N-[2-azabicyclo[2.2.1]hept-5-yl]-5-(4-trifluoroacetamidophenyl)-1,3-thiazole-2-carboxamide;

N-[2-azabicyclo[2.2.1]hept-5-yl]-5-bromo-1,3-oxazole-2-carboxamide;

N-[2-azabicyclo[2.2.1]hept-5-yl]-5-chloro-1,3-oxazole-2-carboxamide;

N-[2-azabicyclo[2.2.1]hept-5-yl]-5-methyl-1,3-oxazole-2-carboxamide;

N-[2-azabicyclo[2.2.1]hept-5-yl]-5-phenyl-1,3-oxazole-2-carboxamide;

N-[2-azabicyclo[2.2.1]hept-5-yl]-5-(2-fluorophenyl)-1,3-oxazole-2-carboxamide;

N-[2-azabicyclo[2.2.1]hept-5-yl]-5-(3-fluorophenyl)-1,3-oxazole-2-carboxamide;

N-[2-azabicyclo[2.2.1]hept-5-yl]-5-(4-fluorophenyl)-1,3-oxazole-2-carboxamide;

N-[2-azabicyclo[2.2.1]hept-5-yl]-5-(2-chlorophenyl)-1,3-oxazole-2-carboxamide;

N-[2-azabicyclo[2.2.1]hept-5-yl]-5-(3-chlorophenyl)-1,3-oxazole-2-carboxamide;

N-[2-azabicyclo[2.2.1]hept-5-yl]-5-(4-chlorophenyl)-1,3-oxazole-2-carboxamide;

N-[2-azabicyclo[2.2.1]hept-5-yl]-5-(2-methoxyphenyl)-1,3-oxazole-2-carboxamide;

N-[2-azabicyclo[2.2.1]hept-5-yl]-5-(3-methoxyphenyl)-1,3-oxazole-2-carboxamide;

N-[2-azabicyclo[2.2.1]hept-5-yl]-5-(4-methoxyphenyl)-1,3-oxazole-2-carboxamide;

N-[2-azabicyclo[2.2.1]hept-5-yl]-5-(2-methylphenyl)-1,3-oxazole-2-carboxamide;

N-[2-azabicyclo[2.2.1]hept-5-yl]-5-(3-methylphenyl)-1,3-oxazole-2-carboxamide;

N-[2-azabicyclo[2.2.1]hept-5-yl]-5-(4-methylphenyl)-1,3-oxazole-2-carboxamide;

N-[2-azabicyclo[2.2.1]hept-5-yl]-5-(2-hydroxyphenyl)-1,3-oxazole-2-carboxamide;

N-[2-azabicyclo[2.2.1]hept-5-yl]-5-(3-hydroxyphenyl)-1,3-oxazole-2-carboxamide;

N-[2-azabicyclo[2.2.1]hept-5-yl]-5-(4-hydroxyphenyl)-1,3-oxazole-2-carboxamide;

5-(2-aminophenyl)-N-[2-azabicyclo[2.2.1]hept-5-yl]-1,3-oxazole-2-carboxamide;

5-(3-aminophenyl)-N-[2-azabicyclo[2.2.1]hept-5-yl]-1,3-oxazole-2-carboxamide;

5-(4-aminophenyl)-N-[2-azabicyclo[2.2.1]hept-5-yl]-1,3-oxazole-2-carboxamide;

5-(2-acetylaminophenyl)-N-[2-azabicyclo[2.2.1]hept-5-yl]-1,3-oxazole-2-carboxamide;

5-(3-acetylaminophenyl)-N-[2-azabicyclo[2.2.1]hept-5-yl]-1,3-oxazole-2-carboxamide;

5-(4-acetylaminophenyl)-N-[2-azabicyclo[2.2.1]hept-5-yl]-1,3-oxazole-2-carboxamide;

N-[2-azabicyclo[2.2.1]hept-5-yl]-5-(2-trifluoroacetamidophenyl)-1,3-oxazole-2-carboxamide;

N-[2-azabicyclo[2.2.1]hept-5-yl]-5-(3-trifluoroacetamidophenyl)-1,3-oxazole-2-carboxamide;

N-[2-azabicyclo[2.2.1]hept-5-yl]-5-(4-trifluoroacetamidophenyl)-1,3-oxazole-2-carboxamide; or a pharmaceutically acceptable salt thereof, provided that the compound is the pure enantiomer or racemic mixture thereof.

23. The compound of claim 20, wherein the compound is

N-[2-azabicyclo[2.2.1]hept-6-yl]-5-bromothiophene-2-carboxamide;
N-[2-azabicyclo[2.2.1]hept-6-yl]-5-chlorothiophene-2-carboxamide;
N-[2-azabicyclo[2.2.1]hept-6-yl]-5-methylthiophene-2-carboxamide;
N-[2-azabicyclo[2.2.1]hept-6-yl]-5-phenylthiophene-2-carboxamide;
N-[2-azabicyclo[2.2.1]hept-6-yl]-5-(2-fluorophenyl)thiophene-2-carboxamide;
N-[2-azabicyclo[2.2.1]hept-6-yl]-5-(3-fluorophenyl)thiophene-2-carboxamide;
N-[2-azabicyclo[2.2.1]hept-6-yl]-5-(4-fluorophenyl)thiophene-2-carboxamide;
N-[2-azabicyclo[2.2.1]hept-6-yl]-5-(2-chlorophenyl)thiophene-2-carboxamide;
N-[2-azabicyclo[2.2.1]hept-6-yl]-5-(3-chlorophenyl)thiophene-2-carboxamide;
N-[2-azabicyclo[2.2.1]hept-6-yl]-5-(4-chlorophenyl)thiophene-2-carboxamide;
N-[2-azabicyclo[2.2.1]hept-6-yl]-5-(2-methoxyphenyl)thiophene-2-carboxamide;
N-[2-azabicyclo[2.2.1]hept-6-yl]-5-(3-methoxyphenyl)thiophene-2-carboxamide;
N-[2-azabicyclo[2.2.1]hept-6-yl]-5-(4-methoxyphenyl)thiophene-2-carboxamide;
N-[2-azabicyclo[2.2.1]hept-6-yl]-5-(2-methylphenyl)thiophene-2-carboxamide;
N-[2-azabicyclo[2.2.1]hept-6-yl]-5-(3-methylphenyl)thiophene-2-carboxamide;
N-[2-azabicyclo[2.2.1]hept-6-yl]-5-(4-methylphenyl)thiophene-2-carboxamide;
N-[2-azabicyclo[2.2.1]hept-6-yl]-5-(2-hydroxyphenyl)thiophene-2-carboxamide;
N-[2-azabicyclo[2.2.1]hept-6-yl]-5-(3-hydroxyphenyl)thiophene-2-carboxamide;
N-[2-azabicyclo[2.2.1]hept-6-yl]-5-(4-hydroxyphenyl)thiophene-2-carboxamide;
5-(2-aminophenyl)-N-[2-azabicyclo[2.2.1]hept-6-yl]thiophene-2-carboxamide;
5-(3-aminophenyl)-N-[2-azabicyclo[2.2.1]hept-6-yl]thiophene-2-carboxamide;
5-(4-aminophenyl)-N-[2-azabicyclo[2.2.1]hept-6-yl]thiophene-2-carboxamide;
5-(2-acetylaminophenyl)-N-[2-azabicyclo[2.2.1]hept-6-yl]thiophene-2-carboxamide;
5-(3-acetylaminophenyl)-N-[2-azabicyclo[2.2.1]hept-6-yl]thiophene-2-carboxamide;
5-(4-acetylaminophenyl)-N-[2-azabicyclo[2.2.1]hept-6-yl]thiophene-2-carboxamide;
N-[2-azabicyclo[2.2.1]hept-6-yl]-5-(2-trifluoroacetamidophenyl)thiophene-2-carboxamide;
N-[2-azabicyclo[2.2.1]hept-6-yl]-5-(3-trifluoroacetamidophenyl)thiophene-2-carboxamide;
N-[2-azabicyclo[2.2.1]hept-6-yl]-5-(4-trifluoroacetamidophenyl)thiophene-2-carboxamide;
N-[2-azabicyclo[2.2.1]hept-6-yl]-5-bromo-2-furamide;
N-[2-azabicyclo[2.2.1]hept-6-yl]-5-chloro-2-furamide;
N-[2-azabicyclo[2.2.1]hept-6-yl]-5-methyl-2-furamide;
N-[2-azabicyclo[2.2.1]hept-6-yl]-5-phenyl-2-furamide;
N-[2-azabicyclo[2.2.1]hept-6-yl]-5-(2-fluorophenyl)-2-furamide;
N-[2-azabicyclo[2.2.1]hept-6-yl]-5-(3-fluorophenyl)-2-furamide;
N-[2-azabicyclo[2.2.1]hept-6-yl]-5-(4-fluorophenyl)-2-furamide;
N-[2-azabicyclo[2.2.1]hept-6-yl]-5-(2-chlorophenyl)-2-furamide;
N-[2-azabicyclo[2.2.1]hept-6-yl]-5-(3-chlorophenyl)-2-furamide;
N-[2-azabicyclo[2.2.1]hept-6-yl]-5-(4-chlorophenyl)-2-furamide;
N-[2-azabicyclo[2.2.1]hept-6-yl]-5-(2-methoxyphenyl)-2-furamide;
N-[2-azabicyclo[2.2.1]hept-6-yl]-5-(3-methoxyphenyl)-2-furamide;
N-[2-azabicyclo[2.2.1]hept-6-yl]-5-(4-methoxyphenyl)-2-furamide;
N-[2-azabicyclo[2.2.1]hept-6-yl]-5-(2-methylphenyl)-2-furamide;
N-[2-azabicyclo[2.2.1]hept-6-yl]-5-(3-methylphenyl)-2-furamide;
N-[2-azabicyclo[2.2.1]hept-6-yl]-5-(4-methylphenyl)-2-furamide;
N-[2-azabicyclo[2.2.1]hept-6-yl]-5-(2-hydroxyphenyl)-2-furamide;
N-[2-azabicyclo[2.2.1]hept-6-yl]-5-(3-hydroxyphenyl)-2-furamide;
N-[2-azabicyclo[2.2.1]hept-6-yl]-5-(4-hydroxyphenyl)-2-furamide;
5-(2-aminophenyl)-N-[2-azabicyclo[2.2.1]hept-6-yl]-2-furamide;
5-(3-aminophenyl)-N-[2-azabicyclo[2.2.1]hept-6-yl]-2-furamide;
5-(4-aminophenyl)-N-[2-azabicyclo[2.2.1]hept-6-yl]-2-furamide;
5-(2-acetylaminophenyl)-N-[2-azabicyclo[2.2.1]hept-6-yl]-2-furamide;
5-(3-acetylaminophenyl)-N-[2-azabicyclo[2.2.1]hept-6-yl]-2-furamide;
5-(4-acetylaminophenyl)-N-[2-azabicyclo[2.2.1]hept-6-yl]-2-furamide;
N-[2-azabicyclo[2.2.1]hept-6-yl]-5-(2-trifluoroacetamidophenyl)-2-furamide;
N-[2-azabicyclo[2.2.1]hept-6-yl]-5-(3-trifluoroacetamidophenyl)-2-furamide;
N-[2-azabicyclo[2.2.1]hept-6-yl]-5-(4-trifluoroacetamidophenyl)-2-furamide;
N-[2-azabicyclo[2.2.1]hept-6-yl]-5-bromo-1,3-thiazole-2-carboxamide;
N-[2-azabicyclo[2.2.1]hept-6-yl]-5-chloro-1,3-thiazole-2-carboxamide;
N-[2-azabicyclo[2.2.1]hept-6-yl]-5-methyl-1,3-thiazole-2-carboxamide;
N-[2-azabicyclo[2.2.1]hept-6-yl]-5-phenyl-1,3-thiazole-2-carboxamide;
N-[2-azabicyclo[2.2.1]hept-6-yl]-5-(2-fluorophenyl)-1,3-thiazole-2-carboxamide;

N-[2-azabicyclo[2.2.1]hept-6-yl]-5-(3-fluorophenyl)-1,3-thiazole-2-carboxamide;
N-[2-azabicyclo[2.2.1]hept-6-yl]-5-(4-fluorophenyl)-1,3-thiazole-2-carboxamide;
N-[2-azabicyclo[2.2.1]hept-6-yl]-5-(2-chlorophenyl)-1,3-thiazole-2-carboxamide;
N-[2-azabicyclo[2.2.1]hept-6-yl]-5-(3-chlorophenyl)-1,3-thiazole-2-carboxamide;
N-[2-azabicyclo[2.2.1]hept-6-yl]-5-(4-chlorophenyl)-1,3-thiazole-2-carboxamide;
N-[2-azabicyclo[2.2.1]hept-6-yl]-5-(2-methoxyphenyl)-1,3-thiazole-2-carboxamide;
N-[2-azabicyclo[2.2.1]hept-6-yl]-5-(3-methoxyphenyl)-1,3-thiazole-2-carboxamide;
N-[2-azabicyclo[2.2.1]hept-6-yl]-5-(4-methoxyphenyl)-1,3-thiazole-2-carboxamide;
N-[2-azabicyclo[2.2.1]hept-6-yl]-5-(2-methylphenyl)-1,3-thiazole-2-carboxamide;
N-[2-azabicyclo[2.2.1]hept-6-yl]-5-(3-methylphenyl)-1,3-thiazole-2-carboxamide;
N-[2-azabicyclo[2.2.1]hept-6-yl]-5-(4-methylphenyl)-1,3-thiazole-2-carboxamide;
N-[2-azabicyclo[2.2.1]hept-6-yl]-5-(2-hydroxyphenyl)-1,3-thiazole-2-carboxamide;
N-[2-azabicyclo[2.2.1]hept-6-yl]-5-(3-hydroxyphenyl)-1,3-thiazole-2-carboxamide;
N-[2-azabicyclo[2.2.1]hept-6-yl]-5-(4-hydroxyphenyl)-1,3-thiazole-2-carboxamide;
5-(2-aminophenyl)-N-[2-azabicyclo[2.2.1]hept-6-yl]-1,3-thiazole-2-carboxamide;
5-(3-aminophenyl)-N-[2-azabicyclo[2.2.1]hept-6-yl]-1,3-thiazole-2-carboxamide;
5-(4-aminophenyl)-N-[2-azabicyclo[2.2.1]hept-6-yl]-1,3-thiazole-2-carboxamide;
5-(2-acetylaminophenyl)-N-[2-azabicyclo[2.2.1]hept-6-yl]-1,3-thiazole-2-carboxamide;
5-(3-acetylaminophenyl)-N-[2-azabicyclo[2.2.1]hept-6-yl]-1,3-thiazole-2-carboxamide;
5-(4-acetylaminophenyl)-N-[2-azabicyclo[2.2.1]hept-6-yl]-1,3-thiazole-2-carboxamide;
N-[2-azabicyclo[2.2.1]hept-6-yl]-5-(2-trifluoroacetamidophenyl)-1,3-thiazole-2-carboxamide;
N-[2-azabicyclo[2.2.1]hept-6-yl]-5-(3-trifluoroacetamidophenyl)-1,3-thiazole-2-carboxamide;
N-[2-azabicyclo[2.2.1]hept-6-yl]-5-(4-trifluoroacetamidophenyl)-1,3-thiazole-2-carboxamide;
N-[2-azabicyclo[2.2.1]hept-6-yl]-5-bromo-1,3-oxazole-2-carboxamide;
N-[2-azabicyclo[2.2.1]hept-6-yl]-5-chloro-1,3-oxazole-2-carboxamide;
N-[2-azabicyclo[2.2.1]hept-6-yl]-5-methyl-1,3-oxazole-2-carboxamide;
N-[2-azabicyclo[2.2.1]hept-6-yl]-5-phenyl-1,3-oxazole-2-carboxamide;
N-[2-azabicyclo[2.2.1]hept-6-yl]-5-(2-fluorophenyl)-1,3-oxazole-2-carboxamide;
N-[2-azabicyclo[2.2.1]hept-6-yl]-5-(3-fluorophenyl)-1,3-oxazole-2-carboxamide;
N-[2-azabicyclo[2.2.1]hept-6-yl]-5-(4-fluorophenyl)-1,3-oxazole-2-carboxamide;
N-[2-azabicyclo[2.2.1]hept-6-yl]-5-(2-chlorophenyl)-1,3-oxazole-2-carboxamide;
N-[2-azabicyclo[2.2.1]hept-6-yl]-5-(3-chlorophenyl)-1,3-oxazole-2-carboxamide;
N-[2-azabicyclo[2.2.1]hept-6-yl]-5-(4-chlorophenyl)-1,3-oxazole-2-carboxamide;
N-[2-azabicyclo[2.2.1]hept-6-yl]-5-(2-methoxyphenyl)-1,3-oxazole-2-carboxamide;
N-[2-azabicyclo[2.2.1]hept-6-yl]-5-(3-methoxyphenyl)-1,3-oxazole-2-carboxamide;
N-[2-azabicyclo[2.2.1]hept-6-yl]-5-(4-methoxyphenyl)-1,3-oxazole-2-carboxamide;
N-[2-azabicyclo[2.2.1]hept-6-yl]-5-(2-methylphenyl)-1,3-oxazole-2-carboxamide;
N-[2-azabicyclo[2.2.1]hept-6-yl]-5-(3-methylphenyl)-1,3-oxazole-2-carboxamide;
N-[2-azabicyclo[2.2.1]hept-6-yl]-5-(4-methylphenyl)-1,3-oxazole-2-carboxamide;
N-[2-azabicyclo[2.2.1]hept-6-yl]-5-(2-hydroxyphenyl)-1,3-oxazole-2-carboxamide;
N-[2-azabicyclo[2.2.1]hept-6-yl]-5-(3-hydroxyphenyl)-1,3-oxazole-2-carboxamide;
N-[2-azabicyclo[2.2.1]hept-6-yl]-5-(4-hydroxyphenyl)-1,3-oxazole-2-carboxamide;
5-(2-aminophenyl)-N-[2-azabicyclo[2.2.1]hept-6-yl]-1,3-oxazole-2-carboxamide;
5-(3-aminophenyl)-N-[2-azabicyclo[2.2.1]hept-6-yl]-1,3-oxazole-2-carboxamide;
5-(4-aminophenyl)-N-[2-azabicyclo[2.2.1]hept-6-yl]-1,3-oxazole-2-carboxamide;
5-(2-acetylaminophenyl)-N-[2-azabicyclo[2.2.1]hept-6-yl]-1,3-oxazole-2-carboxamide;
5-(3-acetylaminophenyl)-N-[2-azabicyclo[2.2.1]hept-6-yl]-1,3-oxazole-2-carboxamide;
5-(4-acetylaminophenyl)-N-[2-azabicyclo[2.2.1]hept-6-yl]-1,3-oxazole-2-carboxamide;
N-[2-azabicyclo[2.2.1]hept-6-yl]-5-(2-trifluoroacetamidophenyl)-1,3-oxazole-2-carboxamide;
N-[2-azabicyclo[2.2.1]hept-6-yl]-5-(3-trifluoroacetamidophenyl)-1,3-oxazole-2-carboxamide;
N-[2-azabicyclo[2.2.1]hept-6-yl]-5-(4-trifluoroacetamidophenyl)-1,3-oxazole-2-carboxamide;
or a pharmaceutically acceptable salt thereof, provided that the compound is the pure enantiomer or racemic mixture thereof.

\* \* \* \* \*